United States Patent
Smutney et al.

(10) Patent No.: US 9,358,352 B2
(45) Date of Patent: Jun. 7, 2016

(54) DRY POWDER DRUG DELIVERY SYSTEM AND METHODS

(75) Inventors: Chad C. Smutney, Watertown, CT (US);
Benoit Adamo, Mount Kisco, NY (US);
John M. Polidoro, Coventry, CT (US);
P. Spencer Kinsey, Sandy Hook, CT (US); Dennis Overfield, Fairfield, CT (US); Carl Sahi, Coventry, CT (US);
Christine Billings, Danbury, CT (US);
Mark T. Marino, Danbury, CT (US)

(73) Assignee: MannKind Corporation, Valencia, CA (US)

( * ) Notice: Subject to any disclaimer, the term of this patent is extended or adjusted under 35 U.S.C. 154(b) by 613 days.

(21) Appl. No.: 13/702,024

(22) PCT Filed: Jun. 21, 2011

(86) PCT No.: PCT/US2011/041303
§ 371 (c)(1),
(2), (4) Date: Jan. 16, 2013

(87) PCT Pub. No.: WO2011/163272
PCT Pub. Date: Dec. 29, 2011

(65) Prior Publication Data
US 2013/0104887 A1 May 2, 2013

Related U.S. Application Data

(63) Continuation-in-part of application No. 12/717,884, filed on Mar. 4, 2010, which is a continuation-in-part of application No. 12/484,137, filed on Jun. 12, 2009.

(60) Provisional application No. 61/357,039, filed on Jun.21, 2010, provisional application No. 61/411,775, (Continued)

(51) Int. Cl.
*A61M 15/00* (2006.01)
*A61M 11/06* (2006.01)

(52) U.S. Cl.
CPC ....... *A61M 15/0091* (2013.01); *A61M 15/0025* (2014.02); *A61M 15/0028* (2013.01);
(Continued)

(58) Field of Classification Search
CPC . A61M 15/00; A61M 15/001; A61M 15/002; A61M 15/0028; A61M 15/003; A61M 15/0045; A61M 15/0043
See application file for complete search history.

(56) References Cited

U.S. PATENT DOCUMENTS

| | | |
|---|---|---|
| 2,549,303 A | 4/1951 | Friden |
| 4,013,075 A | 3/1977 | Cocozza |

(Continued)

FOREIGN PATENT DOCUMENTS

| | | |
|---|---|---|
| EP | 220958 | 5/1987 |
| JP | 10234827 | 9/1998 |

(Continued)

OTHER PUBLICATIONS

Drug Delivery, Easing the drug delivery route, Jun. 2006, Pharmaceutical & Medical Packaging News, Canon Communications.
(Continued)

*Primary Examiner* — Valerie L Woodward
(74) *Attorney, Agent, or Firm* — K&L Gates LLP; Louis C. Cullman; Robert W. Winn

(57) ABSTRACT

A pulmonary drug delivery system is disclosed, including a breath-powered, dry powder inhaler, and a cartridge for delivering a dry powder formulation. The inhaler and cartridge can be provided with a drug delivery formulation comprising, for example, a diketopiperazine and an active ingredient, including, small organic molecules, peptides and proteins, including, insulin and glucagon-like peptide 1 for the treatment of disease and disorders, for example, endocrine disease such as diabetes and/or obesity.

21 Claims, 30 Drawing Sheets

Related U.S. Application Data filed on Nov. 9, 2010, provisional application No. 61/222,810, filed on Jul. 2, 2009, provisional application No. 61/258,184, filed on Nov. 4, 2009, provisional application No. 61/157,506, filed on Mar. 4, 2009, provisional application No. 61/061,551, filed on Jun. 13, 2008.

(52) U.S. Cl.
CPC ........... *A61M15/0043* (2014.02); *A61M 11/06* (2013.01); *A61M 2202/064* (2013.01); *A61M 2205/6045* (2013.01); *A61M 2205/6081* (2013.01)

(56) References Cited

U.S. PATENT DOCUMENTS

| | | |
|---|---|---|
| 4,018,619 A | 4/1977 | Webster et al. |
| 4,022,749 A | 5/1977 | Kuechler |
| 4,078,128 A | 3/1978 | Hoyt et al. |
| 4,091,077 A | 5/1978 | Smith et al. |
| 4,102,953 A | 7/1978 | Johnson et al. |
| 4,110,240 A | 8/1978 | Leo et al. |
| D252,707 S | 8/1979 | Besnard |
| 4,187,129 A | 2/1980 | Bost et al. |
| 4,206,758 A | 6/1980 | Hallworth et al. |
| 4,210,140 A | 7/1980 | James et al. |
| D269,463 S | 6/1983 | Young et al. |
| 4,524,769 A | 6/1985 | Wetterlin |
| 4,526,804 A | 7/1985 | Escallon |
| D282,209 S | 1/1986 | Newell et al. |
| 4,615,817 A | 10/1986 | McCoy |
| 4,624,861 A | 11/1986 | Yale et al. |
| D288,852 S | 3/1987 | Miyoshi |
| 4,668,218 A | 5/1987 | Virtanen |
| 4,681,752 A | 7/1987 | Melillo |
| D295,321 S | 4/1988 | Hallworth |
| 4,792,451 A | 12/1988 | Kim |
| D301,273 S | 5/1989 | Leonard |
| 4,887,722 A | 12/1989 | Greenward, Sr. |
| 4,907,583 A | 3/1990 | Wetterlin |
| 4,927,555 A | 5/1990 | Colarusso, Jr. |
| 4,981,295 A | 1/1991 | Belman et al. |
| 4,984,158 A | 1/1991 | Hillsman |
| 4,998,624 A | 3/1991 | Capes et al. |
| D316,902 S | 5/1991 | Hoelfing |
| 5,021,376 A | 6/1991 | Nienburg et al. |
| D321,570 S | 11/1991 | Blasdell et al. |
| 5,069,204 A | 12/1991 | Smith et al. |
| 5,075,027 A | 12/1991 | Dixit et al. |
| 5,098,590 A | 3/1992 | Dixit et al. |
| 5,124,291 A | 6/1992 | Bremer et al. |
| D331,106 S | 11/1992 | Fuchs |
| 5,167,506 A | 12/1992 | Kilis et al. |
| D337,636 S | 7/1993 | Kocinski |
| D338,062 S | 8/1993 | Yair |
| D338,268 S | 8/1993 | Kobayashi et al. |
| D340,975 S | 11/1993 | Sladek |
| 5,270,305 A | 12/1993 | Palmer |
| D344,796 S | 3/1994 | Sochon et al. |
| D344,797 S | 3/1994 | Sochon et al. |
| D345,013 S | 3/1994 | Huck et al. |
| 5,306,453 A | 4/1994 | Shulman |
| D347,057 S | 5/1994 | Yair |
| D348,100 S | 6/1994 | Clarke |
| D348,928 S | 7/1994 | Ashley et al. |
| D348,929 S | 7/1994 | Paton |
| 5,327,883 A | 7/1994 | Williams et al. |
| 5,333,106 A | 7/1994 | Lanpher et al. |
| D349,572 S | 8/1994 | Jagnandan et al. |
| D350,193 S | 8/1994 | Huck et al. |
| D350,602 S | 9/1994 | Hobbs |
| D350,821 S | 9/1994 | Wright et al. |
| 5,352,461 A | 10/1994 | Feldstein et al. |
| 5,358,734 A | 10/1994 | Lenox et al. |
| D352,107 S | 11/1994 | Meier et al. |
| 5,363,842 A | 11/1994 | Mishelevich et al. |
| 5,364,838 A | 11/1994 | Rubsamen |
| 5,372,128 A | 12/1994 | Haber et al. |
| D355,029 S | 1/1995 | Kinneir et al. |
| 5,385,904 A | 1/1995 | Andersson et al. |
| D357,603 S | 4/1995 | Wolff |
| 5,404,871 A | 4/1995 | Goodman et al. |
| 5,413,804 A | 5/1995 | Rhodes |
| D359,153 S | 6/1995 | Viggiano |
| D359,555 S | 6/1995 | Funai et al. |
| 5,437,271 A | 8/1995 | Hodson et al. |
| D362,500 S | 9/1995 | Cook et al. |
| 5,447,150 A | 9/1995 | Bacon |
| D363,775 S | 10/1995 | Hobbs |
| 5,454,871 A | 10/1995 | Liaw et al. |
| 5,455,335 A | 10/1995 | Kahne et al. |
| 5,469,750 A | 11/1995 | Lloyd et al. |
| 5,469,971 A | 11/1995 | Higuchi |
| 5,477,285 A | 12/1995 | Riddle et al. |
| D365,876 S | 1/1996 | Chawla |
| 5,482,032 A | 1/1996 | Smith et al. |
| 5,492,112 A | 2/1996 | Mecikalski et al. |
| D368,364 S | 4/1996 | Reitano et al. |
| 5,503,852 A | 4/1996 | Steiner et al. |
| 5,506,203 A | 4/1996 | Backstrom et al. |
| D370,255 S | 5/1996 | Yamamoto et al. |
| 5,524,613 A | 6/1996 | Haber et al. |
| 5,533,505 A | 7/1996 | Kallstrand et al. |
| 5,547,929 A | 8/1996 | Anderson, Jr. et al. |
| 5,570,810 A | 11/1996 | Lambelet, Jr. et al. |
| 5,571,795 A | 11/1996 | Kahne et al. |
| 5,577,497 A | 11/1996 | Mecikalski et al. |
| D377,215 S | 1/1997 | Rand |
| D377,686 S | 1/1997 | Waldeck et al. |
| D377,861 S | 2/1997 | Jacober |
| 5,598,835 A | 2/1997 | von Schrader |
| 5,617,844 A | 4/1997 | King |
| 5,619,984 A | 4/1997 | Hodson et al. |
| 5,623,724 A | 4/1997 | Gurkovich et al. |
| 5,623,920 A | 4/1997 | Bryant |
| D379,506 S | 5/1997 | Maher |
| D381,416 S | 7/1997 | Hansson et al. |
| 5,642,728 A | 7/1997 | Andersson et al. |
| 5,645,051 A | 7/1997 | Schultz |
| 5,655,516 A | 8/1997 | Goodman et al. |
| 5,655,523 A | 8/1997 | Hodson et al. |
| 5,660,169 A | 8/1997 | Kallstrand et al. |
| 5,673,686 A | 10/1997 | Villax et al. |
| 5,690,910 A | 11/1997 | Ahmed et al. |
| D389,238 S | 1/1998 | Kirk, III et al. |
| D389,570 S | 1/1998 | Savolainen |
| D390,651 S | 2/1998 | Smith et al. |
| D390,653 S | 2/1998 | Blasdell et al. |
| 5,740,793 A | 4/1998 | Hodson et al. |
| 5,746,227 A | 5/1998 | Rose et al. |
| D395,147 S | 6/1998 | Vidgren et al. |
| D395,499 S | 6/1998 | Eisele et al. |
| 5,772,085 A | 6/1998 | Bryant et al. |
| D397,435 S | 8/1998 | Naumann |
| 5,794,613 A | 8/1998 | Piskorski |
| D398,992 S | 9/1998 | Feret |
| 5,799,821 A | 9/1998 | Lambelet, Jr. et al. |
| 5,813,397 A | 9/1998 | Goodman et al. |
| 5,839,429 A | 11/1998 | Marnfeldt et al. |
| 5,840,279 A | 11/1998 | Narodylo et al. |
| 5,846,447 A | 12/1998 | Beatty |
| 5,848,589 A | 12/1998 | Welnetz |
| 5,858,099 A | 1/1999 | Sun et al. |
| 5,865,012 A | 2/1999 | Hansson et al. |
| 5,875,776 A | 3/1999 | Vaghefi |
| 5,881,721 A | 3/1999 | Bunce et al. |
| 5,888,477 A | 3/1999 | Gonda et al. |
| D410,541 S | 6/1999 | Moulin |
| D411,005 S | 6/1999 | Coe |
| 5,908,639 A | 6/1999 | Simpkin et al. |
| 5,918,594 A | 7/1999 | Asking et al. |
| 5,924,419 A | 7/1999 | Kotliar |

(56) References Cited

U.S. PATENT DOCUMENTS

| | | |
|---|---|---|
| D412,572 S | 8/1999 | Gray |
| D412,744 S | 8/1999 | Braithwaite |
| D412,978 S | 8/1999 | Cameron |
| D412,979 S | 8/1999 | Weinstein et al. |
| 5,934,273 A | 8/1999 | Andersson et al. |
| 5,954,047 A | 9/1999 | Armer et al. |
| 5,971,951 A | 10/1999 | Ruskewicz |
| D416,085 S | 11/1999 | Forssell et al. |
| D416,621 S | 11/1999 | Forssell et al. |
| D416,998 S | 11/1999 | Hodson et al. |
| 5,975,347 A | 11/1999 | Lambelet, Jr. et al. |
| 5,976,569 A | 11/1999 | Milstein |
| 5,980,865 A | 11/1999 | Ahmed et al. |
| 5,983,893 A | 11/1999 | Wetterlin |
| D417,732 S | 12/1999 | Dagsland et al. |
| D417,912 S | 12/1999 | Dagsland et al. |
| 5,997,848 A | 12/1999 | Patton et al. |
| 6,006,747 A | 12/1999 | Eisele et al. |
| D418,600 S | 1/2000 | Haerle |
| D420,736 S | 2/2000 | Moulin |
| 6,026,809 A | 2/2000 | Abrams et al. |
| D421,800 S | 3/2000 | Doat |
| 6,039,208 A | 3/2000 | Lambelet et al. |
| 6,045,828 A | 4/2000 | Bystrom et al. |
| 6,051,551 A | 4/2000 | Hughes et al. |
| 6,055,980 A | 5/2000 | Mecikalski et al. |
| 6,056,169 A | 5/2000 | Bruna et al. |
| 6,060,069 A | 5/2000 | Hill et al. |
| 6,071,497 A | 6/2000 | Steiner et al. |
| 6,080,762 A | 6/2000 | Allen et al. |
| D428,486 S | 7/2000 | Schuckmann |
| 6,085,745 A | 7/2000 | Levander et al. |
| 6,087,351 A | 7/2000 | Nye |
| 6,089,228 A | 7/2000 | Smith et al. |
| 6,095,136 A | 8/2000 | Virtanen |
| 6,098,618 A | 8/2000 | Jennings et al. |
| 6,102,035 A | 8/2000 | Asking et al. |
| 6,105,571 A | 8/2000 | Coffee |
| 6,105,574 A | 8/2000 | Jahnsson |
| 6,109,481 A | 8/2000 | Alexander et al. |
| 6,119,684 A | 9/2000 | Nohl et al. |
| 6,119,688 A | 9/2000 | Whaley et al. |
| 6,142,145 A | 11/2000 | Dagsland |
| 6,156,114 A | 12/2000 | Bell et al. |
| 6,158,431 A | 12/2000 | Poole |
| 6,159,360 A | 12/2000 | Gerteis et al. |
| 6,192,876 B1 | 2/2001 | Denyer et al. |
| 6,193,844 B1 | 2/2001 | McLaughlin et al. |
| 6,193,957 B1 | 2/2001 | Ahmed |
| D438,612 S | 3/2001 | Suh |
| D439,325 S | 3/2001 | Frost |
| D439,656 S | 3/2001 | Andersson et al. |
| D441,446 S | 5/2001 | Dagsland et al. |
| D441,859 S | 5/2001 | Pera |
| D442,685 S | 5/2001 | Sladek |
| 6,235,725 B1 | 5/2001 | Ahmed |
| D444,226 S | 6/2001 | Geert-Jensen et al. |
| 6,250,300 B1 | 6/2001 | Andersson et al. |
| 6,257,232 B1 | 7/2001 | Andersson et al. |
| 6,258,816 B1 | 7/2001 | Singh et al. |
| 6,263,871 B1 | 7/2001 | Brown et al. |
| 6,269,952 B1 | 8/2001 | Watt et al. |
| 6,273,084 B1 | 8/2001 | Frid |
| 6,273,085 B1 | 8/2001 | Eisele et al. |
| 6,273,086 B1 | 8/2001 | Ohki et al. |
| D448,076 S | 9/2001 | Von Schuckmann |
| 6,286,506 B1 | 9/2001 | MacAndrew et al. |
| 6,286,507 B1 | 9/2001 | Jahnsson |
| D449,684 S | 10/2001 | Christrup et al. |
| D450,117 S | 11/2001 | Braithwaite et al. |
| D451,597 S | 12/2001 | Suh |
| 6,331,318 B1 | 12/2001 | Milstein |
| D452,910 S | 1/2002 | Braithwaite et al. |
| D453,264 S | 2/2002 | Acevedo, Jr. |
| 6,347,629 B1 | 2/2002 | Braithwaite |
| 6,357,442 B1 | 3/2002 | Casper et al. |
| 6,360,743 B1 | 3/2002 | Andersson et al. |
| 6,360,929 B1 | 3/2002 | McCarthy |
| D455,208 S | 4/2002 | Bacon et al. |
| 6,386,195 B1 | 5/2002 | Coffee |
| 6,395,774 B1 | 5/2002 | Milstein |
| D460,173 S | 7/2002 | Harrison et al. |
| 6,415,784 B1 | 7/2002 | Christrup et al. |
| 6,418,926 B1 | 7/2002 | Chawla |
| D461,239 S | 8/2002 | Cassidy |
| 6,427,688 B1 | 8/2002 | Ligotke et al. |
| 6,428,771 B1 | 8/2002 | Steiner et al. |
| 6,439,227 B1 | 8/2002 | Myrman et al. |
| D463,544 S | 9/2002 | Engelberth et al. |
| 6,443,143 B1 | 9/2002 | Ishida et al. |
| 6,444,226 B1 | 9/2002 | Steiner et al. |
| 6,446,626 B1 | 9/2002 | Virtanen |
| 6,446,627 B1 | 9/2002 | Bowman et al. |
| 6,451,337 B1 | 9/2002 | Smith et al. |
| 6,457,470 B1 | 10/2002 | Coffee |
| 6,470,884 B2 | 10/2002 | Horlin |
| 6,484,717 B1 | 11/2002 | Dagsland et al. |
| D469,527 S | 1/2003 | Keller et al. |
| 6,509,313 B1 | 1/2003 | Smith |
| D469,866 S | 2/2003 | Albulet et al. |
| 6,514,482 B1 | 2/2003 | Bartus et al. |
| D471,273 S | 3/2003 | Albulet et al. |
| 6,528,096 B1 | 3/2003 | Musa et al. |
| 6,532,437 B1 | 3/2003 | Clardy et al. |
| 6,536,427 B2 | 3/2003 | Davies et al. |
| D473,298 S | 4/2003 | Bowman et al. |
| D473,640 S | 4/2003 | Cuffaro et al. |
| 6,540,672 B1 | 4/2003 | Simonsen et al. |
| 6,543,448 B1 | 4/2003 | Smith et al. |
| D474,536 S | 5/2003 | Albulet et al. |
| D475,133 S | 5/2003 | McLuckie |
| 6,557,549 B2 | 5/2003 | Schmidt et al. |
| 6,567,686 B2 | 5/2003 | Sexton |
| 6,568,390 B2 | 5/2003 | Nichols et al. |
| 6,571,793 B1 | 6/2003 | Nilsson et al. |
| D477,665 S | 7/2003 | Myrman et al. |
| 6,589,560 B2 | 7/2003 | Foster et al. |
| 6,591,832 B1 | 7/2003 | DeJonge |
| 6,595,205 B2 | 7/2003 | Andersson et al. |
| 6,595,208 B1 | 7/2003 | Coffee et al. |
| D478,983 S | 8/2003 | Whitehall et al. |
| 6,606,992 B1 | 8/2003 | Schuler et al. |
| D479,745 S | 9/2003 | Albulet et al. |
| 6,613,308 B2 | 9/2003 | Bartus et al. |
| 6,615,987 B1 | 9/2003 | Greenhill et al. |
| 6,626,173 B2 | 9/2003 | Genova et al. |
| D480,806 S | 10/2003 | Engelberth et al. |
| 6,630,169 B1 | 10/2003 | Bot et al. |
| 6,632,258 B1 | 10/2003 | Wheelock et al. |
| 6,635,283 B2 | 10/2003 | Edwards et al. |
| 6,637,431 B2 | 10/2003 | Ekelius et al. |
| 6,640,050 B2 | 10/2003 | Nichols et al. |
| 6,652,885 B2 | 11/2003 | Steiner et al. |
| D483,860 S | 12/2003 | Knoch |
| 6,655,380 B1 | 12/2003 | Andersson et al. |
| 6,655,381 B2 | 12/2003 | Keane et al. |
| 6,668,826 B2 | 12/2003 | Myrman et al. |
| 6,672,304 B1 | 1/2004 | Casper et al. |
| 6,679,255 B2 | 1/2004 | Pera |
| 6,681,768 B2 | 1/2004 | Haaije de Boer et al. |
| 6,701,917 B2 | 3/2004 | O'Leary |
| 6,703,361 B2 | 3/2004 | Weiner et al. |
| 6,705,313 B2 | 3/2004 | Niccolai |
| 6,715,486 B2 | 4/2004 | Gieschen et al. |
| 6,715,487 B2 | 4/2004 | Nichols et al. |
| 6,718,972 B2 | 4/2004 | O'Leary |
| 6,720,407 B2 | 4/2004 | Hughes et al. |
| 6,729,324 B2 | 5/2004 | Casper et al. |
| 6,729,328 B2 | 5/2004 | Goldemann |
| 6,745,761 B2 | 6/2004 | Christrup et al. |
| 6,748,947 B2 | 6/2004 | Keane et al. |
| 6,755,190 B2 | 6/2004 | Rasmussen |
| D492,769 S | 7/2004 | Hatanaka |
| D493,220 S | 7/2004 | Burge et al. |

(56) References Cited

U.S. PATENT DOCUMENTS

| | | |
|---|---|---|
| D493,519 S | 7/2004 | Jonsson et al. |
| 6,790,496 B1 | 9/2004 | Levander et al. |
| 6,792,945 B2 | 9/2004 | Davies et al. |
| 6,799,572 B2 | 10/2004 | Nichols et al. |
| 6,800,643 B2 | 10/2004 | Cuenoud et al. |
| 6,803,044 B1 | 10/2004 | Catania et al. |
| 6,823,863 B2 | 11/2004 | Huxham et al. |
| D499,802 S | 12/2004 | Pinon et al. |
| 6,830,046 B2 | 12/2004 | Blakley et al. |
| 6,838,075 B2 | 1/2005 | Stevenson et al. |
| 6,848,443 B2 | 2/2005 | Schmidt et al. |
| 6,858,199 B1 | 2/2005 | Edwards et al. |
| 6,860,262 B2 | 3/2005 | Christrup et al. |
| 6,866,037 B1 | 3/2005 | Aslin et al. |
| 6,871,646 B2 | 3/2005 | Keane et al. |
| 6,871,647 B2 | 3/2005 | Allan et al. |
| 6,880,554 B1 | 4/2005 | Coffee |
| 6,887,459 B1 | 5/2005 | Haeberlin |
| 6,889,687 B1 | 5/2005 | Olsson |
| 6,892,728 B2 | 5/2005 | Helgesson et al. |
| 6,904,907 B2 | 6/2005 | Speldrich et al. |
| 6,916,354 B2 | 7/2005 | Elliot |
| 6,918,991 B2 | 7/2005 | Chickering, III et al. |
| 6,921,458 B2 | 7/2005 | Chickering, III et al. |
| 6,921,528 B2 | 7/2005 | Edwards et al. |
| 6,923,175 B2 | 8/2005 | Poole |
| D509,296 S | 9/2005 | Minshull et al. |
| D509,898 S | 9/2005 | Bunce et al. |
| 6,948,496 B2 | 9/2005 | Eason et al. |
| 6,951,215 B1 | 10/2005 | Hoffman |
| D511,208 S | 11/2005 | Pardonge et al. |
| 6,962,006 B2 | 11/2005 | Chickering, III et al. |
| D512,777 S | 12/2005 | Beisner et al. |
| 6,979,437 B2 | 12/2005 | Bartus et al. |
| D514,222 S | 1/2006 | Andersson et al. |
| 6,981,499 B2 | 1/2006 | Andersson et al. |
| D515,696 S | 2/2006 | Lucking et al. |
| D516,211 S | 2/2006 | Minshull et al. |
| D518,170 S | 3/2006 | Clarke et al. |
| D518,171 S | 3/2006 | Anderson et al. |
| 7,025,056 B2 | 4/2006 | Eason et al. |
| 7,028,686 B2 * | 4/2006 | Gonda et al. ............. 128/200.14 |
| 7,032,593 B2 | 4/2006 | Johnston et al. |
| 7,035,294 B2 | 4/2006 | Dove et al. |
| 7,047,967 B2 | 5/2006 | Knudsen |
| 7,060,274 B2 | 6/2006 | Blumberg et al. |
| 7,067,129 B2 | 6/2006 | Blumberg et al. |
| 7,077,130 B2 | 7/2006 | Nichols et al. |
| 7,080,642 B2 | 7/2006 | Hodson et al. |
| 7,093,594 B2 | 8/2006 | Harrison et al. |
| 7,093,595 B2 | 8/2006 | Nesbitt |
| D527,817 S | 9/2006 | Ziegler et al. |
| 7,101,866 B2 | 9/2006 | Biggadike et al. |
| 7,107,988 B2 | 9/2006 | Pinon et al. |
| D529,604 S | 10/2006 | Young et al. |
| 7,128,067 B2 | 10/2006 | Byron et al. |
| 7,132,115 B2 | 11/2006 | Musa et al. |
| 7,140,365 B2 | 11/2006 | Poole et al. |
| D533,268 S | 12/2006 | Olfati |
| 7,143,764 B1 | 12/2006 | Dagsland et al. |
| 7,143,765 B2 | 12/2006 | Asking et al. |
| 7,144,863 B2 | 12/2006 | DeFelippis et al. |
| 7,146,978 B2 | 12/2006 | Edwards et al. |
| 7,163,014 B2 | 1/2007 | Nichols et al. |
| D537,522 S | 2/2007 | Cox et al. |
| 7,171,965 B2 | 2/2007 | Young et al. |
| 7,172,768 B2 | 2/2007 | Hastedt et al. |
| D537,936 S | 3/2007 | Cox et al. |
| D538,423 S | 3/2007 | Berube et al. |
| 7,185,650 B2 | 3/2007 | Huber et al. |
| 7,198,806 B2 | 4/2007 | Berndt |
| 7,219,664 B2 | 5/2007 | Ruckdeschel et al. |
| D544,093 S | 6/2007 | Eriksen |
| 7,231,919 B2 | 6/2007 | Giroux |
| 7,234,459 B2 | 6/2007 | Del Bon |
| 7,234,460 B2 | 6/2007 | Greenleaf et al. |
| 7,234,464 B2 | 6/2007 | Goede et al. |
| 7,246,617 B1 | 7/2007 | Hammer et al. |
| D548,330 S | 8/2007 | Cox et al. |
| 7,258,118 B2 | 8/2007 | Goede et al. |
| D550,835 S | 9/2007 | Tanaka et al. |
| 7,270,124 B2 | 9/2007 | Rasmussen |
| D552,729 S | 10/2007 | Cox et al. |
| 7,278,426 B2 | 10/2007 | Myrman et al. |
| 7,284,553 B2 | 10/2007 | Hochrainer |
| D557,799 S | 12/2007 | Greenhalgh et al. |
| 7,305,986 B1 | 12/2007 | Steiner et al. |
| 7,306,787 B2 | 12/2007 | Tarara et al. |
| D560,793 S | 1/2008 | Pearl et al. |
| 7,316,748 B2 | 1/2008 | Li et al. |
| 7,331,340 B2 | 2/2008 | Barney |
| 7,334,577 B2 | 2/2008 | Gumaste et al. |
| 7,344,734 B2 | 3/2008 | Heijerman et al. |
| 7,368,102 B2 | 5/2008 | Tarara et al. |
| 7,373,938 B2 | 5/2008 | Nichols et al. |
| 7,377,277 B2 | 5/2008 | Hickey et al. |
| 7,387,122 B2 | 6/2008 | Nishibayashi et al. |
| 7,399,528 B2 | 7/2008 | Caponetti et al. |
| D577,815 S | 9/2008 | Gokhale et al. |
| 7,422,013 B2 | 9/2008 | Burr et al. |
| 7,448,375 B2 | 11/2008 | Gonda et al. |
| 7,448,379 B2 | 11/2008 | Yamashita et al. |
| 7,451,761 B2 | 11/2008 | Hickey et al. |
| D583,463 S | 12/2008 | Wood et al. |
| 7,461,653 B2 | 12/2008 | Oliva |
| 7,462,367 B2 | 12/2008 | Schmidt et al. |
| 7,464,706 B2 | 12/2008 | Steiner et al. |
| 7,469,696 B2 | 12/2008 | Yang et al. |
| 7,500,479 B2 | 3/2009 | Nichols et al. |
| 7,503,324 B2 | 3/2009 | Barney et al. |
| 7,520,278 B2 | 4/2009 | Crowder et al. |
| 7,521,069 B2 | 4/2009 | Patton et al. |
| 7,533,668 B1 | 5/2009 | Widerstrom |
| 7,556,798 B2 | 7/2009 | Edwards et al. |
| 7,559,322 B2 | 7/2009 | Foley et al. |
| 7,625,865 B2 | 12/2009 | Colombo |
| 7,694,676 B2 | 4/2010 | Wachtel |
| 7,913,688 B2 | 3/2011 | Cross |
| 7,954,491 B2 | 6/2011 | Hrkach |
| 8,037,880 B2 | 10/2011 | Zhu et al. |
| 8,037,881 B2 | 10/2011 | Pentafragas |
| 8,047,203 B2 | 11/2011 | Young et al. |
| 8,196,576 B2 | 6/2012 | Kriksunov |
| 8,201,555 B2 | 6/2012 | Chawla |
| 8,227,409 B2 | 7/2012 | Kraft |
| 8,424,518 B2 | 4/2013 | Smutney |
| 8,485,180 B2 | 7/2013 | Smutney |
| 8,499,757 B2 | 8/2013 | Smutney |
| 8,522,775 B2 | 9/2013 | Malhotra et al. |
| 8,539,946 B2 | 9/2013 | Esteve et al. |
| 8,636,001 B2 | 1/2014 | Smutney |
| 8,677,992 B2 | 3/2014 | Villax |
| 2001/0027790 A1 * | 10/2001 | Gieschen et al. ........ 128/203.15 |
| 2002/0053344 A1 | 5/2002 | Davies et al. |
| 2002/0088462 A1 | 7/2002 | Genova et al. |
| 2003/0010794 A1 | 1/2003 | Herdtle et al. |
| 2003/0053960 A1 | 3/2003 | Heijerman et al. |
| 2003/0136405 A1 | 7/2003 | Goede et al. |
| 2003/0235538 A1 | 12/2003 | Zierenberg |
| 2004/0025875 A1 | 2/2004 | Reber et al. |
| 2004/0077528 A1 | 4/2004 | Steiner et al. |
| 2004/0107963 A1 | 6/2004 | Finlay et al. |
| 2004/0151059 A1 | 8/2004 | Roberts, II et al. |
| 2004/0182387 A1 | 9/2004 | Steiner et al. |
| 2004/0187869 A1 | 9/2004 | Bjorndal et al. |
| 2004/0204439 A1 | 10/2004 | Staniforth et al. |
| 2004/0204440 A1 | 10/2004 | Staniforth et al. |
| 2004/0211419 A1 | 10/2004 | Eason et al. |
| 2004/0250812 A1 | 12/2004 | Davies et al. |
| 2005/0000518 A1 | 1/2005 | Dunkley et al. |
| 2005/0022812 A1 * | 2/2005 | Hrkach ............... 128/203.15 |
| 2005/0039743 A1 | 2/2005 | Taylor |
| 2005/0156601 A1 | 7/2005 | Steiner et al. |
| 2005/0183723 A1 | 8/2005 | Pinon et al. |

(56) References Cited

U.S. PATENT DOCUMENTS

| | | | |
|---|---|---|---|
| 2006/0000469 A1 | 1/2006 | Tseng | |
| 2006/0040953 A1 | 2/2006 | Leone-Bay et al. | |
| 2006/0060194 A1 | 3/2006 | Oliva | |
| 2006/0073105 A1 | 4/2006 | Yamashita et al. | |
| 2006/0153778 A1 | 7/2006 | Gelber | |
| 2006/0169280 A1 | 8/2006 | Yamashita et al. | |
| 2006/0219242 A1* | 10/2006 | Zierenberg | 128/200.23 |
| 2006/0239933 A1 | 10/2006 | Nilsson et al. | |
| 2006/0239934 A1* | 10/2006 | Cheatham et al. | 424/46 |
| 2007/0044793 A1 | 3/2007 | Kleinstreuer et al. | |
| 2007/0099454 A1 | 5/2007 | Gordon | |
| 2007/0125375 A1 | 6/2007 | Finlay et al. | |
| 2007/0151562 A1 | 7/2007 | Jones | |
| 2007/0196503 A1 | 8/2007 | Wilson | |
| 2007/0225587 A1 | 9/2007 | Burnell et al. | |
| 2007/0235029 A1 | 10/2007 | Zhu et al. | |
| 2007/0272763 A1 | 11/2007 | Dunne et al. | |
| 2007/0295332 A1 | 12/2007 | Ziegler | |
| 2008/0047550 A2 | 2/2008 | Steiner et al. | |
| 2008/0066739 A1 | 3/2008 | LeMahieu et al. | |
| 2008/0108554 A1 | 5/2008 | Jackson et al. | |
| 2008/0115785 A1 | 5/2008 | Eason et al. | |
| 2008/0127971 A1 | 6/2008 | King et al. | |
| 2008/0127974 A1 | 6/2008 | Lastow | |
| 2008/0168987 A1 | 7/2008 | Denny et al. | |
| 2008/0190424 A1 | 8/2008 | Lucking et al. | |
| 2008/0190425 A1 | 8/2008 | Steiner et al. | |
| 2008/0216824 A1 | 9/2008 | Ooida | |
| 2008/0295833 A1 | 12/2008 | Rohrschneider et al. | |
| 2008/0314384 A1 | 12/2008 | Harris et al. | |
| 2008/0319333 A1 | 12/2008 | Gavish et al. | |
| 2009/0025720 A1 | 1/2009 | Chen | |
| 2009/0068274 A1 | 3/2009 | Edwards et al. | |
| 2009/0084379 A1 | 4/2009 | Goeckner et al. | |
| 2009/0084380 A1 | 4/2009 | Gieschen et al. | |
| 2009/0110647 A1 | 4/2009 | Richardson | |
| 2009/0178676 A1 | 7/2009 | Villax et al. | |
| 2009/0205657 A1 | 8/2009 | Barney et al. | |
| 2009/0209502 A1 | 8/2009 | Haeberlin et al. | |
| 2009/0241949 A1 | 10/2009 | Smutney | |
| 2009/0250058 A1 | 10/2009 | Lastow | |
| 2009/0308391 A1 | 12/2009 | Smutney | |
| 2009/0314291 A1* | 12/2009 | Anderson et al. | 128/203.15 |
| 2010/0012120 A1 | 1/2010 | Herder | |
| 2010/0051027 A1* | 3/2010 | Remmelgas et al. | 128/203.15 |
| 2010/0065048 A1* | 3/2010 | Mueller-Walz et al. | 128/203.15 |
| 2010/0163042 A1 | 7/2010 | Bhowmick et al. | |
| 2010/0180894 A1 | 7/2010 | Jones | |
| 2010/0212667 A1 | 8/2010 | Smith et al. | |
| 2010/0326438 A1 | 12/2010 | Dunne | |
| 2011/0011394 A1 | 1/2011 | Edwards et al. | |
| 2011/0023876 A1* | 2/2011 | Vehring et al. | 128/203.15 |
| 2011/0083667 A1 | 4/2011 | Briant | |
| 2011/0155129 A1* | 6/2011 | Stedman et al. | 128/200.23 |
| 2012/0071510 A1 | 3/2012 | Liu | |
| 2012/0247465 A1 | 10/2012 | Wachtel | |
| 2013/0104887 A1 | 5/2013 | Smutney | |
| 2013/0199527 A1 | 8/2013 | Smutney | |
| 2013/0291866 A1 | 11/2013 | Smutney | |
| 2013/0291867 A1 | 11/2013 | Smutney | |
| 2013/0338065 A1 | 12/2013 | Smutney | |
| 2014/0007873 A1 | 1/2014 | Smutney | |
| 2014/0014106 A1 | 1/2014 | Smutney | |
| 2014/0083421 A1 | 3/2014 | Smutney | |
| 2014/0096771 A1 | 4/2014 | Remmelgas et al. | |

FOREIGN PATENT DOCUMENTS

| | | |
|---|---|---|
| WO | 93/18754 | 9/1993 |
| WO | 94/08552 | 4/1994 |
| WO | 95/00127 | 1/1995 |
| WO | 95/24183 | 9/1995 |
| WO | 96/01105 | 1/1996 |
| WO | 96/36314 | 11/1996 |
| WO | 98/39043 | 9/1998 |
| WO | 99/52506 | 10/1999 |
| WO | 01/68169 | 9/2001 |
| WO | 02/085281 | 10/2002 |
| WO | 02/102444 | 12/2002 |
| WO | 2004/033010 | 4/2004 |
| WO | 2004/035121 | 4/2004 |
| WO | 2004/041338 | 5/2004 |
| WO | 2004/050152 | 6/2004 |
| WO | 2004/060458 | 7/2004 |
| WO | 2005/023348 | 3/2005 |
| WO | 2005/028699 | 3/2005 |
| WO | 2005/089843 | 9/2005 |
| WO | 2005/102429 | 11/2005 |
| WO | 2005/113043 | 12/2005 |
| WO | 2005/120616 | 12/2005 |
| WO | 2006/010248 | 2/2006 |
| WO | 2006/023943 | 3/2006 |
| WO | 2006/037636 | 4/2006 |
| WO | 2006/061637 | 6/2006 |
| WO | 2006/086107 | 8/2006 |
| WO | 2006/090149 | 8/2006 |
| WO | 2006/105501 | 10/2006 |
| WO | 2007/024953 A1 | 3/2007 |
| WO | 2007/033316 | 3/2007 |
| WO | 2007/042822 | 4/2007 |
| WO | 2007/068896 | 6/2007 |
| WO | 2007/093310 | 8/2007 |
| WO | 2007/098500 | 8/2007 |
| WO | 2007/118342 | 10/2007 |
| WO | 2007/121411 | 10/2007 |
| WO | 2007/132217 | 11/2007 |
| WO | 2007/144607 | 12/2007 |
| WO | 2007/144614 | 12/2007 |
| WO | 2008/001744 | 1/2008 |
| WO | 2008/008021 | 1/2008 |
| WO | 2008/020217 | 2/2008 |
| WO | 2008/092864 | 8/2008 |
| WO | 2008/110809 | 9/2008 |
| WO | 2009/005546 | 1/2009 |
| WO | 2009/008001 | 1/2009 |
| WO | 2009/055030 | 4/2009 |
| WO | 2009/055740 | 4/2009 |
| WO | 2009/047281 | 12/2009 |
| WO | 2010/102148 | 9/2010 |
| WO | 2011/163272 | 12/2011 |

OTHER PUBLICATIONS

Edwards et al., Recent advances in pulmonary drug delivery using large, porous inhaled particles. Journal of Applied Physiology, pp. 379-385 (1998).

Ferrin et al, Pulmonary retention of ultrafine and fine particles in rats. Am. J. Repir. Cell Mol. Biol., pp. 535-542 (1992).

Insulin inhalation NN 1998, Drugs R & D, 2004, pp. 46-49, Adis Data Information BV.

Klinger et al., Insulin-micro and nanoparticles for pulmonary delivery. International Journal of Pharmaceutics, vol. 377, pp. 173-179 (2009).

Nemmar et al., Passage of inhaled particles into the blood circulation in humans. Circulation pp. 411-414 (2002).

Newman, Principles of metered-dose inhaler design. Respiratory Care, vol. 50, No. 9, pp. 1177-1190 (2005).

Next Generation Inhaler Nears Market, Manufacturing Chemist, Cambridge Consultants, Polygon Media Ltd. (2006).

Oberdorster et al., Correlation between particle size, in vivo particle persistence, and lung injury. Environ Health Perspect 102 Suppl 5, pp. 173-179 (1994).

Oberdorster et al.,Pulmonary effects of inhaled ultrafine particles. International Archives of Occupational and Environmental Health, vol. 74, pp. 1-8 (2001).

O'Neill, Air pollution and inflammation in type 2 diabetes: a mechanism for susceptibility. Occup Environ Med. vol. 64, pp. 373-379 (2007).

Pesic, Inhaler delivers more drug to the deep lung, says Cambridge Consultants. in-Pharma Technologist.com, http://www/in-pharmatechnologist.com/content/view/print/344335, Dec. 1, 2010.

(56) References Cited

OTHER PUBLICATIONS

Pfutzner, Technosphere/Insulin—A new approach for effective delivery of human insulin via the pulmonary route. Diabetes Technology & Therapeutics, vol. 4, No. 5, pp. 589-594 (2002).
Roumeliotis, New inhaler launched with a bag, in-Pharma Technologist.com, Decision News Media SAS (2006).
Shimada et al. Translocation pathway of the intertracheally instilled ultrafine particles from the lung into the blood circulation in the mouse. Toxicologic Pathology pp. 949-957 (2006).
Svartengren et al., Added External Resistance Reduces Oropharyngeal Deposition and Increases Lung Deposition of Aerosol Particles in Asthmatics. Am. J. Respir. Crit. Care Med., vol. 152, pp. 32-27, 1995.
Telko et al., Dry Powder Inhaler Formulation. Respiratory Care, Sep. 2005, vol. 50, No. 9, pp. 1209-1227.
Vaczek, Accelerating drug delivery firms exploring new drug-delivery routes and devices intently awaiting the commercial launch of Exubera. Pharmaceutical & Medical Packaging News, vol. 14, No. 6 (2006).
File History of Related U.S. Appl. No. 14/092,810, filed Nov. 27, 2013.
File History of Related U.S. Appl. No. 13/921,104, filed Jun. 18, 2013.
File History of Related U.S. Appl. No. 13/941,365, filed Jul. 12, 2013.
CN Office Action cited in application No. 200880122670.3 mailed on Nov. 23, 2011.
International Search Report for PCT/US2010/038287.
"An inhaled insulin formulation (Technosphere Insulin) effectively improves glycaemic control in patients with type 2 diabetes mellitus." Inpharma Weekly, vol. 1522, Jan. 28, 2006, p. 8.
Baso A et al. "Effects of a change in the pattern of insulin delivery on carbohydrate tolerance in diabetic and nondiabetic humans in the presence of differing degrees of insulin resistance." J Clin Invest 97:2351-2361, 1996.
Bayés M et al. "Gateways to clinical trials" Methods Find Exp Clin Pharmacol 24:431-455, 2002.
Belmin J et al. "Novel drug delivery systems for insulin. Clinical potential for use in the elderly." Drugs Aging 20:303-12, 2003.
Boss AH et al. "Insulin bio-effect is limited by speed of absorption and elimination: similarities between an inhaled insulin formulation that mimics first-phase kinetics and i.v. insulin." Diabetologia 47:A314, 2004.
Boss AH et al. "Markedly reduced post prandial glucose excursions through inhaled Technosphere®/Insulin in comparison to SC injected regular insulin in subjects with type 2 diabetes." 1st Annual Meeting of the European Association for the Study of Diabetes, Sep. 2005, abstract 816.
Boss AH et al. "Does kinetics matter? Physiological consequences of the ability of Technosphere®/Insulin inhalation to mimic first phase insulin release." Presented at the 5th Annual Meeting of the Diabetes Technology Society, Nov. 2005, abstract A14.
Boss AH et al. "Mimicry of the early phase insulin response in humans with rapidly available inhaled insulin accelerates post prandial glucose disposal compared to slower bioavailable insulin." Presented at the American Diabetes Association 65th Scientific Sessions, Jun. 2005, abstract 1373-P.
Boss AH et al. "Inhaled Technosphere®/Insulin: Glucose elimination at the right time?" Poster presented at the American Diabetes Association 65th Scientific Sessions, Jun. 2005, abstract 443-P.
Boss AH et al. "The variability and time-action profile of inhaled Technosphere®/Insulin compares favorably to that of subcutaneous human regular insulin." Presented at the American Diabetes Association 65th Scientific Sessions, Jun. 2005, abstract 358-OR.
Brownlee M et al. "Glycemic variability: a hemoglobin A1c-independent risk factor for diabetic complications." JAMA 295:1707-8, 2006.
Caumo et al. "First-phase insulin secretion: does it exist in real life" Considerations on shape and function. Am J Physiol Endocrinol Metab 287:E371-E385, 2004.
Cefalu "Concept, strategies and feasibility of noninvasive insulin delivery." Diabetes Care 27:239-246, 2004.
Cefalu "Novel routes of insulin delivery for patients with type 1 or type 2 diabetes." Ann Med 33:579-586, 2001.
Cerasi et al. Decreased sensitivity of the pancreatic beta cells to glucose in prediabetic and diabetic subjects. A glucose dose-response study. Diabetes 21(4):224-34, 1972.
Cernea et al. "Dose-response relationship of oral insulin spray in healthy subjects." Diabetes Care 28:1353-1357, 2005.
Cheatham et al. "Desirable dynamics and performance of inhaled insulin compared to subcutaneous insulin given at mealtime in type 2 diabetes: A report from the Technosphere®/Insulin study group." Diabetes Tech Ther 6:234-235, 2004.
Cheatham et al. "A novel pulmonary insulin formulation replicates first phase insulin release and reduces s-proinsulin levels." Presented at the American Diabetes Association 64th Scientific Sessions, Jun. 2004, abstract 457-P.
Cheatham et al. "Prandial Technosphere®/Insulin inhalation provides significantly better control of meal-related glucose excursions than prandial subcutaneous insulin." Presented at the Diabetes Technology Society meeting, Oct. 2004.
Del Prato "Unlocking the opportunity of tight glycaemic control. Far from goal." Diabetes Obesity Metabolism 7:S1-S4, 2005.
Edelman SV Type II diabetes mellitus. Adv Int Med 43:449-500, 1998.
Gates BJ "Update on advances in alternative insulin therapy." Advances in Pharmacy 1:159-168, 2003.
Grant et al "Both insulin sensitivity and maximal glucose elimination rate are reduced in type 2 diabetes." Presented at the American Diabetes Association 65th Scientific Sessions, Jun. 2005, abstract 2202-PO.
Grant et al. "The distribution of 14C-labeled particles following intra-tracheal liquid installation in the Sprague-Dawley rat." Presented at the American Diabetes Association 64th Scientific Sessions, Jun. 2004, abstract 461-P.
Gupta et al. Contemporary approaches in aerosolized drug delivery to the lung. J Controlled Release 17:129-148, 1991.
Harsch IA "Inhaled Insulins: Their potential in the treatment of diabetes mellitus." Treat Endocrinol 4:131-138, 2005.
Heinemann, L., et al., "Current status of the development of inhaled insulin" Br. Diabetes Vasc Dis 4:295-301, 2004.
Hirsch IB "Insulin analogues." N Engl J Med 352:174-83, 2005.
Kapitza et al. "Dose-response characteristics for a new pulmonary insulin formulation and inhaler." Presented at the 35th Annual Meeting of the EASD, Sep. 2000, abstract OP29 184.
Kohler et al. Non-radioactive approach for measuring lung permeability: inhalation of insulin. Atemw Lungenkrkh 13:230-232, 1987.
Krueger et al. "Toxicological profile of pulmonary drug delivery agent." Presented at the American Diabetes Association 64th Scientific Sessions, Jun. 2004, abstract 465-P.
Laureano et al. "Rapid absorption and elimination of insulin from the lung following pulmonary administration of Technosphere®/Insulin: A pharmacokinetic study in a rat model." Presented at the American Diabetes Association 65th Scientific Sessions, Jun. 2005, abstract 445-P.
Leahy et al. Beta-cell dysfunction in type II diabetes mellitus. Curr Opin Endocrinol Diabetes 2:300-306, 1995.
Leiner et al. "The pharmacokinetic profile of insulin administered by inhalation in the rat." Diabetes 53 Supplement, Jun. 2004, A111.
Leiner et al. "Particles facilitate the absorption of insulin in a primary cell culture model of alveolar epithelium without evidence of cytotoxicity." Presented at the American Diabetes Association 64th Scientific Sessions, Jun. 2004, abstract 467-P.
Lian et al. A self-complementary self-assembling microsphere system: application for intravenous delivery of the antiepileptic andneuroprotectant compound felbanate. J Pharm Sci 89:867-875, 2000.
Lindner et al. "Increase in serum insulin levels is correlated with lung distribution after pulmonary delivery of Technosphere/Insulin." Diabetologia 46:A277, 2003.
Mandal "Inhaled insulin for diabetes mellitus." Am J Health Sys Pharm 62:1359-64, 2005.

(56) References Cited

OTHER PUBLICATIONS

Mann "Pulmonary insulin—the future of prandial insulin therapy." Presented at the 5th Annual Meeting of the Diabetes Technology Society, Nov. 2005, abstract A94.
Monnier et al. "Activation of oxidative stress by acute glucose fluctuations compared with sustained chronic hyperglycemia in patients with type 2 diabetes." JAMA 295:1681-7, 2006.
Nathan et al. "Intensive diabetes treatment and cardiovascular disease in patients with type 1 diabetes." N Engl J Med 353:2643-53, 2005.
Owens et al. "Alternative routes of insulin delivery." Diabetic Medicine 20:886-898, 2003.
Patton et al. "Clinical pharmacokinetics and pharmacodynamics of inhaled insulin." Clin Pharmacokinet 43:781-801, 2004.
Peyrot et al. "Resistance to insulin therapy among patients and providers." Diabetes Care 28:2673-2679, 2005.
Pfeiffer et al. Insulin secretion in diabetes mellitus. Am J Med 70:579-88, 1981.
Pfützner A. et al. "Influence of small dose i.v., s.c. and pulmonary insulin treatment on prandial glucose control in patients with Type 2 diabetes." 37th Annual Meeting of the EASD, Sep. 9-13, 2001, abstract 812.
Pfützner A et al. "Variability of insulin absorption after subcutaneous and pulmonary application in patients with type 2 diabetes." Diabetes 51 Supplement, Jun. 2002, A47-48.
Pfützner A et al. Pilot study with Technosphere/PTH(1-34)—a new approach for effective pulmonary delivery of parathyroid hormone (1-34). Horm Metab Res 35:319-323, 2003.
Pfützner A et al. "Lung distribution of radiolabeled Technosphere™/Insulin." Diabetes 52 Supplement, Jun. 2003, A107.
Katchalski, Ephraim, "Synthesis of Lysine Anhydride", J. Amer. Chem. Soc., vol. 68, 1946, pp. 879-880.
Kopple, Kenneth D., "A Convenient Synthesis of 2.,5-Piperazinediones", J. Org. Chem., vol. 33, No. 2, 1968, pp. 862-864.
Pfutzner et al. "Pulmonary Insulin Delivery by Means of the Technosphere Drug Carrier Mechanism." Expert Opin Drug Deliv 2:1097-1106, 2005.
Pfutzner et al. "Inhaled Technosphere/Insulin Shows a Low Variability in Metabolic Action in Type 2 Diabetic Patients." Diabetes 49 Supplement, May 2000, A121.
Polonsky et al. "Abnormal Patterns of Insulin Secretion in Non-insulin-Dependent Diabetes Mellitus." N Eng J Med 318:1231-39, 1988.
Raskin et al. "Continuous Subcutaneous Insulin Infusion and Multiple Daily Injection Therapy are Equally Effective in Type 2 Diabetes."Diabetes Care 26:2598-2603, 2003.
Rave et al. "Results of a Dose-Response Study with a New Pulmonary Insulin Formulation and Inhaler." Diabetes 49, Supplement, May 2000, A75.
Rave et al. "Dose Response of Inhaled Dry-Powder Insulin and Dose Equivalence to Subcutaneous Insulin Lispro." Diabetes Care 28:2400-2405, 2005.
Raz et al. "Pharmacodynamics and Pharmacokinetics of Dose Ranging Effects of Oralin Versis S.S. Regular Insulin in Type 1 Diabetic Subjects." Fourth Annual Diabetes Technology Meeting, Philadelphia, 2004.
Rhodes et al. "Technosphere: Microspherical Particles from Substituted Diketopiperazines for Use in Oral Drug Delivery." 208th ACS National Meeting, Aug. 1994.
Rosenstock et al. "Inhaled Insulin Improves Glycemic Control when Substituted for or Added to Oral Combination Therapy in Type 2 Diabetes." Ann Intern Med 143:549-558, 2005.
Rousseau et al. "Drug delivery by fumaryl diketopiperazine particles: evidence for passive transport." Presented at the American Diabetes Association 64th Scientific Sessions, Jun. 2004, abstract 484-P.
Sakagami et al. "Respirable microspheres for inhalation: the potential of manipulating pulmonary disposition for improved therapeutic efficacy." Clin Pharmacokinet 44:263-77, 2005.
Skyler JS et al. "Use of inhaled insulin in a basal/bolus insulin regimen in type 1 diabetic subjects." Diabetes Care 28:1630-1635, 2005.
Steiner et al. "Technosphere®, a novel drug delivery system for oral administration of calcitonin." Pharmaceutical Res 11:S299, 1994.
Steiner et al. "A novel glucagon delivery system for the management of hyperinsulinemia." Diabetes 49 Supplement, May 2000, A368.
Steiner et al. "Bioavailability and pharmacokinetic properties of inhaled dry powder Technosphere®/Insulin." Diabetes 49 Supplement, May 2000, A126.
Steiner et al. Technosphere(TM)/Insulin—proof of concept study with a new insulin formulation for pulmonary delivery. Exp Clin Endocrinol Diabetes 110:17-21, 2002.
Taylor et al. "Aerosols for macromolecule delivery. Design challenges and solutions." Am J Drug Deliv 2:143-155, 2004.
Warren et al. "Postprandial versus prandial dosing of biphasic insulin aspart in elderly type 2 diabetes patients." Diabetes Res Clin Pract 66:23-29, 2004.
White JR et al. "Inhaled insulin: an overview." Clinical Diabetes 19:13-16, 2001.
Kaur et al., A delineation of diketopiperazine self-assembly processes: understanding the molecular events involved in N $N^\alpha$e e-(Fumaroyl) diketopiperazine of L-Lys (FDKP) Interactions. Molecular Pharmaceutics, vol. 5, No. 2, pp. 294-315 (2008).
Coors et al., Polysorbate 80 in medical products and nonimmunologic anaphylactoid reactions. Ann. Allergy Asthma Immunol., 95(6): 593-599 (2005). Abstract only. Accessed by Examiner on Jul. 22, 2013 and cited in Office Action issued on Jul. 26, 2013 in U.S. Appl. No. 12/830,557.
Non-covalent interactions from UCDavis ChemWiki, pp. 1-5. Accessed by Examiner on Jul. 23, 2013 and cited in Office Action issued on Jul. 26, 2013 in U.S. Appl. No. 12/830,557.
Definition of analog from http://cancerweb.ncl.ac.uk/omd/about.html, pp. 1-5. Accessed by Examiner on Jul. 7, 2005 and cited in Office Action issued on Jul. 26, 2013 in U.S. Appl. No. 12/830,557.

\* cited by examiner

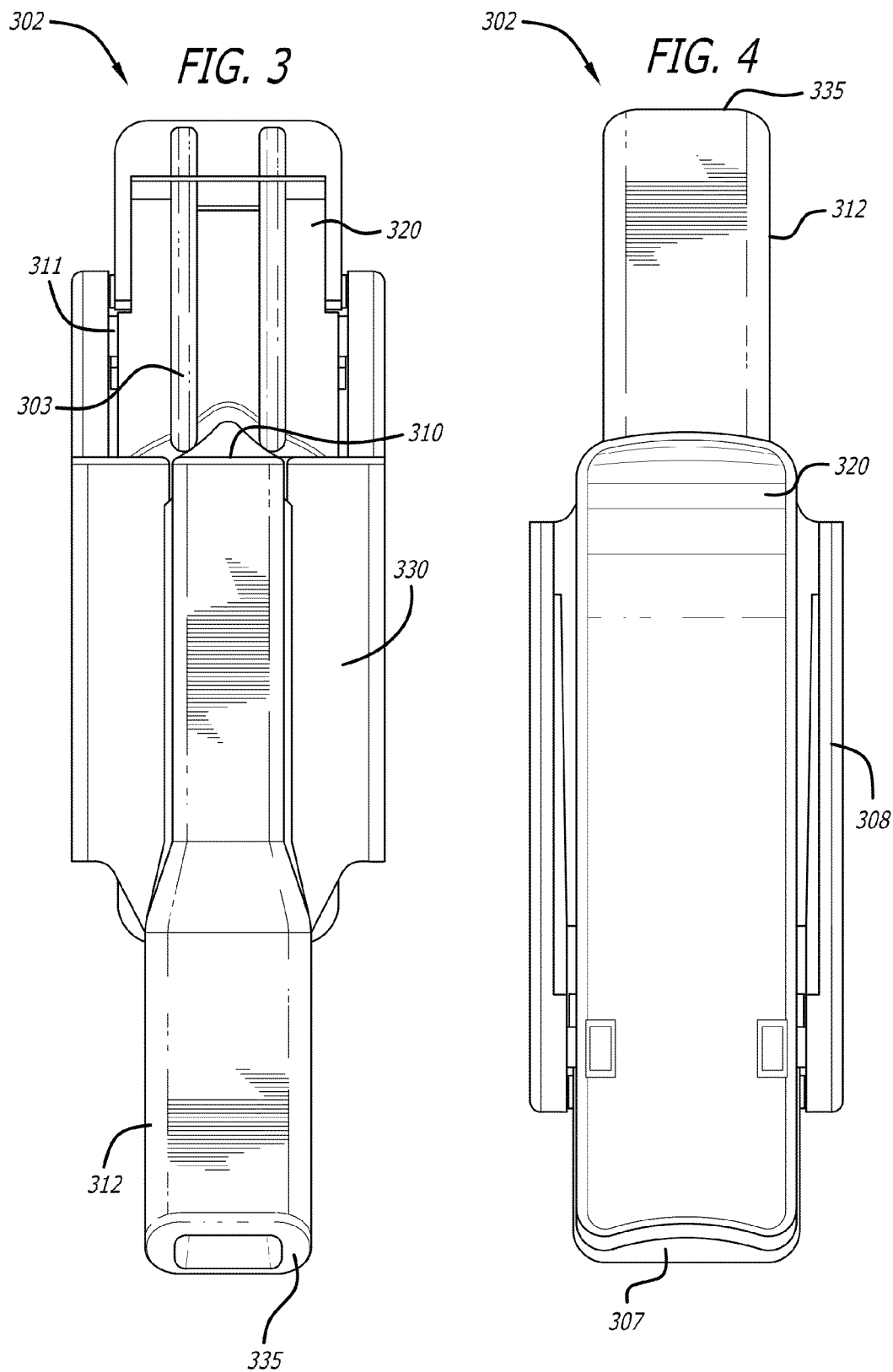

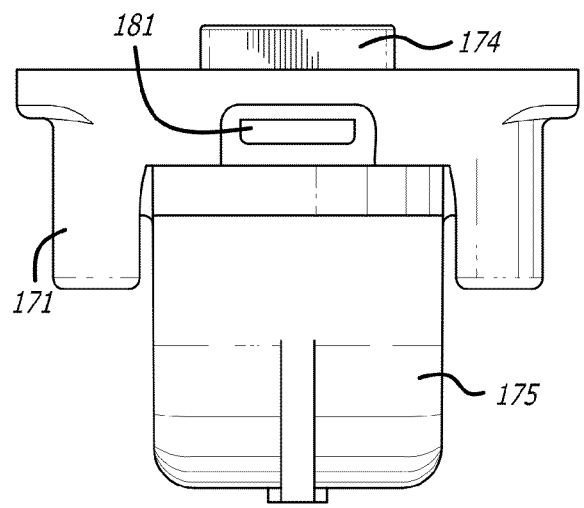
FIG. 25
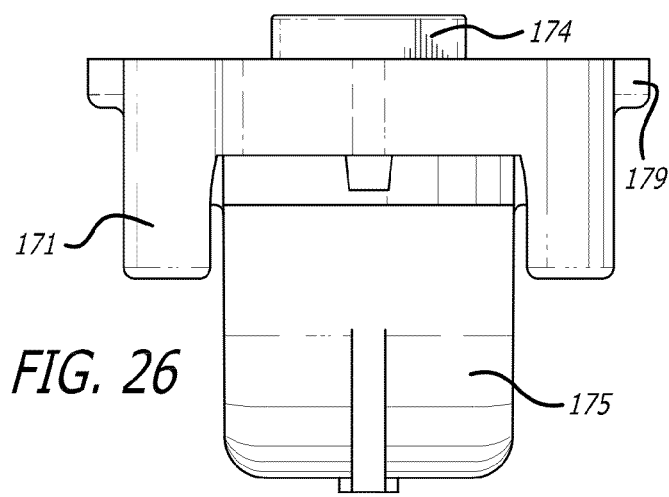
FIG. 26
FIG. 27
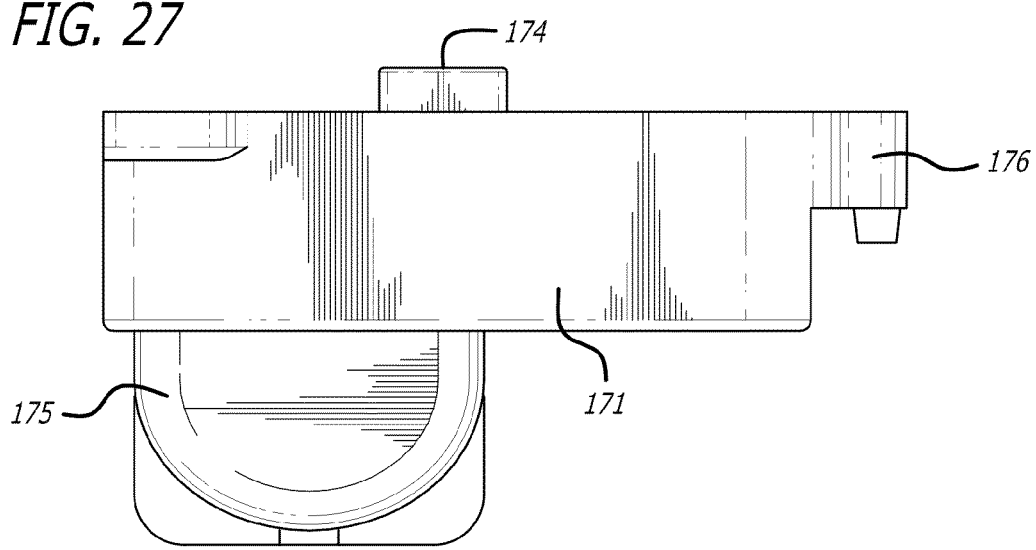

DRY POWDER DRUG DELIVERY SYSTEM AND METHODS

CROSS REFERENCE TO RELATED APPLICATIONS

This application is an application under 35 U.S.C. §371 of International Patent Application PCT/US2011/041303 filed on Jun. 21, 2011 which claims the benefit of U.S. provisional patent application No. 61/411,775, filed on Nov. 9, 2010 and U.S. Provisional Patent Application 61/357,039, filed Jun. 21, 2010, the disclosures each of which are incorporated herein by reference in their entirety.

This application is a continuation-in-part of U.S. patent application Ser. No. 12/717,884, filed Mar. 4, 2010 which claims the benefit of U.S. Provisional Patent Application Ser. Nos. 61/222,810 filed Jul. 2, 2009 and 61/258,184 filed Nov. 4, 2009, and is a continuation-in-part of U.S. patent application Ser. No. 12/484,137, filed Jun. 12, 2009 which claims the benefit of U.S. Provisional Patent Application Ser. Nos. 61/157,506, filed Mar. 4, 2009, and 61/061,551, filed on Jun. 13, 2008, the disclosures each of which are incorporated herein by reference in their entirety.

TECHNICAL FIELD

The present disclosure relates to dry powder inhalation system including dry powder inhalers, cartridges and pharmaceutical compositions for delivering drug to the pulmonary tract and pulmonary circulation for the treatment of disease or disorder.

BACKGROUND

Drug delivery systems for disease treatment which introduce active ingredients into the circulation are numerous and include oral, transdermal, inhalation, subcutaneous and intravenous administration. Drugs delivered by inhalation are typically delivered using positive pressure relative to atmospheric pressure in air with propellants. Such drug delivery systems deliver drugs as aerosols, nebulized or vaporized. More recently, drug delivery to lung tissue has been achieved with dry powder inhalers. Dry powder inhalers can be breath activated or breath-powered and can deliver drugs by converting drug particles in a carrier into a fine dry powder which is entrained into an air flow and inhaled by the patient. Drugs delivered with the use of a dry powder inhaler are no longer only intended to treat pulmonary disease, but can also be absorbed into the systemic circulation so they can be used to treat many conditions, including, but not limited to diabetes and obesity.

Dry powder inhalers, used to deliver medicaments to the lungs, contain a dose system of a powder formulation usually either in bulk supply or quantified into individual doses stored in unit dose compartments, like hard gelatin capsules or blister packs. Bulk containers are equipped with a measuring system operated by the patient in order to isolate a single dose from the powder immediately before inhalation. Dosing reproducibility requires that the drug formulation is uniform and that the dose can be delivered to the patient with consistent and reproducible results. Therefore, the dosing system ideally operates to completely discharge all of the formulation effectively during an inspiratory maneuver when the patient is taking his/her dose. However, complete discharge is not generally required as long as reproducible dosing can be achieved. Flow properties of the powder formulation, and long term physical and mechanical stability in this respect, are more critical for bulk containers than they are for single unit dose compartments. Good moisture protection can be achieved more easily for unit dose compartments such as blisters. However, materials used to manufacture blisters allow air into the drug compartment and subsequently formulations can lose viability with long storage. Additionally, dry powder inhalers which use blisters to deliver a medicament by inhalation can suffer with inconsistency of dose delivery to the lungs due to variations in the air conduit architecture resulting from puncturing films or peeling films of the blisters.

Dry powder inhalers in the art can generate drug particles or suitable inhalation plumes during an inspiratory maneuver by deagglomerating the powder formulation within a cartridge or capsule. The amount of fine powder discharged from the inhaler's mouthpiece during inhalation is largely dependent on, for example, interparticulate forces in the powder formulation and efficiency of the inhaler to separate those particles so that they are suitable for inhalation. The benefits of delivering drugs via the pulmonary circulation are numerous and can include rapid entry into the arterial circulation, avoidance of drug degradation by liver metabolism, ease of use, i.e., lack of discomfort of administration by other routes of administration.

Dry powder inhaler products developed for pulmonary delivery have met with limited success to date, due to lack of practicality and/or cost of manufacture. Some of the persistent problems observed with prior art inhalers, include lack of ruggedness of device, inconsistency in dosing, inconvenience of the equipment, poor deagglomeration, problems with delivery in light of divorce from propellant use, and/or lack of patient compliance. Therefore, the inventors have identified the need to design and manufacture an inhaler with consistent powder delivery properties, easy to use without discomfort, and discrete inhaler configurations which would allow for better patient compliance.

SUMMARY

Described herein generally are dry powder inhalation systems for pulmonary delivery, wherein the systems include dry powder inhalers and containers including cartridges for dry powder inhalers for rapid and effective delivery of dry powder formulations to the pulmonary tract. The dry powder formulations of the inhalation systems comprise active agents for the treatment of one or more disease, including, local or systemic diseases or disorders, including, but not limited to diabetes, obesity, pain, headaches such as migraines, central or peripheral nervous system and immune disorders and the like, as well as for delivery of a vaccine formulation. The dry powder inhalers can be breath-powered, compact, reusable or disposable systems, which can have various shapes and sizes, and comprise a system of airflow conduit pathways for the effective and rapid delivery of dry powder medicaments. In one embodiment, the inhaler can be a unit dose, reusable or disposable inhaler that can be used with or without a cartridge. By use without a cartridge we refer to systems in which cartridge-like structures are provided that are integral to the inhaler and the inhaler is for a single use and disposable. Alternatively, in some embodiments, the systems comprise a cartridge which is provided separately and installed in the inhaler for use by, for example, the user. In this embodiment, the inhaler can be a reusable inhaler and a new cartridge is installed in the inhaler at every use. In another embodiment, the inhaler can be a multidose inhaler, disposable or reusable, that can be used with single unit dose cartridges installed in the inhaler or cartridge-like structures built-in or structurally configured as part of the inhaler.

In further embodiments, the dry powder inhalation system comprises a dry powder inhalation device or inhaler with or without a cartridge, and a pharmaceutical formulation comprising an active ingredient for pulmonary delivery. In some embodiments, powder delivery is to the deep lung, including, to the alveolar region, and in some of these embodiments, the active agents is absorbed into the pulmonary circulation for systemic delivery. The system can also comprise a dry powder inhaler with or without a unit dose cartridge, and a drug delivery formulation comprising, for example, a diketopiperazine and an active ingredient such as small molecules, peptides, polypeptides and proteins, including insulin and glucagon-like peptide 1.

In one embodiment, the dry powder inhaler comprises a housing, a moveable member, and a mouthpiece, wherein the moveable member is operably configured to move a container from a powder containment position to a dosing position. In this and other embodiments, the moveable member can be a sled, a slide tray or a carriage which is moveable by various mechanisms.

In another embodiment, the dry powder inhaler comprises a housing and a mouthpiece, structurally configured to have an open position, a closed position and a mechanism operably configured to receive, hold, and reconfigure a cartridge from a containment position to a dispensing, dosing or dose delivery position upon movement of the inhaler from the open position to the closed position. In versions of this embodiment, the mechanism can also reconfigure a cartridge installed in the inhaler from the dosing position to an alternate position after use when the inhaler is opened to unload a used cartridge, thereby indicating to a user that the cartridge has been spent. In one embodiment, the mechanism can reconfigure a cartridge to a disposable or discarding configuration after use. In such embodiments, the housing is structurally configured to be moveably attached to the mouthpiece by various mechanisms including, a hinge. The mechanism configured to receive and reconfigure a cartridge installed in the inhaler from a containment position to the dosing position can be designed to operate manually or automatically upon movement of the inhaler components, for example, by closing the device from an open configuration. In one embodiment, the mechanism for reconfiguring a cartridge comprises a slide tray or sled attached to the mouthpiece and movably attached to the housing. In another embodiment, the mechanism is mounted or adapted to the inhaler and comprises a geared mechanism integrally mounted within, for example, a hinge of the inhaler device. In yet another embodiment, the mechanism operably configured to receive and reconfigure the cartridge from a containment position to a dosing position comprises a cam that can reconfigure the cartridge upon rotation of, for example, the housing or the mouthpiece.

In an alternate embodiment, the dry powder inhaler can be made as a single use, unit dose disposable inhaler, which can be provided with a container configured to hold a powder medicament and the container is moveable from a containment configuration to a dosing configuration by a user, wherein the inhaler can have a first and a second configuration in which the first configuration is a containment configuration and the second configuration is a dosing of dispensing configuration. In this embodiment, the inhaler can be provided with or without a mechanism for reconfiguring the powder container. According to aspects of the latter embodiment, the container can be reconfigured directly by the user. In some aspects of this embodiment, the inhaler and container can be manufactured as a two piece inhalation system wherein the powder medicament is provided to the container prior to assembling the device in a containment configuration. In this embodiment, the container is attached to the inhaler body and is moveable from the containment configuration to a dosing configuration, for example, by sliding relative to the top portion of the inhaler comprising a mouthpiece.

In yet another embodiment, an inhaler comprising a container mounting area configured to receive a container, and a mouthpiece having at least two inlet apertures and at least one exit aperture; wherein one inlet aperture of the at least two inlet apertures is in fluid communication with the container area, and one of the at least two inlet apertures is in fluid communication with the at least one exit aperture via a flow path configured to bypass the container area.

In one embodiment, the inhaler has opposing ends such as a proximal end for contacting a user's lips or mouth and a distal end, and comprises a mouthpiece and a medicament container; wherein the mouthpiece comprises a top surface and a bottom or undersurface. The mouthpiece undersurface has a first area configured relatively flat to maintain a container in a sealed or containment configuration, and a second area adjacent to the first area which is raised relative to the first area. In this embodiment, the container is movable from the containment configuration to the dosing configuration and vice versa, and in the dosing configuration, the second raised area of the mouthpiece undersurface and the container form or define an air inlet passageway to allow ambient air to enter the internal volume of the container or expose the interior of the container to ambient air. In one embodiment, the mouthpiece can have a plurality of openings, for example, an inlet port, an outlet port and at least one port for communicating with a medicament container in a dispensing or dosing position, and can be configured to have integrally attached panels extending from the bottom surface sides of the inhaler and having flanges protruding towards the center of the inhaler mouthpiece, which serve as tracks and support for the container on the mouthpiece so that the container can move along the tracks from the containment position to a dispensing or dosing position and back to containment if desired. In one embodiment, the medicament container is configured with wing-like projections or winglets extending from its top border to adapt to the flanges on the mouthpiece panels. In one embodiment, the medicament container can be moved manually by a user from containment position to a dosing position and back to the containment position after dosing, or by way of a sled, a slide tray, or a carriage.

In another embodiment, a single use, unit dose, disposable inhaler can be constructed to have a sled incorporated and operably configured to the mouthpiece. In this embodiment, a bridge on the sled can abut or rest on an area of the medicament container to move the container along the mouthpiece panel tracks from the containment position to the dispensing or dosing position. In this embodiment, the sled can be operated manually to move the container on the mouthpiece tracks.

In one embodiment, the dry powder inhaler comprises one or more air inlets and one or more air outlets. When the inhaler is closed, at least one air inlet can permit flow to enter the inhaler and at least one air inlet allows flow to enter a cartridge compartment or the interior of the cartridge or container adapted for inhalation. In one embodiment, the inhaler has an opening structurally configured to communicate with the cartridge placement area and with a cartridge inlet port when the cartridge container is in a dosing position. Flow entering the cartridge interior can exit the cartridge through an exit or dispensing port or ports; or flow entering the container of an inhaler can exit through at least one of the dispensing apertures. In this embodiment, the cartridge inlet port or ports is/are structurally configured so that all, or a portion of the air flow entering the interior of the cartridge is directed at the exit or dispensing port or ports.

The medicament container is structurally configured to have two opposing, relatively curvilinear sides which can direct airflow. In this embodiment, flow entering the air inlet during an inhalation can circulate within the interior of the container about an axis relatively perpendicular to the axis of the dispensing ports, and thereby, the flow can lift, tumble and effectively fluidize a powder medicament contained in the cartridge. In this and other embodiments, fluidized powder in the air conduit can be further deagglomerated into finer powder particles by a change in direction or velocity, i.e., acceleration or deceleration of the particles in the flow pathway. In certain embodiments, the change in acceleration or deceleration can be accomplished by changing the angle and geometries of, for example, the dispensing port or ports, the mouthpiece conduit and/or its interfaces. In the inhalers described herewith, the mechanism of fluidization and acceleration of particles as they travel through the inhaler are methods by which deagglomeration and delivery of a dry powder formulation is effectuated.

In particular embodiments, a method for deagglomerating and dispersing a dry powder formulation comprises one or more steps such as tumbling within a primary container region started and enhanced by flow entering the container; a rapid acceleration of powder in the flow through the dispensing ports leaving the container; further accelerating the powder induced by a change in direction or velocity as the powder exits the dispensing port; shearing of powder particles caught within a flow gradient, wherein the flow on the top of the particle is faster than flow on bottom of the particle; deceleration of flow due to expansion of cross-sectional area within the mouthpiece air conduit; expansion of air trapped within a particle due to the particle moving from a higher pressure region to a lower pressure region, or collisions between particles and flow conduit walls at any point in the flow passageways.

In another embodiment, a dry powder inhaler comprises a mouthpiece; a sled, slide tray, or a carriage; a housing, a hinge, and a gear mechanism configured to effectuate movement of the sled or slide tray; wherein the mouthpiece and the housing are moveably attached by the hinge.

Cartridges for use with the dry powder inhaler can be manufactured to contain any dry powder medicament for inhalation. In one embodiment, the cartridge is structurally configured to be adaptable to a particular dry powder inhaler and can be made of any size and shape, depending on the size and shape of the inhaler to be used with, for example, if the inhaler has a mechanism which allows for translational movement or for rotational movement. In one embodiment, the cartridge can be configured with a securing mechanism, for example, having a beveled edge on the cartridge top corresponding to a matching beveled edge in an inhaler so that the cartridge is secured in use. In one embodiment, the cartridge comprises a container and a lid or cover, wherein the container can be adapted to a surface of the lid and can be movable relative to the lid or the lid can be movable on the container and can attain various configurations depending on its position, for example, a containment configuration, a dosing configuration or after use configuration. Alternatively the lid can be removable.

An exemplary embodiment can comprise an enclosure to hold medicament configured having at least one inlet aperture to allow flow into the enclosure; at least one dispensing aperture to allow flow out of the enclosure; the inlet aperture configured to direct at least a portion of the flow at the dispensing aperture or at the particles approaching the dispensing aperture within the enclosure in response to a pressure gradient. The dispensing aperture or apertures and the intake gas aperture each independently can have a shape such as oblong, rectangular, circular, triangular, square and oval-shaped and can be in close proximity to one another. During inhalation, a cartridge adapted to the inhaler in a dosing position allows airflow to enter the enclosure and mix with the powder to fluidize the medicament. The fluidized medicament moves within the enclosure such that medicament gradually exits the enclosure through the dispensing aperture, wherein the fluidized medicament exiting the dispensing aperture is sheared and diluted by a secondary flow not originating from within the enclosure. In one embodiment, the flow of air in the internal volume rotates in a circular manner so as to lift a powder medicament in the container or enclosure and recirculate the entrained powder particles or powder mass in the internal volume of the container promoting the flow to tumble prior to the particles exiting dispensing ports of the container or one or more of the inhaler inlet ports or air outlet or dispensing apertures, and wherein the recirculating flow, can cause tumbling, or non-vortical flow of air in the internal volume acts to deagglomerate the medicament. In one embodiment, the axis of rotation is mostly perpendicular to gravity. In another embodiment the axis of rotation is mostly parallel to gravity. The secondary flow not originating from within the enclosure further acts to de-agglomerate the medicament. In this embodiment, the pressure differential is created by the user's inspiration. A cartridge for a dry powder inhaler, comprising: an enclosure configured to hold a medicament; at least one inlet port to allow flow into the enclosure, and at least one dispensing port to allow flow out of the enclosure; the at least one inlet port is configured to direct at least a portion of the flow entering the at least one inlet port at the at least one dispensing port within the enclosure in response to a pressure differential.

A unit dose cartridge for an inhaler comprising: a substantially flat cartridge top, arrow-like in configuration, having one or more inlet apertures, one or more dispensing apertures, and two side panels extending downwardly and each of the two side panels having a track; and a container moveably engaged to the track of the side panels of the cartridge top, and comprising a chamber configured to have a relatively cup-like shape with two relatively flat and parallel sides and a relatively rounded bottom, and interior surface defining an internal volume; the container configurable to attain a containment position and a dosing position with the cartridge top; wherein in use with a dry powder inhaler during an inhalation a flow entering the internal volume diverges as it enters the internal volume with a portion of the flow exiting through the one or more dispensing apertures and a portion of the flow rotating inside the internal volume and lifting a powder in the internal volume before exiting through the dispensing apertures.

In one embodiment, an inhalation system for pulmonary drug delivery is provided, comprising: a dry powder inhaler comprising a housing and a mouthpiece having an inlet and an outlet port, an air conduit between the inlet and the outlet, and an opening structurally configured to receive a cartridge; a cartridge mounting mechanism such as a sled; a cartridge configured to be adapted to the dry powder inhaler and containing a dry powder medicament for inhalation; wherein the cartridge comprises a container and a lid having one or more inlet ports or one or more dispensing ports; the dry powder inhaler system in use has a predetermined airflow balance distribution through the cartridge relative to total flow delivered to the patient.

In embodiments disclosed herewith, the dry powder inhaler system comprises a predetermined mass flow balance within the inhaler. For example, a flow balance of approximately 20% to 70% of the total flow exiting the inhaler and into the patient is delivered by the dispensing ports or passed through the cartridge, whereas approximately 30% to 80% is generated from other conduits of the inhaler. Moreover, bypass flow or flow not entering and exiting the cartridge can recombine with the flow exiting the dispensing port of the cartridge within the inhaler to dilute, accelerate and ultimately deagglomerate the fluidized powder prior to exiting the mouthpiece.

In the embodiments described herein, the dry powder inhaler is provided with relatively rigid air conduits or plumbing system and high flow resistance levels to maximize deagglomeration of powder medicament and facilitate delivery. Inhalation systems disclosed herein comprise conduits which exhibit resistance to flow in use maintaining low flow rates which minimize high inertial forces on powder particles discharged from the inhaler, preventing throat deposition or impaction of the powder particles in the upper respiratory tract, and thereby, maximizing powder particle deposition in the lungs. Accordingly, the present inhalation systems provide effective and consistent powder medicament discharge from the inhalers after repeated use since the inhalers are provided with air conduit geometries which remain the constant and cannot be altered. In some embodiments, the dry powder medicament is dispensed with consistency from an inhaler in less than about 3 seconds, or generally less than one second. In some embodiments, the inhaler system can have a high resistance value of, for example, approximately 0.065 to about 0.200 ($\sqrt{kPa}$)/liter per minute. Therefore, in the inhalation systems, peak inhalation pressures drop offs between 2 and 20 kPa produce resultant peak flow rates of about between 7 and 70 liters per minute. These flow rates result in greater than 75% of the cartridge contents dispensed in fill masses between 1 and 30 mg or greater. In some embodiments, these performance characteristics are achieved by end users within a single inhalation maneuver to produce cartridge dispense percentages greater than 90%. In certain embodiments, the inhaler and cartridge system are configured to provide a single dose by discharging powder from the inhaler as a continuous flow of powder delivered to a patient.

In one embodiment, a method for effectively deagglomerating a dry powder formulation during an inhalation in a dry powder inhaler is provided. The method can comprise the steps of providing a dry powder inhaler comprising a container having an air inlet, dispensing ports communicating with a mouthpiece air conduit and containing and delivering a formulation to a subject in need of the formulation; generating an airflow in the inhaler by the subject's inspiration so that about 20 to about 70% of the airflow entering the inhaler enters and exits the container; allowing the airflow to enter the container inlet, circulate and tumble the formulation in an axis perpendicular to the dispensing ports to fluidize the formulation so as to yield a fluidized formulation; accelerating metered amounts of fluidized formulation through the dispensing ports and in the air conduit, and decelerating the airflow containing fluidized formulation in the mouthpiece air conduit of the inhaler prior to reaching the subject. In some specific embodiments, 20% to 60% of the total flow through the inhaler goes through the cartridge during dose delivery.

In another embodiment, a method for deagglomerating and dispersing a dry powder formulation for inhalation is provided, comprising the steps of: generating an airflow in a dry powder inhaler comprising a mouthpiece and a container having at least one inlet port and at least one dispensing port and containing a dry powder formulation; the container forming an air passage between at least one inlet port and at least one dispensing port and the inlet port directs a portion of the airflow entering the container to at least one dispensing port; allowing airflow to tumble powder within the container in a substantially perpendicular axis to the at least one dispensing port so as to lift and mix the dry powder medicament in the container to form an airflow medicament mixture; and accelerating the airflow exiting the container through at least one dispensing port. In one embodiment, the inhaler mouthpiece is configured to have a gradual expanding cross-section to decelerate flow and minimize powder deposition inside the inhaler and promote maximal delivery of powder to the patient. In one embodiment, for example, the cross-sectional area of the oral placement region of an inhaler can be from about 0.05 $cm^2$ to about 0.25 $cm^2$ over an approximate length of about 3 cm. These dimensions depend on the type of powder used with the inhaler and the dimensions of the inhaler itself.

In one embodiment, a cartridge for a dry powder inhaler is provided, comprising: a cartridge top and a container defining an internal volume; wherein the cartridge top has an undersurface that extends over the container; the undersurface configured to engage the container, and comprising an area to contain the internal volume and an area to expose the internal volume to ambient air.

In an alternate embodiment, a method for the delivery of particles through a dry powder delivery device is provided, comprising: inserting into the delivery device a cartridge for the containment and dispensing of particles comprising an enclosure enclosing the particles, a dispensing aperture and an intake gas aperture; wherein the enclosure, the dispensing aperture, and the intake gas aperture are oriented such that when an intake gas enters the intake gas aperture, the particles are deagglomerated, by at least one mode of deagglomeration as described above to separate the particles, and the particles along with a portion of intake gas are dispensed through the dispensing aperture; concurrently forcing a gas through a delivery conduit in communication with the dispensing aperture thereby causing the intake gas to enter the intake gas aperture, de-agglomerate the particles, and dispense the particles along with a portion of intake gas through the dispensing aperture; and, delivering the particles through a delivery conduit of the device, for example, in an inhaler mouthpiece. In embodiment described herein, to effectuate powder deagglomeration, the dry powder inhaler can be structurally configured and provided with one or more zones of powder deagglomeration, wherein the zones of deagglomeration during an inhalation maneuver can facilitate tumbling of a powder by air flow entering the inhaler, acceleration of the air flow containing a powder, deceleration of the flow containing a powder, shearing of a powder particles, expansion of air trapped in the powder particles, and/or combinations thereof.

In another embodiment, the inhalation system comprises a breath-powered dry powder inhaler, a cartridge containing a medicament, wherein the medicament can comprise, for example, a drug formulation for pulmonary delivery such as a composition comprising a diketopiperazine and an active agent. In some embodiments, the active agent comprises peptides and proteins, such as insulin, glucagon-like peptide 1, oxyntomodulin, peptide YY, exendin, parathyroid hormone, analogs thereof, small molecules, vaccines and the like. The inhalation system can be used, for example, in methods for treating conditions requiring localized or systemic delivery of a medicament, for example, in methods for treating diabetes, pre-diabetes conditions, respiratory track infection, osteoporosis, pulmonary disease, pain including headaches including, migraines, obesity, central and peripheral nervous system conditions and disorders and prophalactic use such as vaccinations. In one embodiment, the inhalation system comprises a kit comprising at least one of each of the components of the inhalation system for treating the disease or disorder.

In one embodiment, there is provided a method for the effective delivery of a formulation to the blood stream of a subject, comprising an inhalation system comprising an inhaler including a cartridge containing a formulation comprising a diketopiperazine, wherein the inhalation system delivers a powder plume comprising diketopiperazine microparticles having a volumetric median geometric diameter (VMGD) ranging from about 2.5 μm to 10 μm. In an example embodiment, the VMGD of the microparticles can range from about 2 μm to 8 μm. In an example embodiment, the VMGD of the powder particles can be from 4 μm to about 7 μm in a single inhalation of the formulation of fill mass ranging between 3.5 mg and 10 mg of powder. In this and other embodiments, the inhalation system delivers greater than 90% of the dry powder formulation from the cartridge.

In another embodiment, there is provided a dry powder inhaler comprising: a) a mouthpiece configured to deliver a dry powder to a subject by oral inhalation; b) a container housing, and c) rigid air conduits extending between the container housing and the mouthpiece and configured to communicate with ambient air; wherein the dry powder inhaler is configured to emit greater than 75% of a dry powder as powder particles from a container oriented in the container housing in a single inhalation and the powder particles emitted have a volumetric median geometric diameter (VMGD) of less than about 5 microns, when a user inhales through the mouthpiece to generate a peak inspiratory pressure of about 2 kPa within two seconds and an area under the curve (AUC) within 1 second for a pressure versus time curve of at least about 1.0, 1.1 or 1.2 kPa*sec. In another embodiment, the AUC within 1 second for a pressure versus time curve is between about 1.0 and about 15 kPa*sec.

In some embodiments, there is also provided a method of delivering a dose of a dry powder medication using a high resistance dry powder inhaler comprising, providing a high resistance dry powder inhaler containing a dose of a dry powder medicament and inhaling from the inhaler with sufficient force (or effort) to reach a peak inspiratory pressure of at least 2 kPa within 2 seconds; and generating an area under the curve in the first second ($AUC_{0-1sec}$) of a inspiratory pressure versus time curve of at least about 1.0, 1.1 or 1.2 kPa*sec; wherein greater than 75% of the dry powder dose is discharged or emitted from the inhaler as powder particles. In some embodiments the VMGD of the emitted particles is less than about 5 microns.

In another embodiment, a method of delivering an adequately de-agglomerated dose of a dry powder medication using a high resistance dry powder inhaler comprising, providing a high resistance dry powder inhaler containing a dose of a dry powder medicament; inhaling from the inhaler with sufficient force to reach a peak inspiratory pressure of at least 2 kPa within 2 seconds; and generating an area under the curve in the first second ($AUC_{0-1sec}$) of a inspiratory pressure-time curve of at least about 1.0, 1.1, or 1.2 kPa*second; wherein VMGD (×50) of the emitted powder is less than about 5 um. In an alternative embodiment, the dry powder is composed of microparticles with a median particle size and the VMGD (×50) of the emitted powder particles is not greater than 1.33 times the median particle size when the inhaler is used optimally, for example, at about 6 kPa.

In another embodiment, described is a use of a high resistance dry powder inhaler for the delivery of a dry powder wherein the dry powder inhaler having an airflow resistance value ranging from about 0.065 (√kPa)/liter per minute to about 0.200 (√kPa)/liter per minute, and containing the dose of the dry powder, wherein sufficient force is applied to reach a peak inspiratory pressure of at least 2 kPa within 2 seconds; and wherein an area under the curve in the first second ($AUC_{0-1sec}$) of a inspiratory pressure versus time curve of at least about 1.0, 1.1 or 1.2 kPa*sec is generated; and wherein greater than 75% of the dose of the dry powder is discharged or emitted from the inhaler as powder particles.

In some embodiments the inhalation systems described herein are used to treat patients in need of treatment of a disease or disorder described herein using a medicament as described.

In still another embodiment, a high resistance dry powder inhaler for use to deliver a dry powder medicament to a patient is described, characterized in that the dry powder inhaler is provided having an airflow resistance value ranging from about 0.065 (√kPa)/liter per minute to about 0.200 (√kPa)/liter per minute, and containing a dose of the dry powder medicament, wherein in use sufficient force is applied to reach a peak inspiratory pressure of at least 2 kPa within 2 seconds; and an area under the curve is generated in the first second ($AUC_{0-1sec}$) of an inspiratory pressure versus time curve of at least about 1.0, 1.1 or 1.2 kPa*sec; and wherein greater than 75% of the dose of the dry powder is discharged or emitted from the inhaler as powder particles.

In another embodiment, an inhalation system is provided comprising an inhaler, a cartridge containing a dry powder formulation for delivery to the systemic circulation comprising diketopiperazine microparticles; wherein the diketopiperazine microparticles deliver a plasma level (exposure) of diketopiperazine having an $AUC_{0-2\,hr}$ between 1,300 ng*min/mL and 3,200 ng*min/mL per mg of diketopiperazine emitted in a single inhalation. In another exemplary embodiment, an inhalation system is provided comprising an inhaler, a cartridge containing a dry powder formulation for delivery to the systemic circulation comprising diketopiperazine microparticles; wherein the diketopiperazine microparticles deliver a plasma level (exposure) of diketopiperazine having an $AUC_{0-\infty}$ greater than 2,300 ng*min/mL per mg of powder emitted in a single inhalation. In an aspect of such embodiments the DKP is FDKP. In this and other embodiments, the diketopiperazine microparticles do not cause a reduction in lung function as assessed by pulmonary function tests and measured as forced expiratory volume in one second (FEV1). In certain embodiments, the measured plasma exposure of FDKP in a subject can be greater than 2,500 ng*min/mL per mg of FDKP powder emitted in a single inhalation. In alternate embodiments, the measured plasma exposure, $AUC_{0-\infty}$ of FDKP of a subject can be greater than 3,000 ng*min/mL per mg of FDKP powder emitted in a single inhalation. In yet another embodiment, the measured plasma exposure of FDKP $AUC_{0-\infty}$ in a subject can be less than or about 5,500 ng*min/mL per mg of FDKP emitted in a single inhalation of a dry powder composition comprising FDKP. In some embodiments, the stated level of exposure represents an individual exposure. In alternate embodiments, the stated level of exposure represents a mean exposure. Active agent quantities, including contents and exposures may be express alternatively in units of activity or mass.

In these and other embodiments, the microparticles can further comprise an active ingredient. In particular embodiments, the active ingredient is insulin. In another exemplary embodiment, an inhalation system is provided comprising an inhaler, a cartridge containing a dry powder formulation for delivery to the systemic circulation comprising diketopiperazine microparticles containing insulin; wherein the diketopiperazine microparticles deliver a plasma level (exposure) of insulin with an $AUC_{0\text{-}2\ hr}$ greater than 160 µU*min/mL per units of insulin in the powder formulation emitted in a single inhalation. In an aspect of this embodiment, the inhalation system is configured to deliver and attain an insulin plasma level or exposure wherein the measured insulin $AUC_{0\text{-}2\ hr}$ ranges from about 100 to 1,000 µU*min/mL per units of insulin in the powder formulation emitted in a single inhalation. In some embodiments, the stated level of exposure represents an individual exposure. In alternate embodiments, the stated level of exposure represents a mean exposure.

In another exemplary embodiment, an inhalation system is provided comprising an inhaler, a cartridge containing a dry powder formulation for delivery to the systemic circulation comprising diketopiperazine microparticles comprising insulin; wherein the diketopiperazine microparticles deliver a plasma level (exposure) of insulin with an $AUC_{0\text{-}4\ hr}$ greater than 100 µU*min/mL per U of insulin filled emitted in a single inhalation. In an aspect of this embodiment, the inhalation system is configured to deliver to a patient a formulation of insulin and fumaryl diketopiperazine which attains a plasma exposure of insulin having measured $AUC_{0\text{-}4\ hr}$ in the range of 100 to 250 µU*min/mL per U of insulin filled dose, emitted in a single inhalation. In aspects of these embodiments, the $AUC_{0\text{-}4\ hr}$ can be greater than 110, 125, 150 or 175 µU*min/mL per U of insulin filled, emitted in a single inhalation. In this and other embodiments, the insulin content of the formulation comprises from about 10 to about 20% (w/w) of the formulation In still another exemplary embodiment, an inhalation system is provided comprising an inhaler, a cartridge containing a dry powder formulation for delivery to the systemic circulation comprising diketopiperazine microparticles containing insulin; wherein the diketopiperazine microparticles deliver a plasma level of insulin with a $C_{max}$ over 10 µU/mL per mg of powder emitted in a single inhalation, within 30 minutes of administration. In an aspect of this embodiment, the insulin formulation administered generates a $C_{max}$ ranging from about 10 to 20 µU/mL per mg of powder emitted in a single inhalation, and within 30 minutes after administration. In further aspects of this embodiment, insulin $C_{max}$ can be attained within 25, 20, or 15 minutes of administration. In alternatives of these $C_{max}$ embodiments, the $C_{max}$ attained after pulmonary inhalation of the formulation is greater than 3 µU/mL per U of insulin filled into a cartridge, or in the range of 3 U to 6 U, or 4 U to 6 µU/mL per U of insulin in a cartridge dose.

In another embodiment, an inhalation system, comprising: a dry powder inhaler; and a dry powder formulation comprising a plurality of powder particles of a diketopiperazine is provided, wherein the inhalation system is configured to deliver the diketopiperazine to the pulmonary circulation of a subject, and the diketopiperazine can be measured in the subject's plasma having a mean exposure or $AUC_{0\text{-}\infty}$ greater than 2,300 ng*min/mL per mg of diketopiperazine content in the dry powder formulation administered in a single inhalation. In one embodiment, the inhalation system further comprises a cartridge configured to adapt to a breath powered dry powder inhaler. In this and other embodiments, the diketopiperazine in the formulation is 3,6-bis(N-fumaryl-4-aminobutyl)-2,5-diketopiperazine (FDKP).

In embodiments wherein FDKP is used in the formulation, the system can deliver the FDKP into the systemic circulation at a $T_{max}$ of less than 1 hour. In some embodiments, the $T_{max}$ for FDKP can be less than 15 or 30 minutes after administration of the FDKP in a single inhalation. In this an other embodiments, the AUC is measured from 0 to 2 hours, 0 to 4 hrs or 0 to ∞.

In another embodiment, an inhalation system, comprising: a breath-powered dry powder inhaler, and a dry powder formulation comprising a plurality of diketopiperazine particles is provided; wherein the inhalation system is operably configured to emit a powder plume comprising the diketopiperazine microparticles having a volumetric median geometric diameter ranging from 2 µm to 8 µm and a geometric standard deviation of less than 4 µm.

In yet another embodiment, an inhalation system for pulmonary delivery of a drug, comprising: a breath-powered dry powder inhaler, and a dry powder formulation comprising a plurality of diketopiperazine particles is provided; wherein the inhalation system is operably configured to emit more than 90% of the powder particles that dissolve and are absorbed into the blood in less than 30 minutes or less than 25 minutes yield a peak concentration of the diketopiperazine after a single inhalation of the dry powder formulation. In some embodiments, the system emits more than 95% of the powder particles in a single inhalation, which particles are absorbed into the circulation.

In one embodiment, an inhalation system, comprising: a dry powder inhaler; and a dry powder formulation comprising a plurality of dry powder particles comprising insulin is provided; wherein the inhalation system is configured to deliver the insulin to the pulmonary circulation of a subject, and the insulin can be measured in a subject's plasma at an exposure having a mean $AUC_{0\text{-}2\ hr}$ greater than 160 uU*min/mL per unit of insulin emitted in the dry powder formulation administered in a single inhalation.

In one embodiment, the inhalation system, the dry powder formulation is administered to a subject by oral inhalation and the formulation comprises powder particles of insulin which can deliver the insulin to the subject systemic circulation, wherein a Cmax for insulin is measured in less than 30 minutes after administration to a patient in a single inhalation.

In an embodiment, there is provided an inhalation system, comprising: a breath-powered dry powder inhaler, and a powder formulation comprising a plurality of diketopiperazine particles; wherein the inhalation system is operably configured to emit a powder plume comprising the diketopiperazine microparticles having a volumetric median geometric diameter ranging from 2 µm to 8 µm and a geometric standard deviation of less than 4 µm.

In yet another embodiment, an inhalation system for pulmonary delivery of a drug is provided, comprising: a breath-powered dry powder inhaler, and a powder formulation comprising a plurality of diketopiperazine particles; wherein the inhalation system is operably configured to emit powder particles that are absorbed into the blood to yield a peak concentration of the drug in less than or equal to 30, 25, 20, or 15 minutes.

In one embodiment, a dry powder inhaler comprising a mouthpiece configured to deliver a dry powder to a subject by oral inhalation, a container configured to hold a dry powder, and air conduits extending between the container and the mouthpiece and configured to communicate with ambient air, wherein the dry powder inhaler is configured to emit greater than 75% of the dry powder as powder particles in a single inhalation and the powder particles emitted have a volumetric median geometric diameter of less than 5 microns, when a user inhales through the mouthpiece to generate a peak inspiratory pressure of about 2 kPa within two seconds, and an $AUC_{0-1sec}$ a inspiratory pressure versus time curve of at least about 1.0, of 1.1 or 1.2 kPa*sec; wherein greater than 75% of the dry powder dose is discharged or emitted from the inhaler as powder particles.

In yet another embodiment, a method of delivering a dose of a dry powder medication to a subject is disclosed using a high resistance dry powder inhaler comprising the steps of providing a dry powder inhaler having a resistance value to airflow ranging from about 0.065 ($\sqrt{kPa}$)/liter per minute to about 0.200 ($\sqrt{kPa}$)/liter per minute and containing a dose of a dry powder medicament; inhaling from the inhaler with sufficient force to reach a peak inspiratory pressure of at least 2 kPa within 2 seconds; and generating an $AUC_{0-1sec}$ of a inspiratory pressure versus time curve of at least about 1.0, 1.1 or 1.2 kPa*sec; wherein greater than 75% of the dry powder dose is discharged or emitted from the inhaler as powder particles.

BRIEF DESCRIPTION OF THE DRAWINGS

FIGS. 2, 3, 4, 5, and 6 depict side, top, bottom, proximal and distal views, respectively, of the inhaler of FIG. 1.

FIG. 23 through 27 depict the cartridge embodiment shown in FIG. 22 in a top, bottom, proximal, distal and side views, respectively.

DETAILED DESCRIPTION

Figure 1:
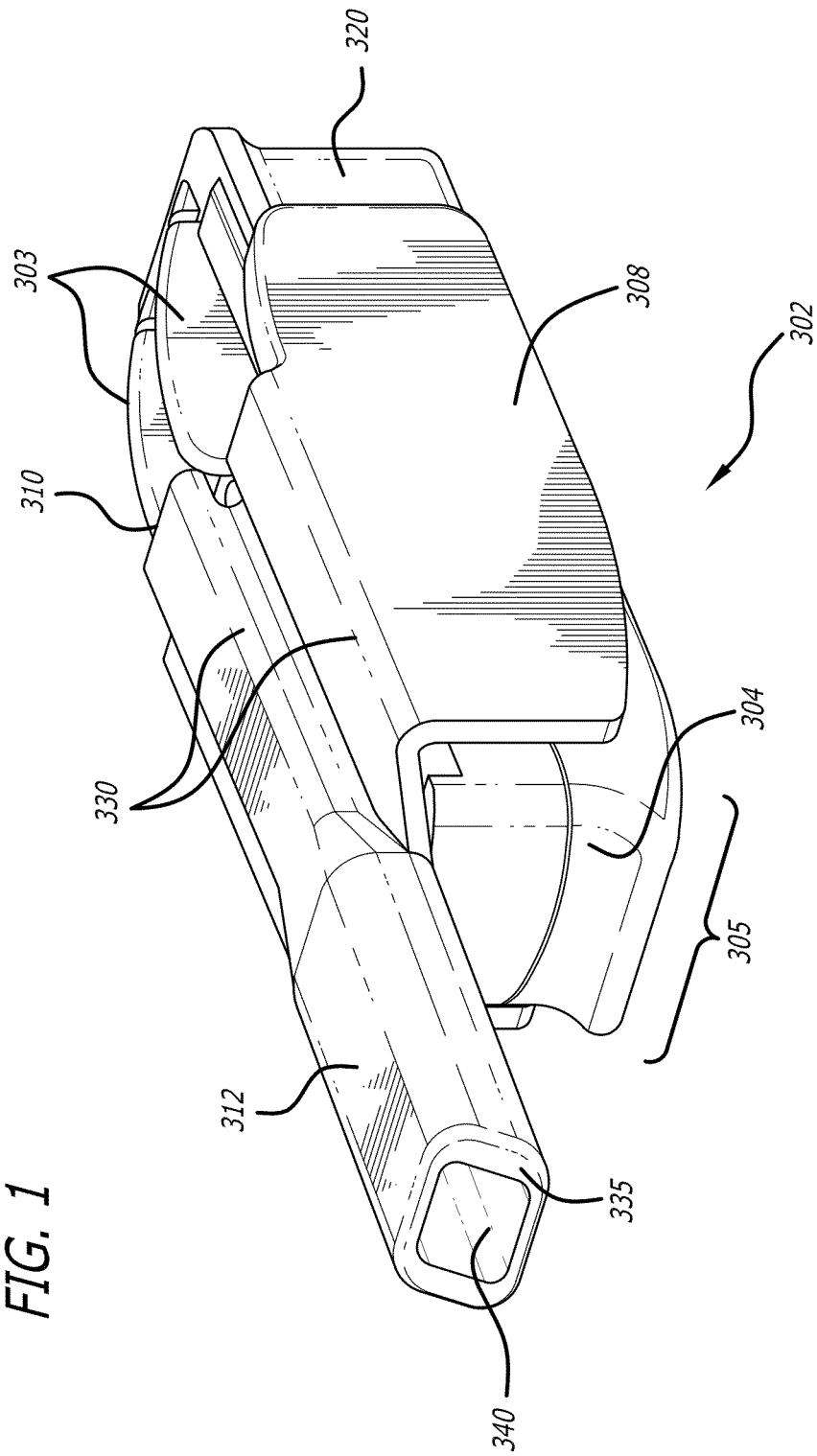
FIG. 1 depicts an example embodiment of the inhaler used in the inhalation system, showing an isometric view of the inhaler in a closed configuration.
Figure 2:
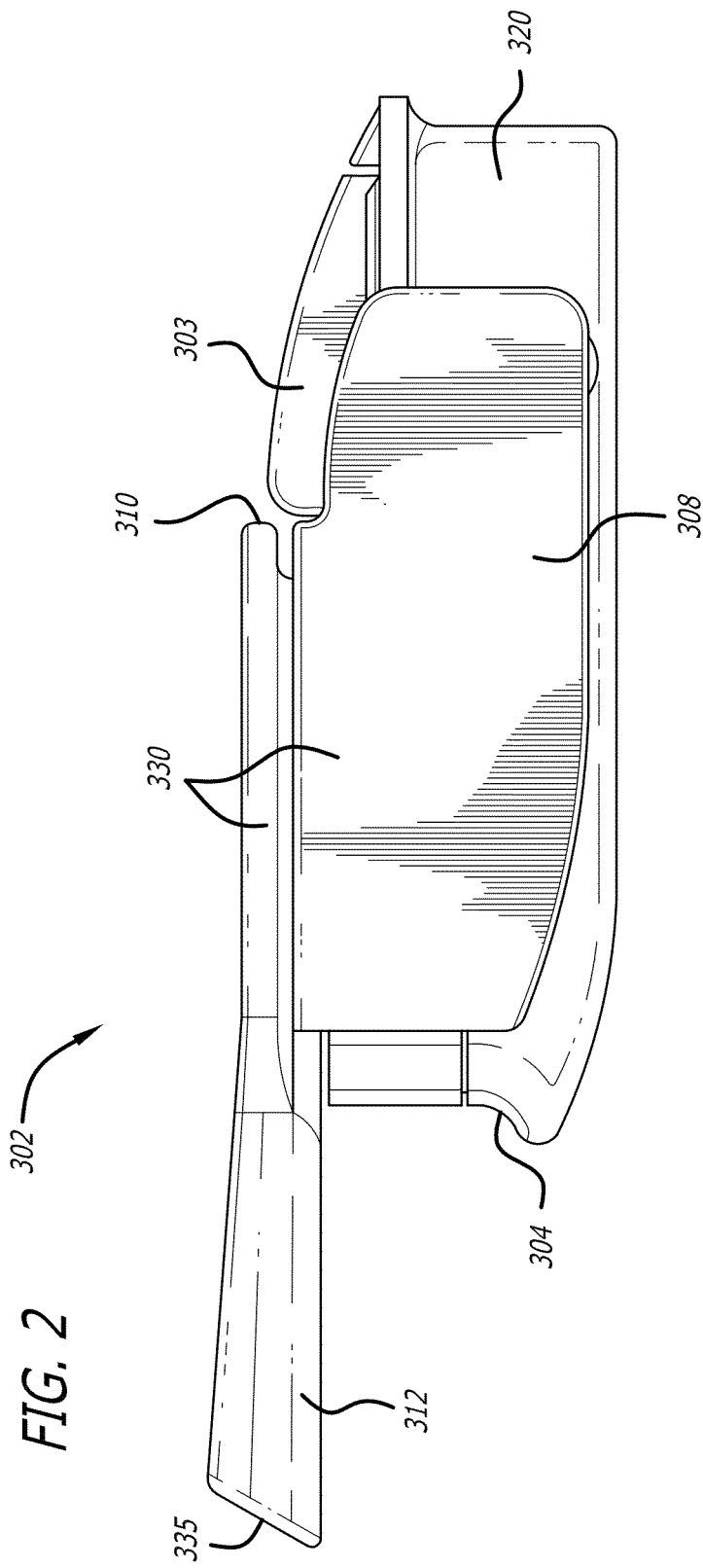
Figure 5:
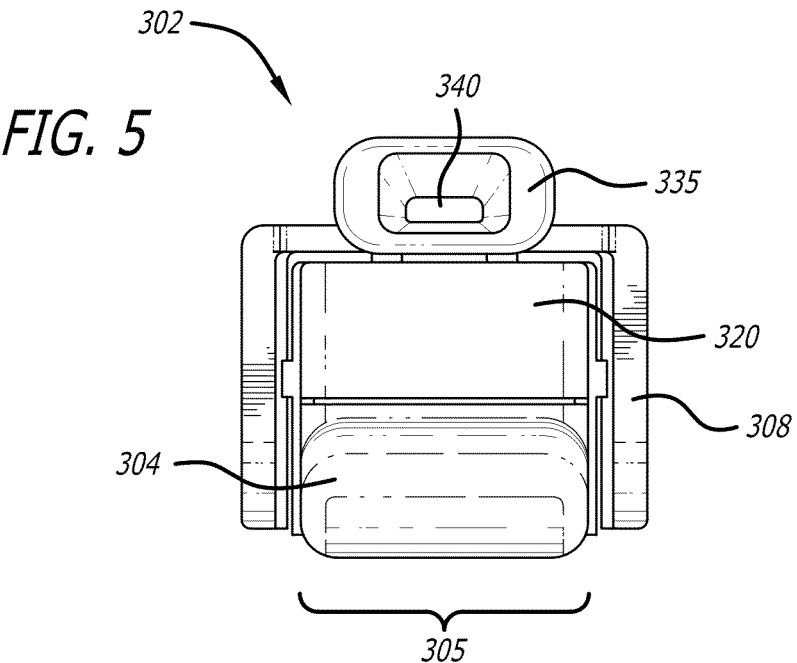
Figure 6:
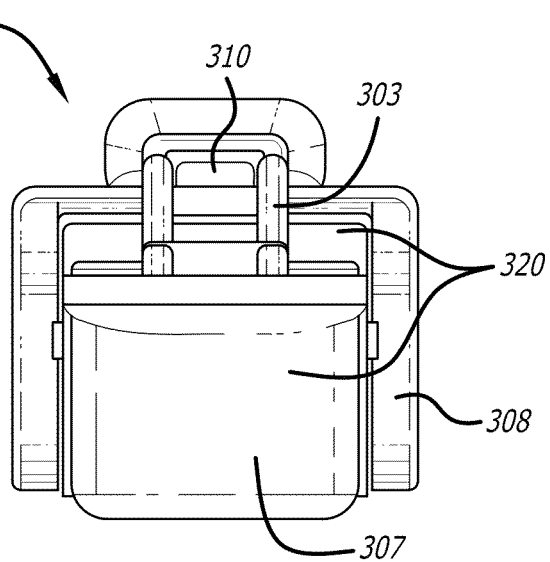

Disclosed herein generally are dry powder inhalers, cartridges for a dry powder inhalers and inhalation systems for delivering one or more pharmaceutical medicaments to a patient via pulmonary inhalation. In one embodiment, an inhalation system comprises a breath-powered dry powder inhaler, and a cartridge containing a pharmaceutical formulation comprising a pharmaceutically active substance or active ingredient and a pharmaceutically acceptable carrier. The dry powder inhaler is provided in various shapes and sizes, and can be reusable or for single use, easy to use, is inexpensive to manufacture and can be produced in high volumes in simple steps using plastics or other acceptable materials. In addition to complete systems, inhalers, filled cartridges and empty cartridges constitute further embodiments disclosed herein. The present inhalation system can be designed to be used with any type of dry powder. In one embodiment, the dry powder is a relatively cohesive powder which requires optimal deagglomeration condition. In one embodiment, the inhalation system provides a re-useable, miniature breath-powered inhaler in combination with single-use cartridges containing pre-metered doses of a dry powder formulation.

Methods for the effective and consistent delivery of a pharmaceutical formulation to the systemic circulation are also disclosed.

As used herein the term "a unit dose inhaler" refers to an inhaler that is adapted to receive a single container a dry powder formulation and delivers a single dose of a dry powder formulation by inhalation from container to a user. It should be understood that in some instance multiple unit doses will be required to provide a user with a specified dosage.

As used herein the term "a multiple dose inhaler" refers to an inhaler having a plurality of containers, each container comprising a pre-metered dose of a dry powder medicament and the inhaler delivers a single dose of a medicament powder by inhalation at any one time.

As used herein a "container" is an enclosure configured to hold or contain a dry powder formulation, a powder containing enclosure, and can be a structure with or without a lid. This container can be provided separately from the inhaler or can be structurally integrated within the inhaler (e.g. non-removable). Further, the container can be filled with a dry powder. A cartridge can also include a container.

As used herein a "powder mass" is referred to an agglomeration of powder particles or agglomerate having irregular geometries such as width, diameter, and length.

As used herein, the term "microparticle" refers to a particle with a diameter of about 0.5 to about 1000 µm, irrespective of the precise exterior or interior structure. However four pulmonary delivery microparticles that are less than 10 µm are generally desired, especially those with mean particles sizes of less than about 5.8 µm in diameter.

As used herein a "rigid air conduit" refers to an air conduit that is associated with the pathway of air through the inhalation system that does not change in geometry or remains constant, for example, in a reusable inhaler the air conduits remain the same after repeated use. The rigid air conduit can be associated with a mouthpiece, container, inhaler housing, container, container housing or the like.

As used herein a "unit dose" refers to a pre-metered dry powder formulation for inhalation. Alternatively, a unit dose can be a single container having multiple doses of formulation that can be delivered by inhalation as metered single amounts. A unit dose cartridge/container contains a single dose. Alternatively it can comprise multiple individually accessible compartments, each containing a unit dose.

As used herein, the term "about" is used to indicate that a value includes the standard deviation of error for the device or method being employed to determine the value.

The present devices can be manufactured by several methods, however, in one embodiment, the inhalers and cartridges are made, for example, by injection molding techniques, thermoforming, using various types of plastic materials, including, polypropylene, cyclicolephin co-polymer, nylon, polyesters such as polyethylenes, and other compatible polymers and the like. In certain embodiments, the dry powder inhaler can be assembled using top-down assembly of individual component parts. In some embodiments, the inhalers are provided in compact sizes, such as from about 1 inch to about 5 inches in dimension, and generally, the width and height are less than the length of the device. In certain embodiments the inhaler is provided in various shapes including, relatively rectangular bodies, cylindrical, oval, tubular, squares, oblongs, and circular forms.

In embodiments described and exemplified herewith, the inhalation system comprising inhaler, cartridge or container, and a dry powder formulation, the inhalers are configured with the cartridge to effectively fluidize, deagglomerate or aerosolize a dry powder formulation by using at least one relatively rigid flow conduit pathway for allowing a gas such as air to enter the inhaler. For example, the inhaler is provided with a first air/gas pathway for entering and exiting a cartridge containing the dry powder, and a second air pathway which can merge with the first air flow pathway exiting the cartridge. The flow conduits, for example, can have various shapes and sizes depending on the inhaler configuration. Examples of inhalers and cartridges that can be used in the present inhalation system are disclosed in, for example, U.S. patent application Ser. No. 12/484,125 (US 2009/0308390), Ser. No. 12/484,129 (US 2009/0308391), Ser. No. 12/484,137 (US 2009/0308392), and Ser. No. 12/717,884 (US 2010/0197565) all of which are incorporated herein by reference in their entirety for all they disclose regarding inhalation systems.

In embodiments exemplified herewith, each inhaler can be used with a suitable cartridge. However, the inhalation system can perform more efficiently when inhaler and cartridge are designed to correspond to one another. For example, the cartridge mounting area of an inhaler can be designed to house only a specific cartridge and therefore, structural configurations of the openings of cartridge and inhaler match or fit one another, for example, as keying areas or surfaces which can aid as safety parameter for users. Examples of a corresponding inhaler and cartridge follows herewith as inhaler 302 which can be used with cartridge 170 and inhaler 900 which can be used with cartridge 150. These inhalers and cartridges have been disclosed in U.S. patent application Ser. Nos. 12/484,125; 12/484,129, and 12/484,137, all of which are incorporated by reference herein in their entirety for all they disclose regarding inhalers and cartridges, and where appropriate, for teachings of additional or alternative details, features, and/or technical background.

Figure 7:
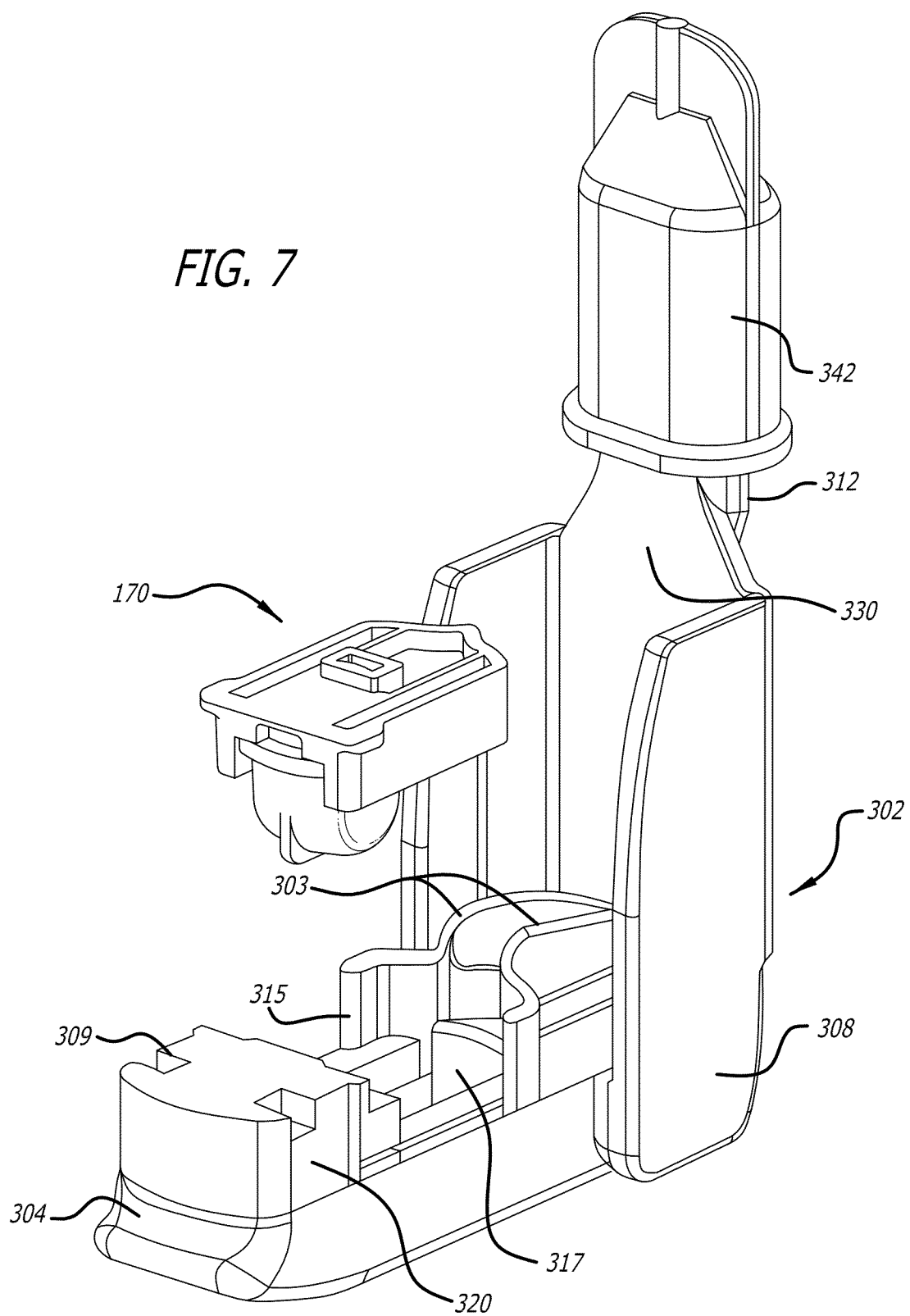
FIG. 7 depicts a perspective view of an embodiment of the inhalation system comprising the inhaler of in FIG. 1 in an open configuration showing a corresponding cartridge and a mouthpiece covering.
Figure 8:
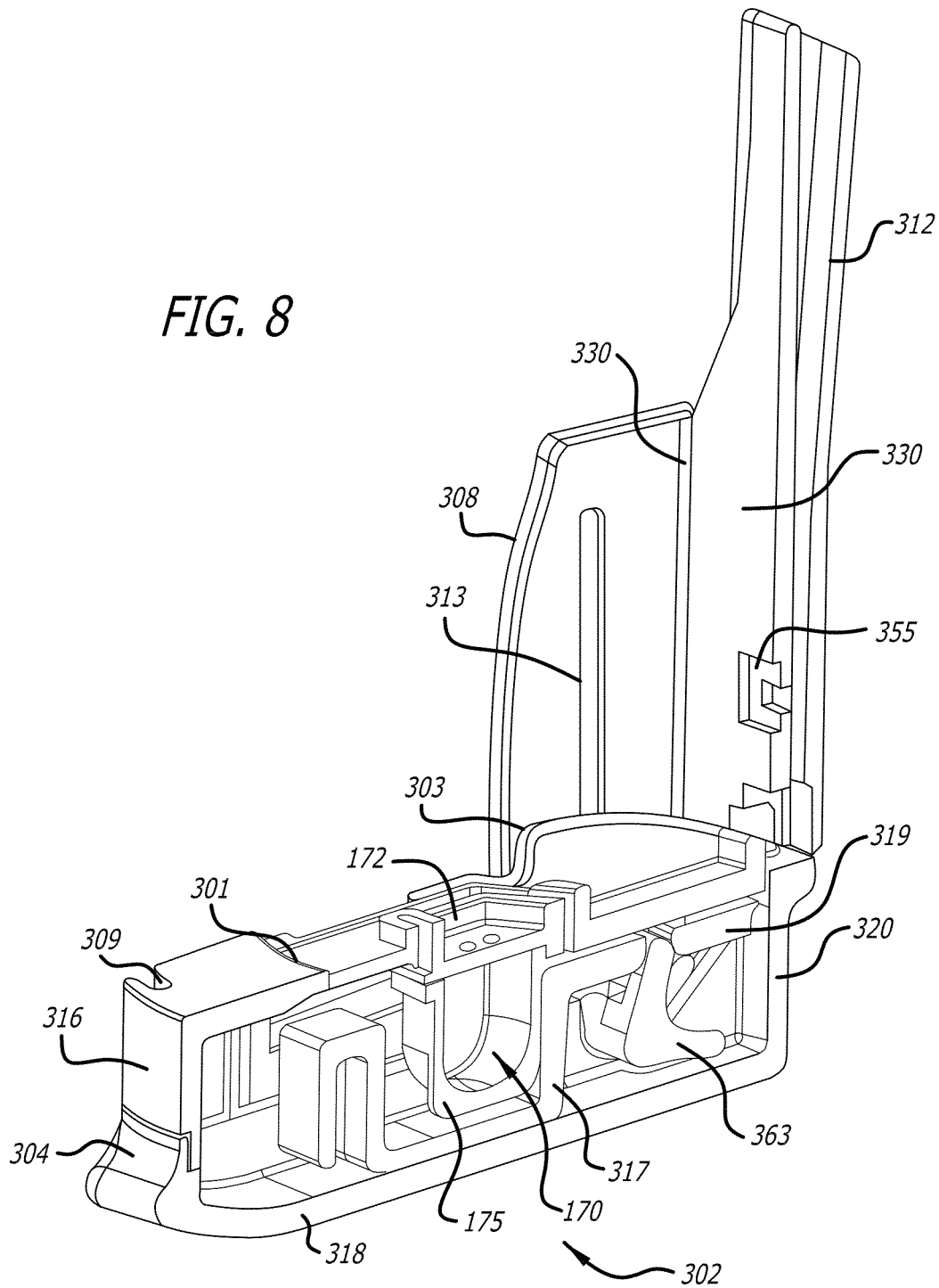
FIG. 8 depicts an isometric view of the inhaler of FIG. 6 in an open configuration with a cartridge installed in the holder in cross-section through the mid-longitudinal axis with a cartridge installed in the cartridge holder and in a containment configuration, and the closed configuration of the inhaler and in dosing configuration of the cartridge FIG. 9.

An embodiment of a dry powder inhaler is exemplified in FIGS. 1-9. In this embodiment, the dry powder inhaler has two configurations, i.e., a closed configuration is illustrated in FIGS. 1 through 6 and 9, and an open configuration is illustrated in FIGS. 7 and 8. The dry powder inhaler 302 in the open configuration permits installation or removal of a cartridge containing a medicament for inhalation. FIGS. 1-6 depict inhaler 302 in a closed configuration from various views and having a relatively rectangular body comprising a housing 320, mouthpiece 330 superiorly to the body and extending outwardly from the body. A portion of mouthpiece 330 tapers towards the end for contacting a user and has an opening 335. Inhaler 302 also comprises a gear mechanism 363, and a sled. Inhaler 302 can be manufactured using, for example, four parts in a top down assembly manner. Mouthpiece 330 further comprises air conduit 340 configured to run along the longitudinal axis of the inhaler and has an oral placement portion 312, air inlet 310 and air outlet 335 configured to have its surface angular or beveled relative to the longitudinal axis of the air conduit, and cartridge port opening 355 which is in fluid communication with housing 320 and/or a cartridge installed in housing 320 for allowing airflow to enter air conduit 340 from the housing or from a cartridge installed in the inhaler in use. FIG. 1 illustrates inhaler 302 in isometric view in a closed position having a more slender body 305 than inhaler 300 formed by housing 320 and cover portion 308 of mouthpiece 330, which extends over and engages housing 320 by a locking mechanism 312, for example, a protrusion. FIGS. 2-6 depict side, top, bottom, proximal and distal views, respectively, of the inhaler of FIG. 1. As shown in the figures, inhaler 302 comprises mouthpiece 330 having an oral placement section 312, an extended portion configured as a cover 308 that can attach to housing 320 at at least one location as shown in FIG. 7. Mouthpiece 330 can pivot to open from a proximal position from a user's hands in an angular direction by hinge mechanism 363. In this embodiment, inhaler 302 is configured also to have gear mechanism 363 as illustrated in FIG. 8 integrated within the hinge for opening the inhaler or mouthpiece 330 relative to housing 320.

Gear mechanism or rack 319 which is part of sled 317 and pinion 363 are configured with the mouthpiece as part of the hinge mechanism to engage housing 320, which housing can also be configured to house sled 317. In this embodiment, sled 317 is configured as a separate part and has a portion configured as a rack which engages the gearwheel configured on the hinge mechanism. Hinge mechanism 363 allows movement of mouthpiece 330 to an open or cartridge loading configuration, and close configuration or position of inhaler 302 in an angular direction. Gear mechanism 363 in inhalers 300, 302 can actuate the sled to allow concurrent movement of sled 317 within housing 320 when the inhaler is effectuated to open and close by movement of mouthpiece 330, which sled 317 is integrally configured with rack 319 as part of gear mechanism 363. In use with a cartridge, the inhaler's gear mechanism 363 can reconfigure a cartridge by movement of sled 317 during closing of the inhaler, from a cartridge containment configuration after a cartridge is installed on the inhaler housing or mounting area to a dosing configuration when the inhaler is closed. Movement of the mouthpiece 330 to an open inhaler configuration after inhalation with a cartridge 170, or to a disposable configuration after a subject has effectuated dosing of a dry powder formulation. In the embodiment illustrated herein, the hinge and gear mechanism are provided at the distal end of the inhaler, however, other configurations can be provided so that the inhaler opens and closes to load or unload a cartridge as a clam-like configuration.

As shown in FIG. 1 and in use, airflow enters the inhaler through air inlet 310 and simultaneously into air conduit 340 which passes cartridge 170 through air inlet 355. In one example embodiment, the internal volume of mouthpiece 330 air conduit 340 extending from inlet port 355 to outlet port 335 is greater than about 0.2 cm$^3$. In other example embodiments, the internal volume is about 0.3 cm$^3$, or about 0.3 cm$^3$, or about 0.4 cm$^3$ or about 0.5 cm$^3$. In another example embodiment, this internal volume of the mouthpiece is greater than 0.2 cm$^3$ is the internal volume of the mouthpiece 330. In an example embodiment, the internal volume of mouthpiece ranges from 0.2 to 6.5 cm$^3$. A powder contained within cartridge container 175 is fluidized or entrained into the airflow entering the cartridge through tumbling of the powder content. The fluidized powder then gradually exits through dispensing port 173, 127 and into the mouthpiece air conduit 340 and further deagglomerated and diluted with the airflow entering at air inlet 310, prior to exiting outlet port 335.

In one embodiment, housing 320 comprises one or more component parts, for example, a top portion 316 and a bottom portion 318. The top and bottom portions are configured to adapt to one another in a tight seal, forming an enclosure which houses sled 317 and the hinge and/or gear mechanisms 363. Housing 320 is also configured to have one or more openings 309 to allow air flow into the interior of the housing, a locking mechanism 313, such as protrusions or snap rings to engage and secure mouthpiece cover portion 308 in the closed position of inhaler 302. Housing 320 is also configured to have a cartridge holder or cartridge mounting area 315 which is configured to correspond to the type of cartridge to be used with the inhaler. In this embodiment, the cartridge placement area or holder is an opening in the top portion of housing 320 which opening also allows the cartridge bottom portion or container to lie on sled 317 once a cartridge is installed in inhaler 302. The housing can further comprise grasping areas 304, 307 configured to aid a user of the inhaler to firmly or securely grip the inhaler to open it to load or unload a cartridge. Housing 320 can further comprise flanges configured to define an air channel or conduit, for example, two parallel flanges 303 which are also configured to direct air flow into the inhaler air inlet 310 and into a cartridge air inlet of the cartridge air conduit positioned in the inhaler. Flanges 310 are also configured to prevent a user from obstructing inlet port 310 of inhaler 302.

FIG. 7 depicts an isometric view of the inhaler of FIG. 1 in an open configuration with mouthpiece covering, for example, cap 342 and cartridge 170 which are configured to correspond to the cartridge mounting area and allow a cartridge to be installed in cartridge holder 315 for use. In one embodiment, reconfiguration of a cartridge from a containment position, as provided after manufacturing, can be effectuated once the cartridge is installed in cartridge holder 315, which is configured within housing 320 and to adapt to the inhaler so that the cartridge has the proper orientation in the inhaler and can only be inserted or installed in only one manner or orientation. For example, cartridge 170 can be configured with locking mechanism 301 that matches a locking mechanism configured in the inhaler housing, for example, the inhaler mounting area, or holder can comprise a beveled edge 301 which would correspond to a beveled edge 180 on the cartridge of, for example, cartridge 170 to be installed in the inhaler. In this embodiment, the beveled edges form the locking mechanism which prevents the cartridge from popping out of holder 315 during movement of sled 317.

Figure 9:
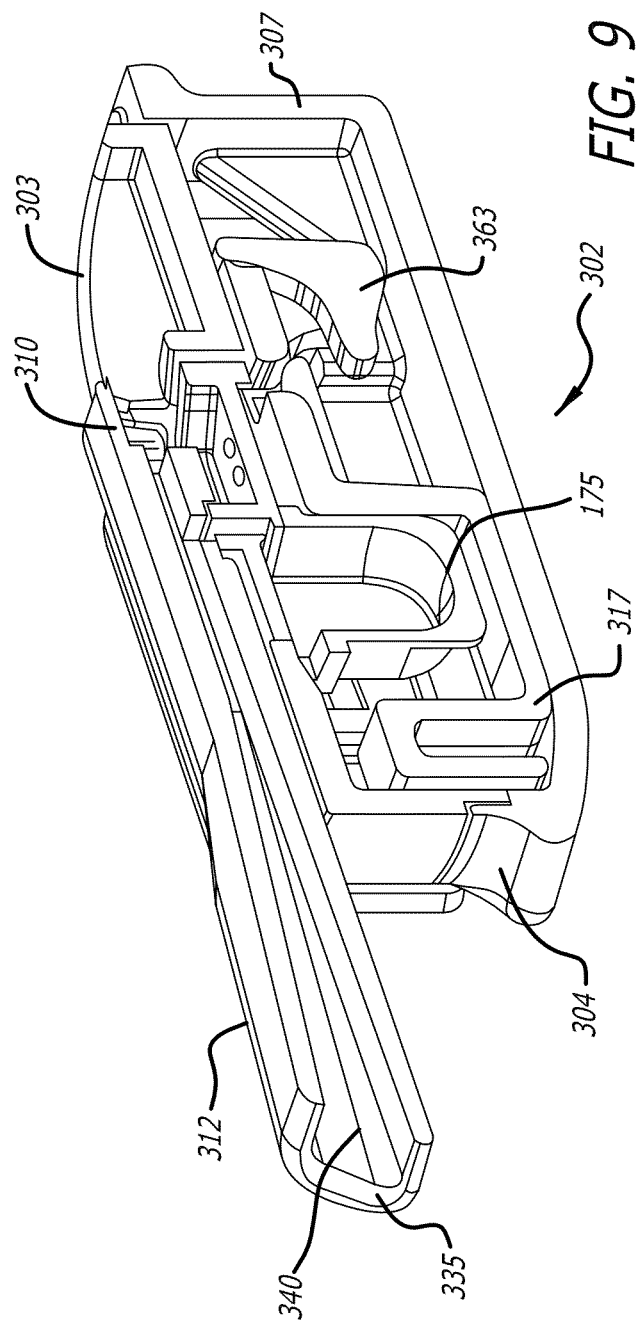

In one particular embodiment illustrated in FIGS. 8 and 9, the cartridge lid is configured with a beveled edge so that it remains secure in the housing mounting area in use, which mounting area has matching beveled edges. FIGS. 8 and 9 also show rack mechanism 319 configured with sled 317 to effectuate movement of a cartridge container 175 of cartridge 170 slideably under the cartridge top to align the container under the cartridge top undersurface configured to have dispensing port(s) in a closed inhaler configuration or cartridge dispensing or dosing position or configuration when inhaler 302 is ready for dosing a user. In the dosing configuration, an air inlet port forms by the border of the cartridge top and the rim of the container, since the undersurface of the cartridge top is raised relative to the containment undersurface. In this configuration, an air conduit is defined through the cartridge by the air inlet, the internal volume of the cartridge which is exposed to ambient air and the openings in the cartridge top or dispensing port in the cartridge top, which air conduit is in fluid communication with air conduit 340 of the mouthpiece.

Inhaler 302 can further include a mouthpiece cap 342 to protect the oral placement portion of the mouthpiece. FIG. 8 depicts the inhaler of FIG. 1 in cross-section through the mid-longitudinal axis with a cartridge installed in the cartridge holder and in an open configuration, and in the closed configuration FIG. 9 in a cartridge dispensing or dosing configuration.

FIG. 8 illustrates the position of cartridge 350 installed in holder or mounting area 315 and showing the internal compartment parts of inhaler 302 and cartridge 170 relative to one another, including boss 326 with dispensing ports 327; gear mechanism 360, 363 and snaps 380 which assist in maintaining the device in a closed configuration.

Figure 10:
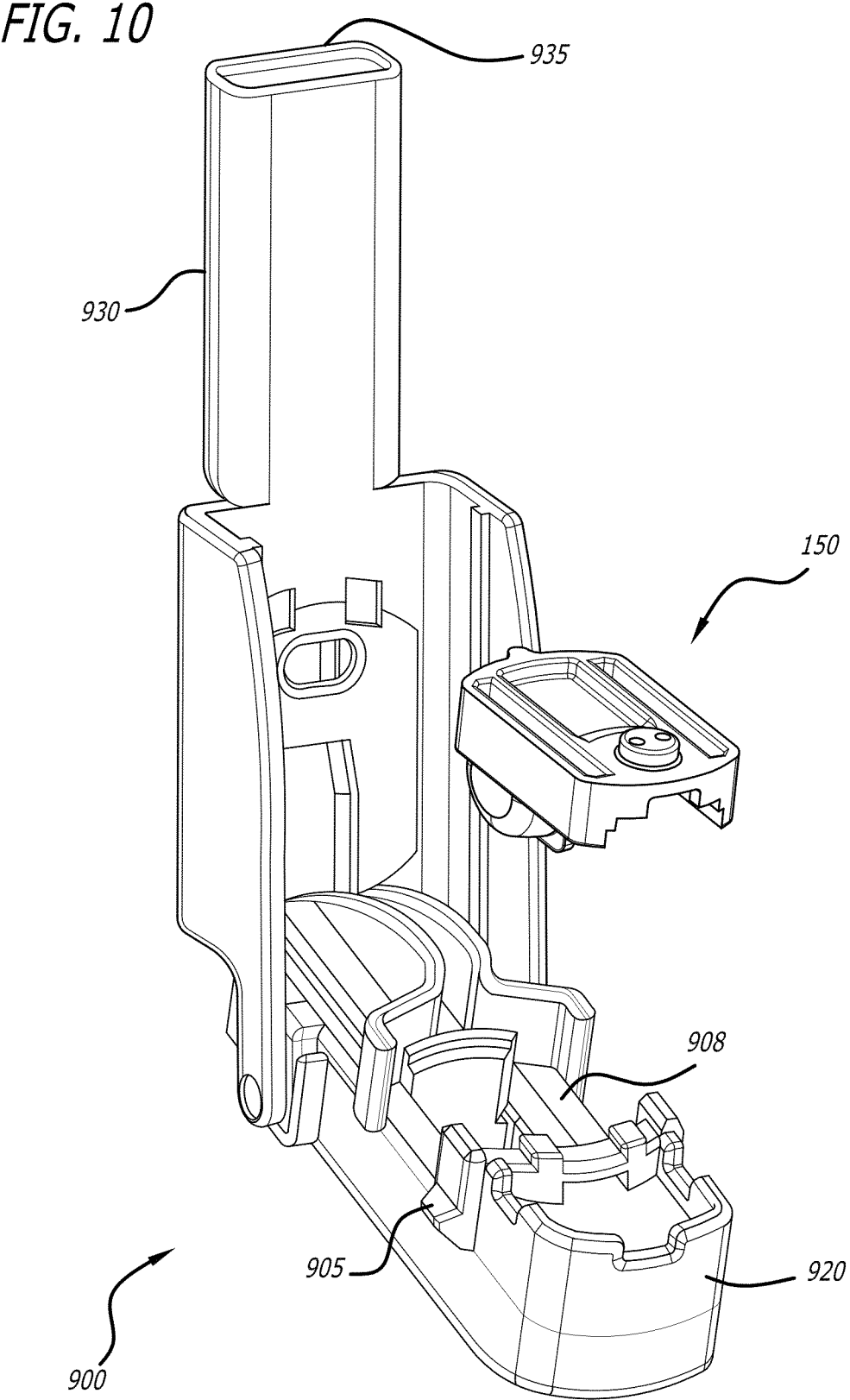
FIG. 10 illustrates a perspective view of an alternate embodiment of a dry powder inhalation system, the inhaler shown in an opened configuration, illustrating the type and orientation of a corresponding cartridge that can be installed in the inhaler.
Figure 11:
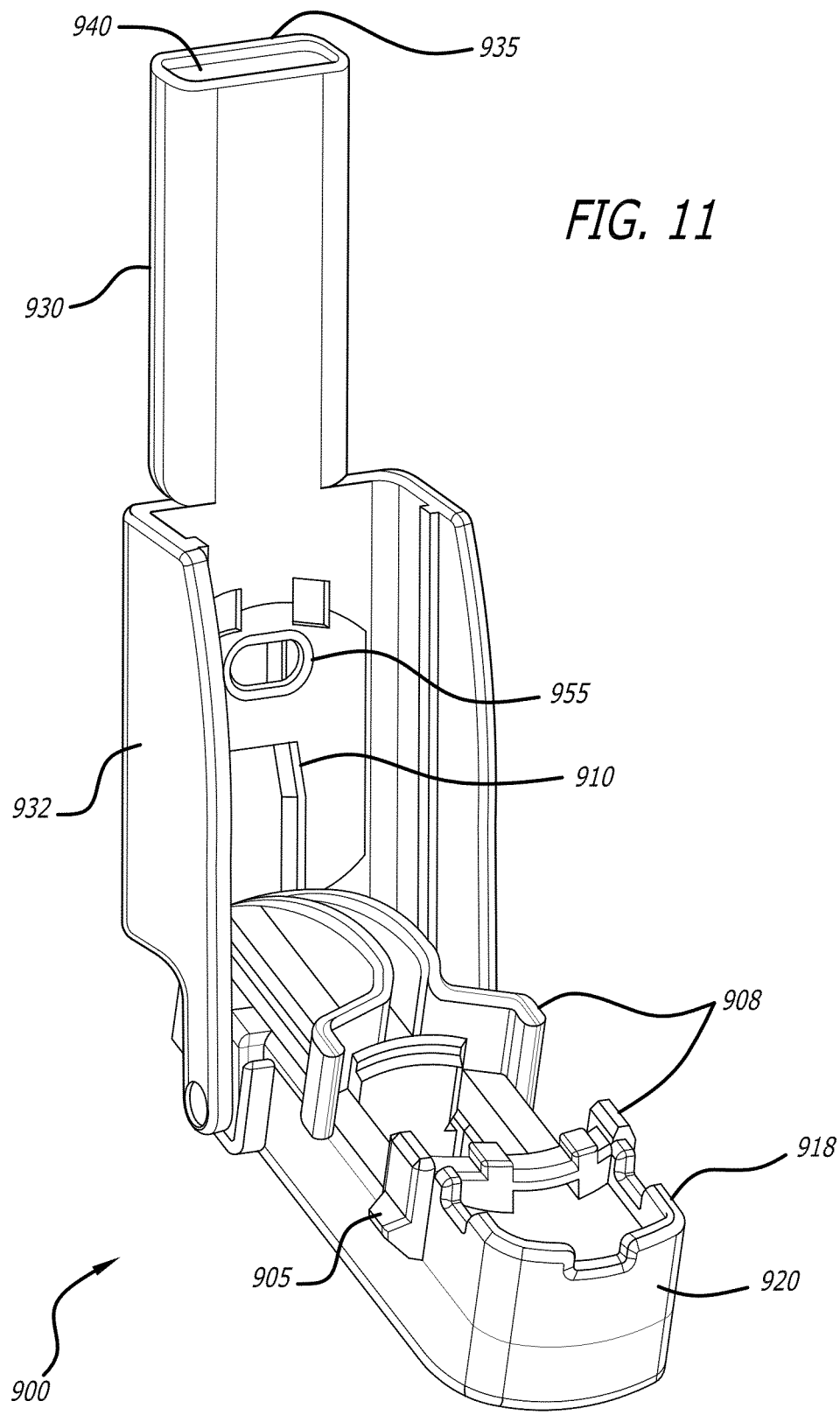
FIG. 11 depicts an isometric view of the dry powder inhaler of FIG. 10 in an open configuration.
Figure 12:
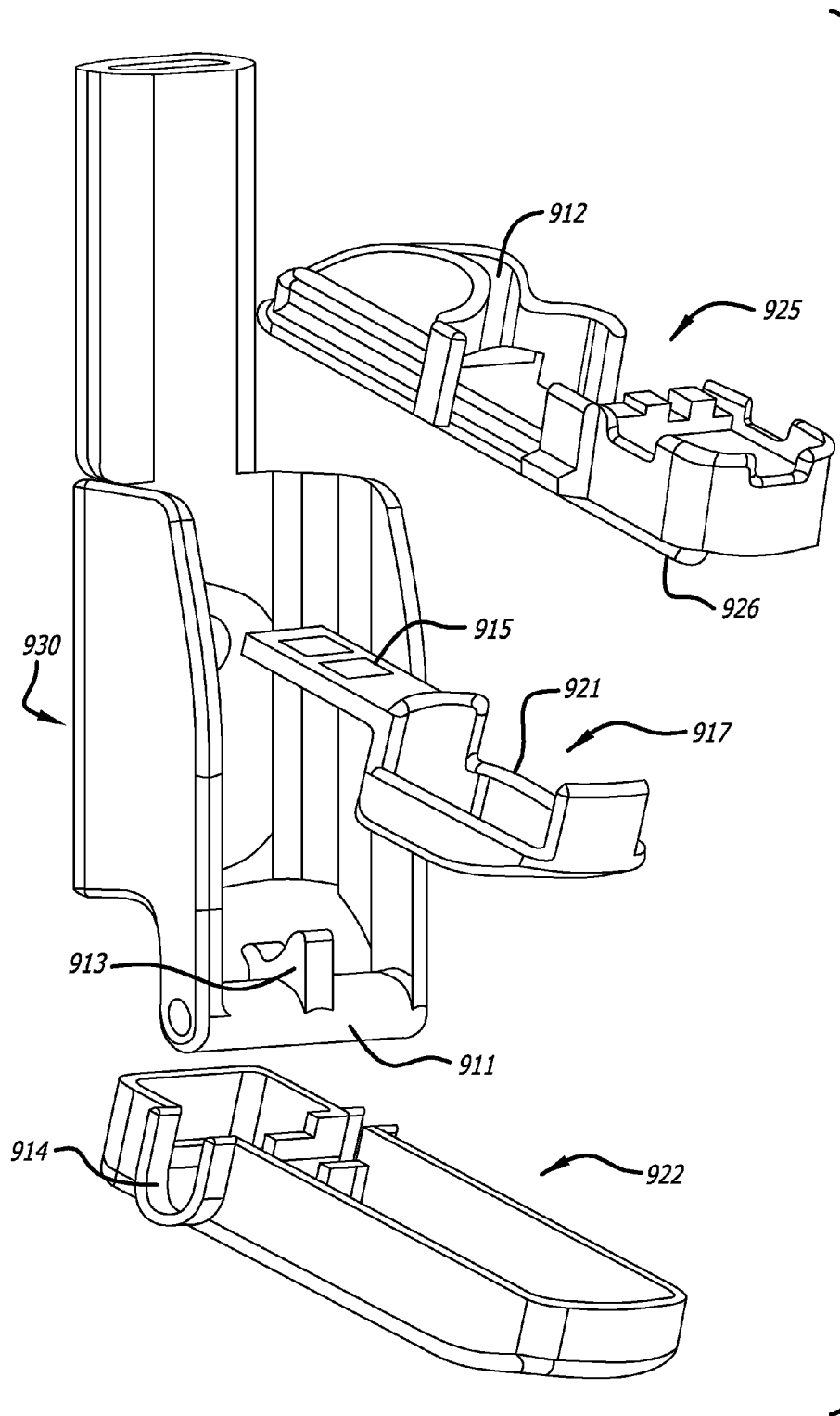
FIG. 12 illustrates an exploded view of the inhaler embodiment of FIG. 48 showing the inhaler component parts.

FIGS. 10-16 illustrate yet another embodiment of the dry powder inhaler of the inhalation system. FIG. 10 depicts inhaler 900 in an open configuration which is structurally configured similarly as inhaler 302 shown in FIGS. 1-9. Inhaler 900 comprises mouthpiece 930 and housing subassembly 920 which are attached to one another by a hinge so that mouthpiece 930 pivots relative to the housing subassembly 920. Mouthpiece 930 further comprises integrally formed side panels 932 wider than housing 920, which engage with housing protrusions 905 to attain the closed configuration of inhaler 900. Mouthpiece 930 further comprises air inlet 910, air outlet 935; air flow conduit 940 extending from air inlet 910 to air outlet 935 for contacting a user's lips or mouth, and aperture 955 on the floor or bottom surface which communicates with airflow conduit 940 of the inhaler. FIG. 12 illustrates inhaler 900 in an exploded view, showing the component parts of the inhaler, including the mouthpiece 930 and housing subassembly 920. As depicted in FIG. 12, the mouthpiece is configured as a single component and further comprises a bar, cylinder or tube 911 configured with teeth or gear 913 for articulating with housing 920 so that movement of mouthpiece 930 relative to housing 920 in an angular direction attains closure of the device. An air channel 912 can be provided to the housing which can direct an air flow towards mouthpiece air inlet 910. Air channel 912 is configured so that in use, a user's finger placed over the channel cannot limit or obstruct airflow into air conduit 940.

Figure 13:
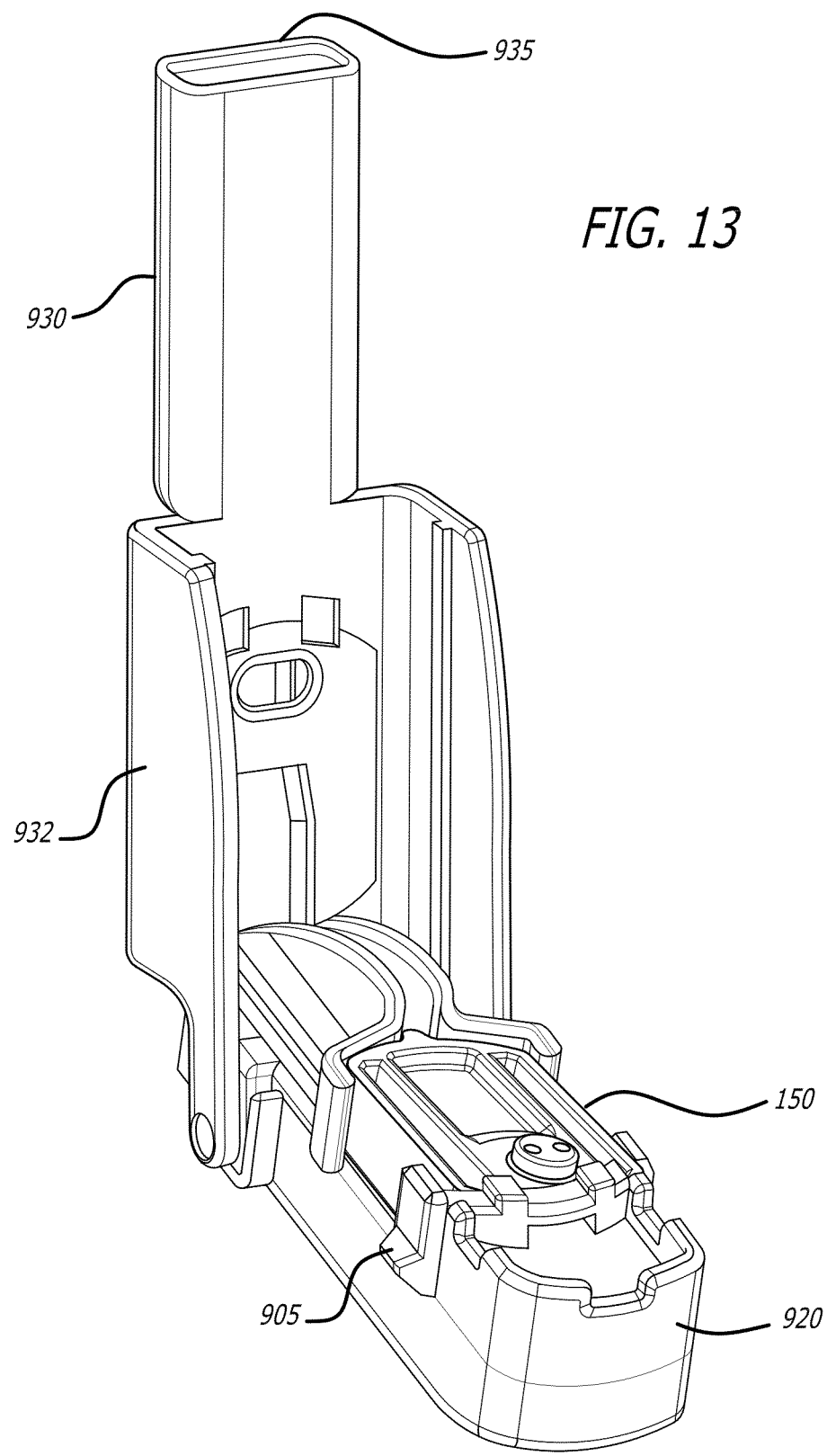
FIG. 13 illustrates a perspective view of the inhaler in FIG. 10 in the open configuration and showing a cartridge installed in the inhaler.
Figure 14:
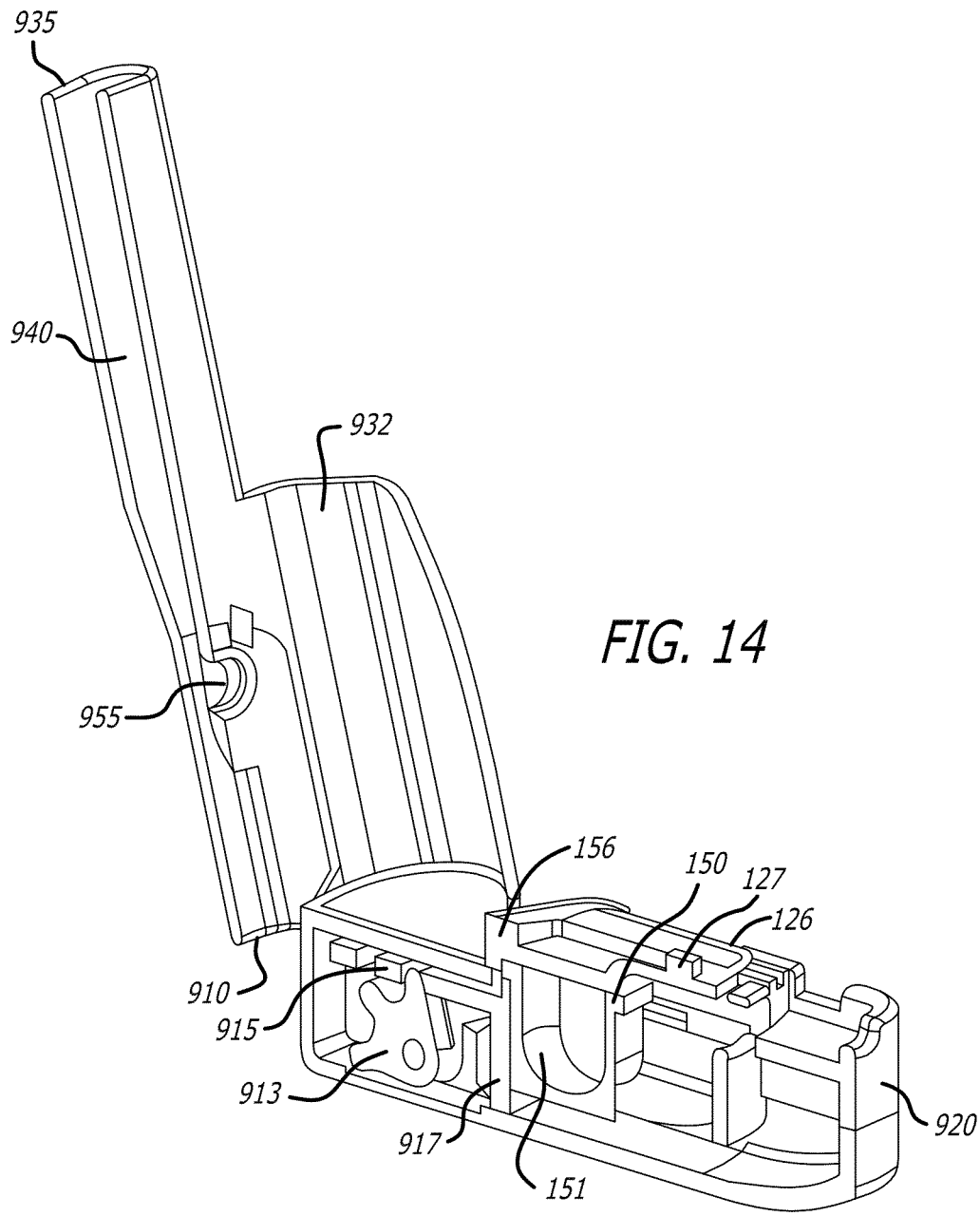
FIG. 14 illustrates a mid-longitudinal section of the inhaler depicted in FIG. 12 showing the cartridge container in the containment configuration and in contact with the sled and the gear mechanism in contact with the sled.
Figure 15:
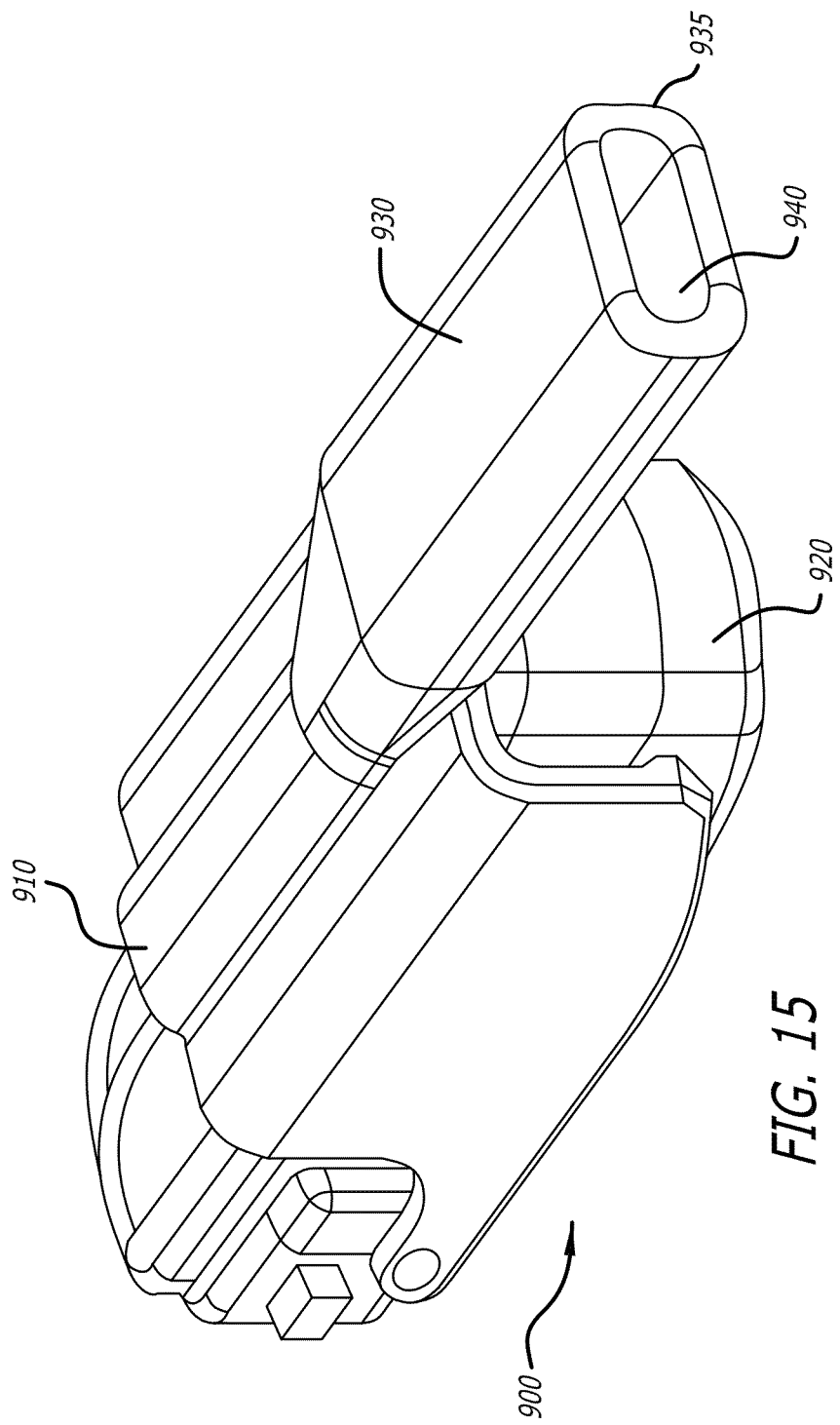
FIG. 15 illustrates a perspective view of the inhaler in FIG. 10 in the closed configuration and with a cartridge in the holder.
Figure 16:
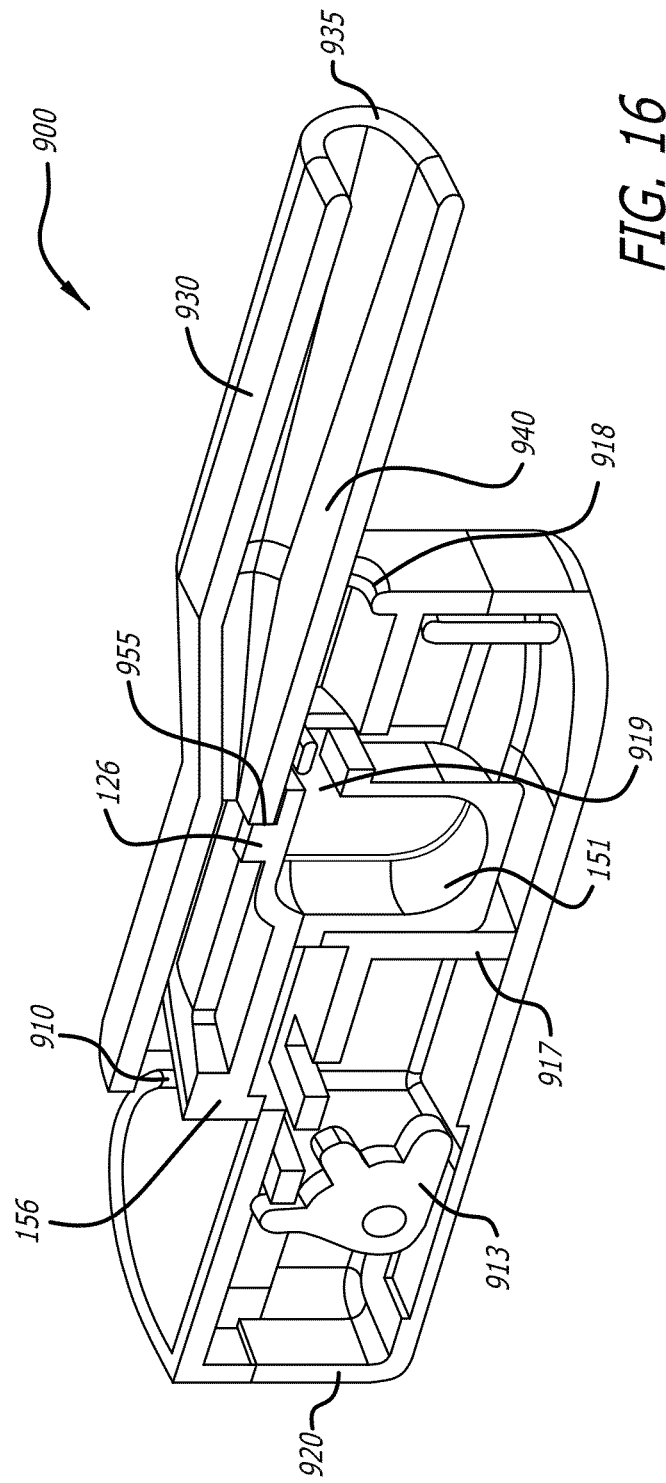
FIG. 16 illustrates a mid-longitudinal section of the inhaler depicted in FIG. 53 showing the cartridge container in the dosing configuration and the air flow pathway established through the container.

FIG. 12 illustrates the housing subassembly 920 comprising two parts manufactured to make an enclosure and comprising a top portion having a cartridge placement or mounting area 908 and a notch 918 which is configured to define an air inlet when the inhaler is in a closed configuration. FIG. 12 illustrates housing 920 as an enclosure, further comprising two component parts for ease of manufacturing, although less or more parts can be used. The bottom portion of the housing forming has no openings and includes a tray 922 and is connected to the top portion or cover 925 to form an enclosure or housing 920. Tray 922 is configured with notches 914 configured near its distal end which houses bar, cylinder or tube 911 in forming a hinge with mouthpiece 930. Tray 922 also houses sled 917. Sled 917 is configured to be movable within tray 922 and has a cartridge receiving area 921 and an arm-like structure having openings 915 for engaging the teeth or gear 913 of mouthpiece 930 so that in closing the device for use, movement of mouthpiece 930 relative to housing 920 moves the sled in a proximal direction, which results in the sled abutting a cartridge container seated on inhaler holder or mounting area 908 and can translocate the container from a containment position to a dosing position. In this embodiment, a cartridge seated in the cartridge holder 908 has the air inlet opening in a dosing configuration facing towards the proximal end of the inhaler or the user. Housing cover 925 is configured so that it can securely attach to tray 922 by having, for example, protrusions 926 extending from the bottom border as a securing mechanism. FIG. 12 illustrates inhaler 900 in the open configuration depicting the position and orientation of a cartridge 150 in a containment configuration to be installed in the mounting area of the inhaler. FIG. 13 further illustrates inhaler 900 in the open configuration with cartridge 150 seated in the cartridge holder in the containment configuration. FIG. 14 illustrates a mid-longitudinal section of the inhaler in FIG. 13 showing the position of the gear 913 relative to sled 917 in the containment configuration of the cartridge container 151, which abuts sled 917. In this embodiment, container 151 moves relative to cartridge top 156. Upon closing inhaler 900 (FIG. 15) and as mouthpiece 930 moves to attain a closed configuration, sled 917 pushes container 151 until the dosing configuration is attained and mouthpiece aperture 955 slides over cartridge boss 126 so that dispensing ports 127 are in communication with the mouthpiece conduit 940 and an air flow pathway is established for dosing through air inlet aperture 918, cartridge air inlet 919 and dispensing ports 127 in air conduit 940. As seen in FIG. 16, mouthpiece 930 and therefore, air conduit 940 have a relatively tapered, hour-glass shape configuration at approximately mid to distal end. In this embodiment, sled 917 is configured so that when the inhaler is open after use, the sled cannot reconfigure a cartridge to the containment configuration. In some variations of this embodiment, it may be possible or desirable to reconfigure the cartridge depending on the powder medicament used.

In embodiments disclosed herein, inhaler apertures, for example, 355, 955 can be provided with a seal, for example, crushed ribs, conformable surfaces, gaskets, and o-rings to prevent air flow leakage into the system so that the airflow only travels through the cartridge. In other embodiment, to effectuate the seal, the seal can be provided to the cartridge. The inhalers are also provided with one or more zones of deagglomeration, which are configured to minimize build-up of powder or deposition. Deagglomeration zones are provided, for example, in the cartridge, including, in the container and the dispensing ports, and at one or more locations in the air conduit of the mouthpiece.

Cartridge embodiments for use with the inhalers are describe above, such as cartridges 150, 170, illustrated, respectively, in FIGS. 10, 13, 14, 16-21, and in FIGS. 7-9, 22-30. The present cartridges are configured to form an enclosure having at least two configurations and contain a dry powder medicament in a storage, tightly sealed or contained position. In this and other embodiments, the cartridge can be reconfigured within an inhaler from a powder containment position to an inhalation or dosing configuration.

In certain embodiments, the cartridge comprises a lid or top and a container having one or more apertures, a containment configuration and dosing configuration, an outer surface, an inner surface defining an internal volume; and the containment configuration restricts communication to the internal volume and the dispensing configuration forms an air passage through the internal volume to allow an air flow to enter and exit the internal volume in a predetermined manner. For example, the cartridge container can be configured so that an airflow entering the cartridge air inlet is directed across the air outlets within the internal volume to meter the medicament leaving the cartridge so that rate of discharge of a powder is controlled; and wherein airflow in the cartridge can tumble substantially perpendicular to the air outlet flow direction, mix and fluidize a powder in the internal volume prior to exiting through dispensing apertures.

In one embodiment, the cartridge can be coded with one or more indicators, including, label, etching, color, frostings, flanges, ridges, and the like. For example, if color is selected, color pigments of various types, which are compatible with plastics and pharmaceutical formulations or that are pharmaceutically-acceptable, can be incorporated during manufacturing of the cartridge. In this and other embodiments, the color can denote a specific active ingredient or dose strength, for example, a green lid can be indicative of 6 units of an FDKP and insulin formulation. Pharmaceutically acceptable colors can be green, blue, teal, poppy, violet, yellow, orange, etc.

Figure 17:
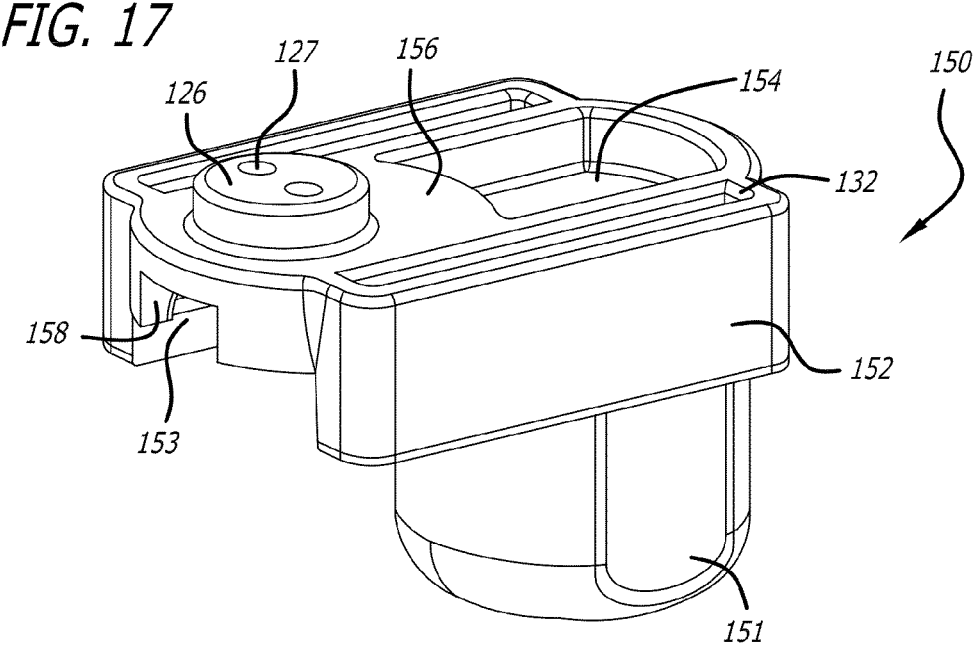
FIG. 17 illustrates a perspective view of a cartridge embodiment for use with the inhaler of FIG. 1 and depicting the cartridge in a containment configuration.
Figure 18:
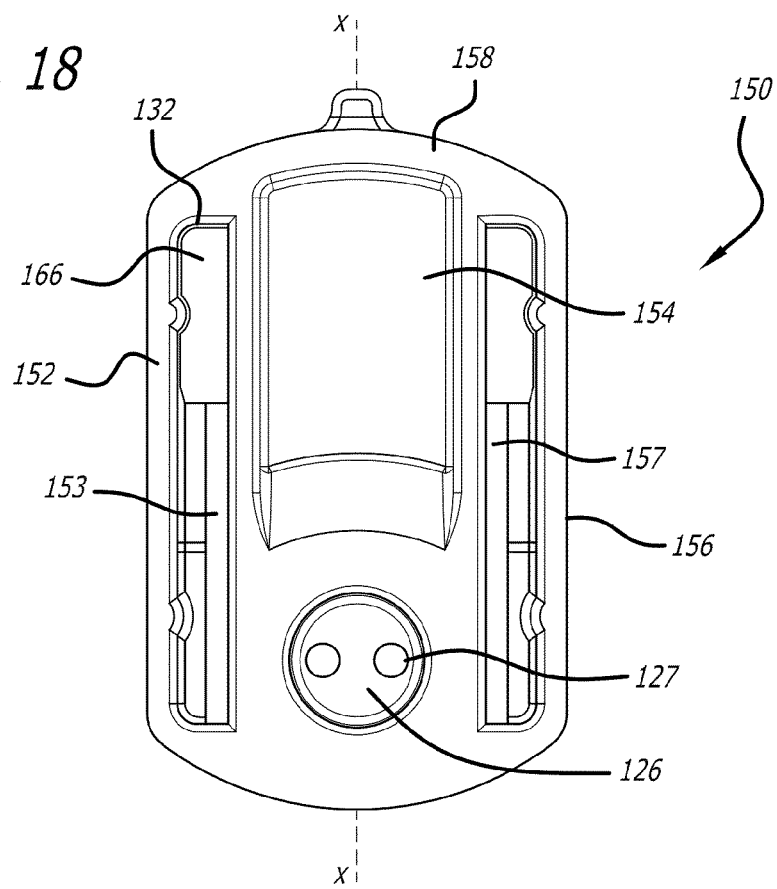
FIG. 18 illustrates a top view of the cartridge embodiment of FIG. 17, showing the component structures of the cartridge top surface.

FIG. 17 further illustrate cartridge 150 comprising top or lid 156 and container 151 defining an interior space or volume. FIG. 18 further exemplifies the cartridge top 156 having opposing ends and comprising recess area 154 and boss 126 at opposing ends of a longitudinal axis X, and relatively rectangular set of panels 152 along the sides and in the longitudinal axis X, which are integrally configured and attached to top 156 at their ends. The border 158 of cartridge top 156 extends downwardly and is continuous with panels 152. Panels 152 extend downwardly from either side of top 156 in the longitudinal axis X and are separated from the area of boss 126 and recess area 154 by a longitudinal space or slit 157. FIGS. 17-21 also show each panel 152 further comprising a flange 153 structurally configured to engage with projections or wings 166 of container 151, support container 151 and allow container 151 to be movable from a containment position under recess area 154 to a dosing position under area of boss 126. Panels 152 are structurally configured with a stop 132 at each end to prevent container 151 from moving beyond their end where they are attached to border 158. In this embodiment, container 151 or lid 156 can be movable, for example, by translational movement upon top 156, or top 156 can be movable relative to the container 151. In one embodiment, container 151 can be movable by sliding on flanges 153 on lid 156 when lid or top 156 is stationary, or lid 156 can be movable by sliding on a stationary container 151 depending on the inhaler configuration. Border 158 near the boss 126 has a recess area which forms part of the perimeter of inlet port 119 in the dosing configuration of the cartridge.

Figure 19:
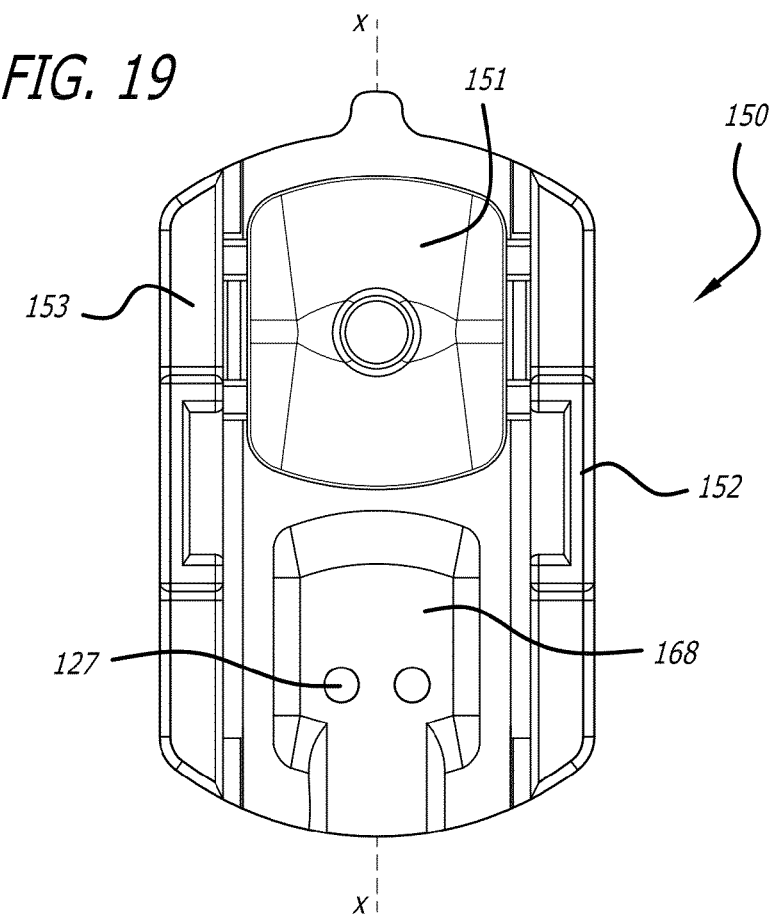
FIG. 19 illustrates a bottom view of the cartridge embodiment of FIG. 17, showing the component structures of the cartridge undersurface.
Figure 20:
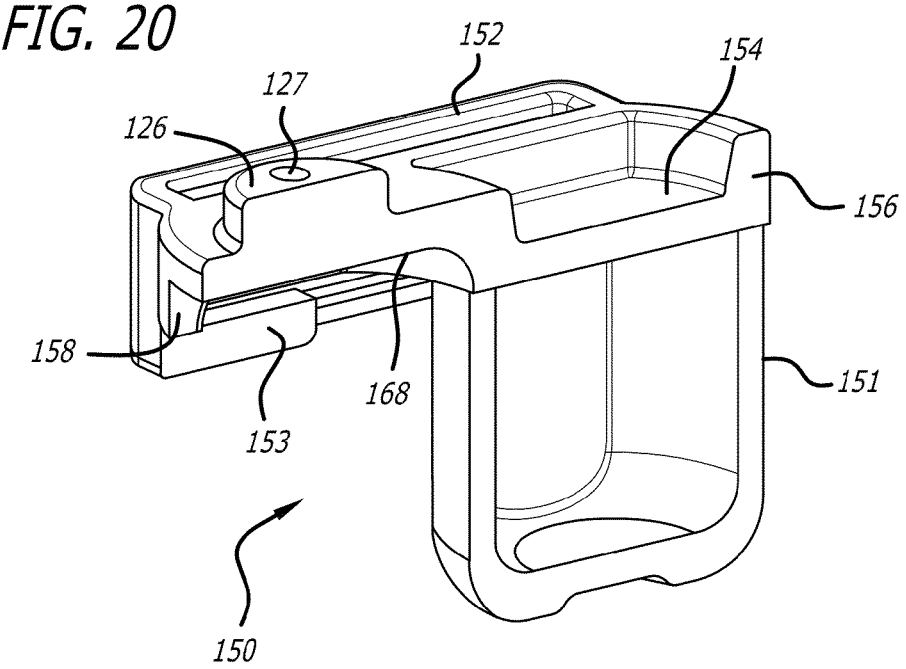
FIG. 20 illustrates a perspective view of a cartridge embodiment of FIG. 17 in mid-longitudinal cross-section and in a containment configuration.
Figure 21:
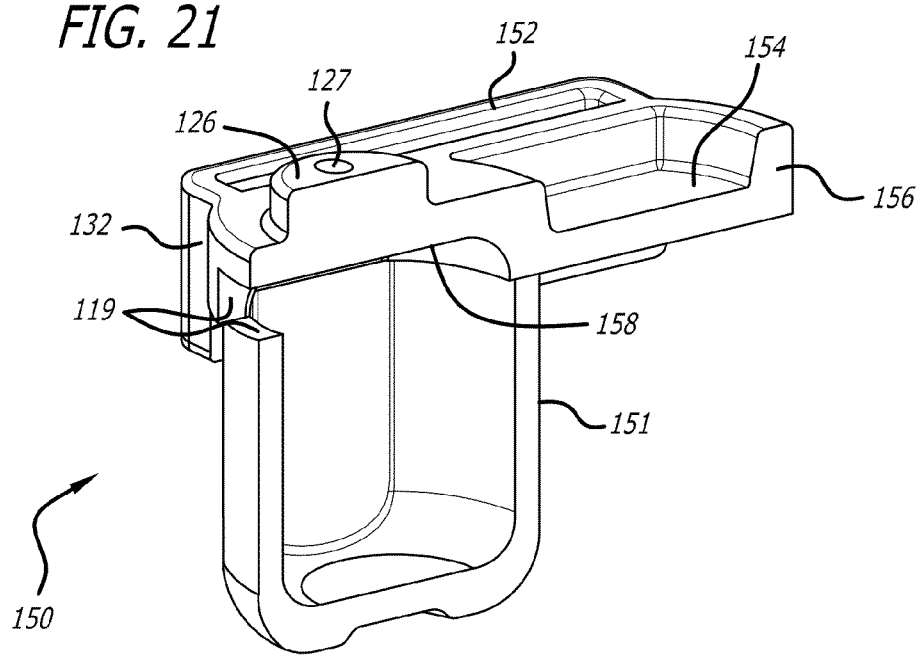
FIG. 21 illustrates a perspective view of a cartridge embodiment of FIG. 17 in a mid-longitudinal cross-section and in a dosing configuration.

FIG. 19 illustrates a bottom view of cartridge 150 showing the relationship of the structures in a containment configuration, such as container 151, dispensing ports 127, panels 152, flanges 153 and area under the boss 126 or undersurface 168 which is relatively hollow or recessed. FIG. 20 illustrates a cross-section through the mid-longitudinal axis X of cartridge 150 in a containment configuration and showing container 151 in tight contact with lid 156 at recess area 154 and supported by flanges 153. The undersurface of the boss 126 is hollow and can be seen relatively at a higher position than the top border of container 151. FIG. 21 illustrates cartridge 150 in a dosing configuration wherein the upper border of container 151 and panel 158 under the area of boss 126 form an inlet port 119 which allows flow entry into the interior of cartridge 151.

Figure 22:
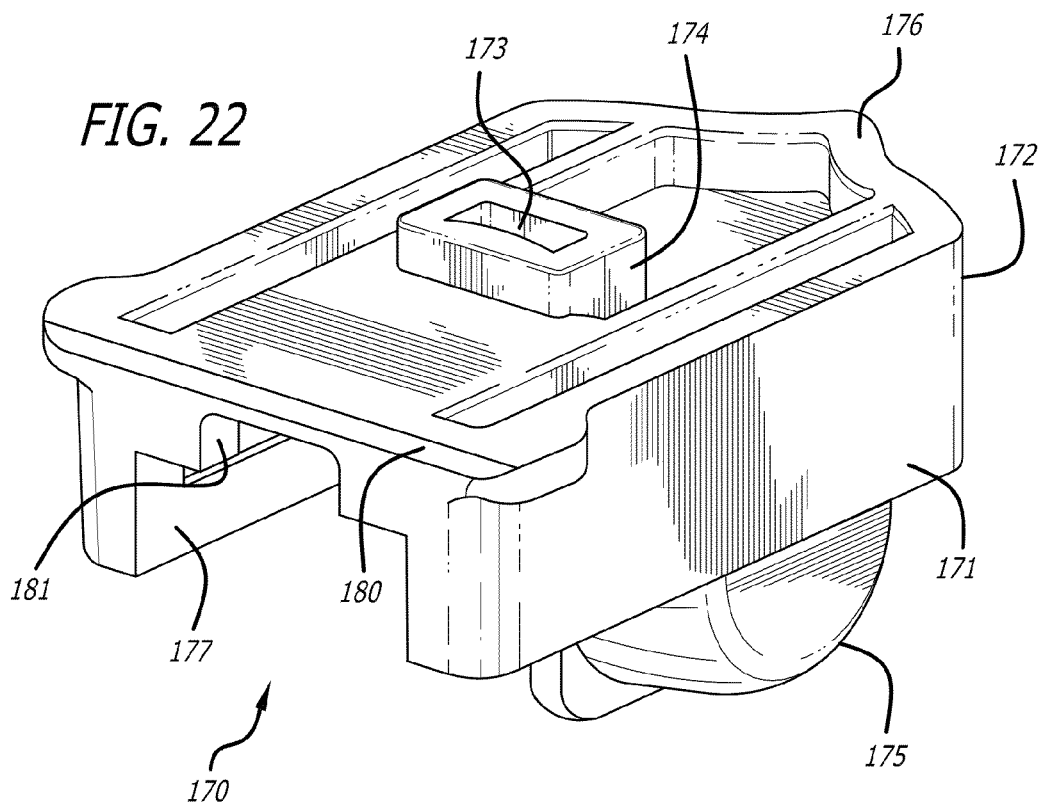
FIG. 22 depicts a perspective view of an alternate embodiment of a cartridge in a containment configuration.

In another embodiment, a translational cartridge 170 is illustrated in FIGS. 22-30, which is an alternate embodiment of cartridge 150 and can be used with, for example, inhaler 302 depicted in FIGS. 1-9. FIG. 22 depicts cartridge 170 comprising an enclosure comprising a top or lid 172 and a container 175 defining an interior space, wherein the cartridge is shown in a containment configuration. In this cartridge configuration, the cartridge top 172 is configured to form a seal with container 175 and container or lid is movable relative to one another. Cartridge 170 can be configured from a containment position (FIGS. 22 and 29) to a dosing position (FIGS. 24-28 and 30) and to a disposable position (not shown), for example, in the middle of the cartridge, to indicate that the cartridge has been used. FIG. 22 also illustrates the various features of cartridge 170, wherein top 172 comprises side panels 171 configured to partially cover the exterior of the container. Each side panel 172 comprises a flange 177 at its lower edge which forms a track to support wing-like structures of container 175, which allows movement of container 175 along the lower border of top 172. The cartridge top 172 further comprises an exterior relatively flat surface at one end, a relatively rectangular boss 174 having an opening or dispensing port 173, and a concave or recess area configured internally to maintain the contents of container 175 in a tight seal. In one embodiment, the dispensing port can be configured to have various sizes, for example, the width and length of the opening can be from about 0.025 cm to about 0.25 cm in width and from about 0.125 cm to about 0.65 cm in length at its entry within the interior of the cartridge. In one embodiment, the dispensing port entry measures approximately 0.06 cm in width to 0.3 cm in length. In certain embodiments, cartridge top 172 can comprise various shapes which can include grasping surfaces, for example, tabs 176, 179 and other configurations to orient the cartridge in the right orientation for proper placement in the holder, and a securing mechanism, for example, a chamfered or beveled edge 180 to adapt securely to a corresponding inhaler. The flanges, external geometry of the boss, tabs, and various other shapes can constitute keying surfaces that can indicate, facilitate, and/or necessitate proper placement of the cartridge in the inhaler. Additionally, these structures can be varied from one inhaler-cartridge pairing system to another in order to correlate a particular medicament or dosage provided by the cartridge with a particular inhaler. In such manner, a cartridge intended for an inhaler associated with a first medicament or dosage can be prevented from being placed into or operated with a similar inhaler associated with a second medicament or dosage.

Figure 23:
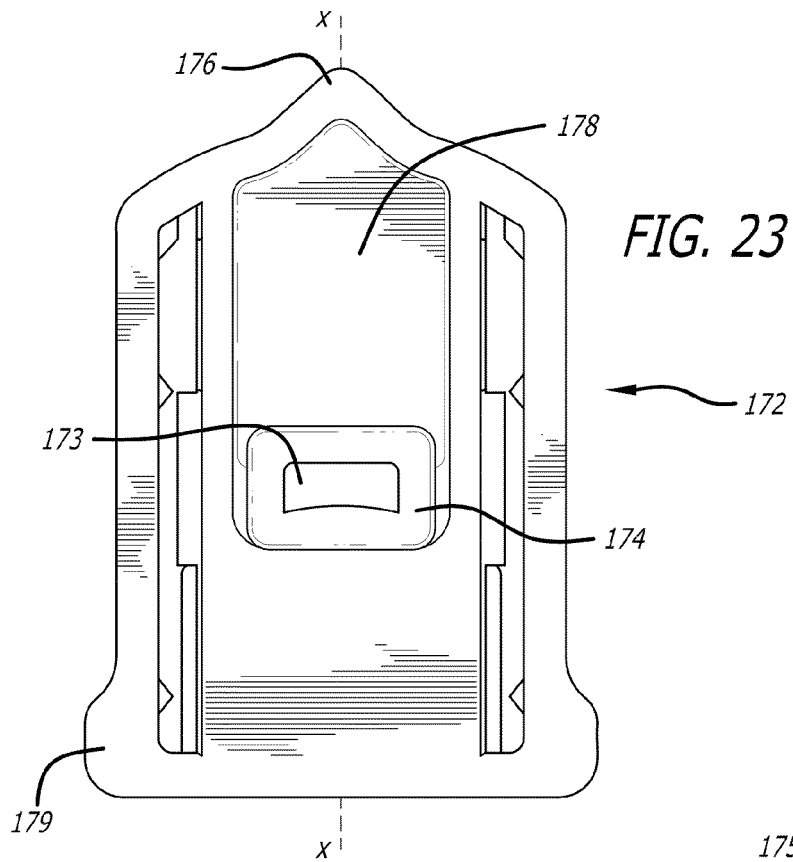
Figure 24:
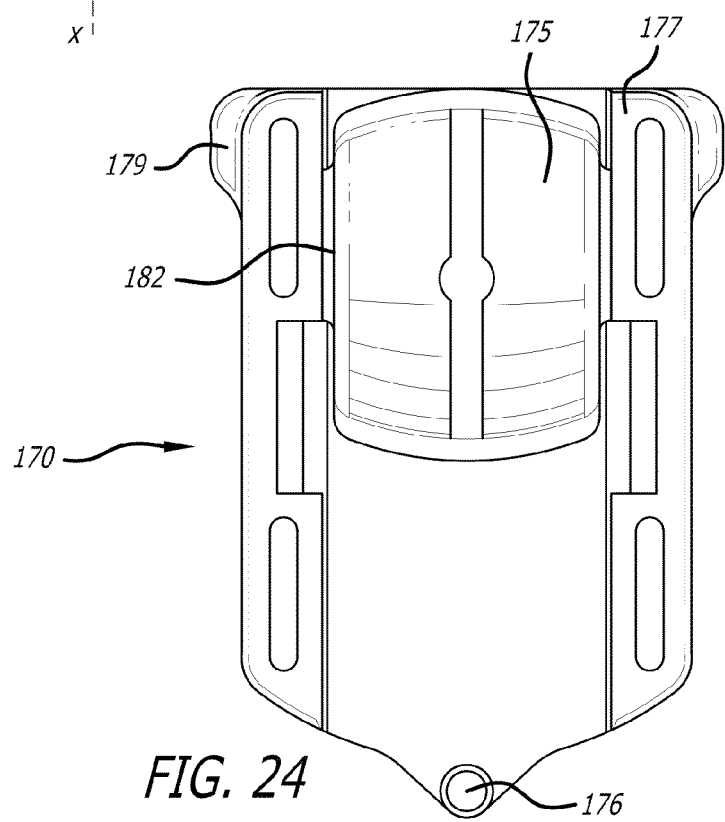

FIG. 23 is a top view of exemplifying the general shape of a cartridge top 172 with boss 174, dispensing port 173, recess area 178 and tabs 176 and 179. FIG. 24 is a bottom view of cartridge 170 showing container 175 in a dosing position being supported by its wing-like projections 182 by each flange 177 from top 172. FIG. 25 depicts cartridge 170 in a dosing configuration further comprising an air inlet 181 formed by a notch on the cartridge top 172 and the container 175 upper border. In this configuration, air inlet 181 is in communication with the interior of the cartridge and forms and air conduit with dispensing port 173. In use, the cartridge air inlet 181 is configured to direct airflow entering the cartridge interior at the dispensing port 173. FIG. 26 depicts the cartridge 170 from the opposite end of the dosing configuration or back view of FIG. 25.

Figure 28:
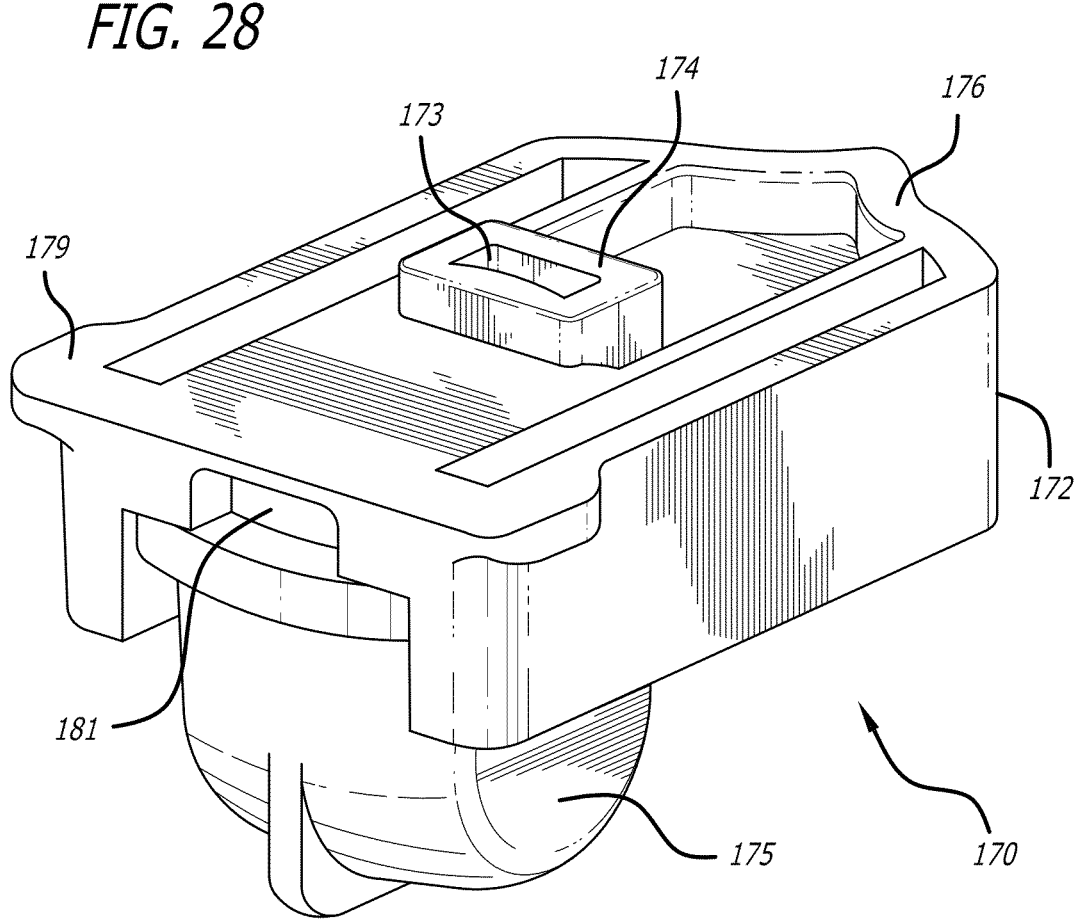
FIG. 28 depicts a perspective view of the cartridge embodiment shown in FIG. 22 in a dosing configuration.
Figure 29:
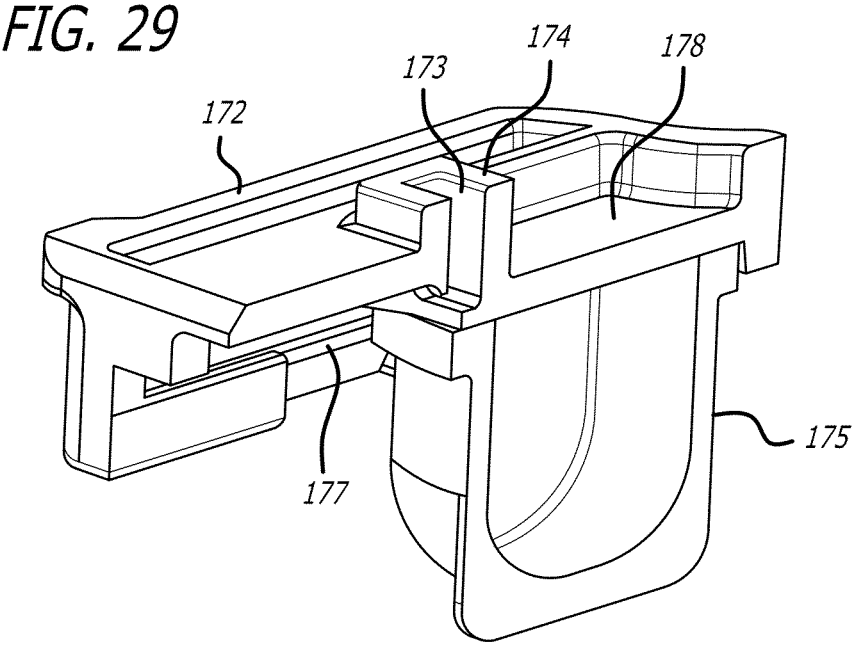
FIGS. 29 and 30 are cross-sections through the longitudinal axis of the cartridge embodiment of FIGS. 22 and 28, respectively.
Figure 30:
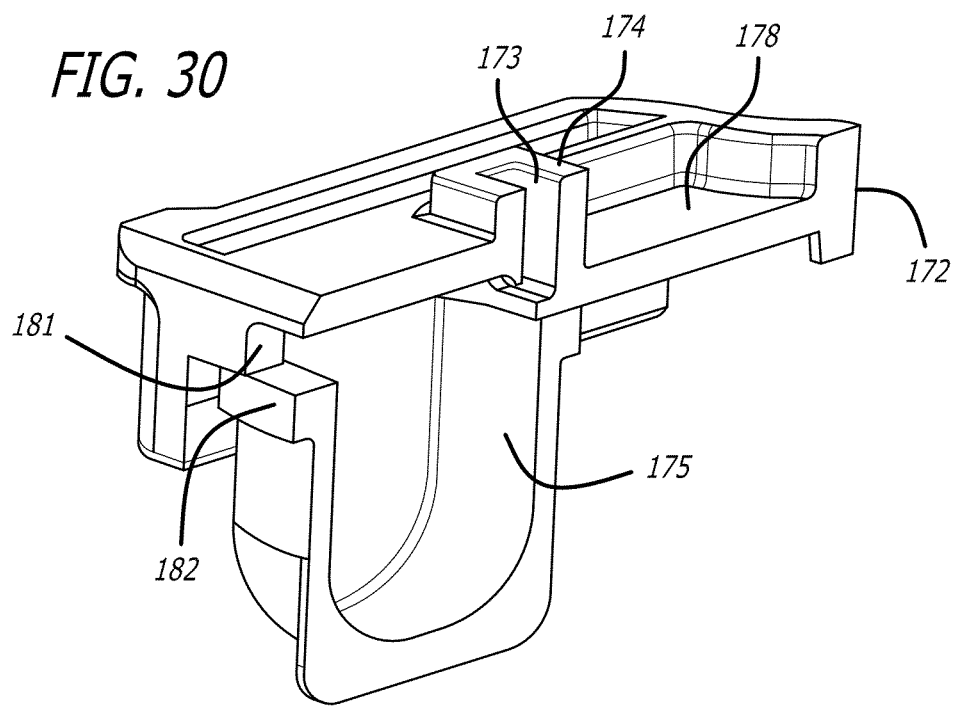

FIG. 27 illustrates a side view of cartridge 150, showing the relationship of the structures in a dosing configuration, such as container 175, boss 174, side panels 172, and tab 176. FIG. 28 illustrates a cartridge 170 in a dosing configuration for use and comprising a container 175 and a top 172 having a relatively rectangular air inlet 181 and a relatively rectangular dispensing port 173 piercing through a boss 174 which is relatively centrally located on the cartridge top 172 upper surface. Boss 174 is configured to fit into an aperture within a wall of a mouthpiece of an inhaler. FIGS. 29 and 30 illustrate cross-sections through the mid-longitudinal axis X of cartridge 170 in a containment configuration and dosing configuration, respectively, showing container 175 in contact with the lid 172 undersurface of the recess area 178 and supported by flanges 177 which form tracks for the container to slide from one position to another. As shown in FIG. 29, in the containment configuration, container 175 forms a seal with the undersurface of the cartridge top 172 at recess area 178. FIG. 30 depicts the cartridge 170 in the dosing configuration wherein the container is at opposing end of the recess area 181 and the container 175 and cartridge top form an air inlet 181 which allows ambient air to enter cartridge 170 as well as to form an air conduit with dispensing port 173 and the interior of container 175. In this embodiment, the cartridge top undersurface wherein the dosing position is attained is relatively flat and container 175 interior surface is configured to have somewhat of a U-shape. The boss 174 is configured to slightly protrude above the top surface of cartridge top 172.

In other embodiments of the cartridge, the cartridge can be adapted to the dry powder inhalers which are suitable for use with an inhaler with a rotatable mechanism for moving the inhaler or cartridge from a containment configuration to a dosing position, wherein the cartridge top is movable relative to the container, or for moving the container relative to the top in achieving alignment of the dispensing ports with the container to a dosing position, or moving either the container or the top to the containment configuration.

In embodiments described herein, cartridges can be configured to deliver a single unit, pre-metered dose of a dry powder medicament in various amounts depending on the dry powder formulation used. Cartridge examples such as cartridge 150, 170 can be structurally configured to contain a dose of, for example, from 0.1 mg to about 50 mg of a dry powder formulation. Thus the size and shape of the container can vary depending on the size of the inhaler and the amount or mass of powder medicament to be delivered. For example, the container can have a relatively cylindrical shape with two opposing sides relatively flat and having an approximate distance between of from about 0.4 cm to about 2.0 cm. To optimize the inhaler performance, the height of the inside of the cartridge along the Y axis may vary depending on the amount of powder that is intended to be contained within the chamber. For example, a fill of 5 mg to 15 mg of powder may optimally require a height of from about 0.6 cm to about 1.2 cm.

In an embodiment, a medicament cartridge for a dry powder inhaler is inhaler is provided, comprising: an enclosure configured to hold a medicament; at least one inlet port to allow flow into the enclosure, and at least one dispensing port to allow flow out of the enclosure; the at least one inlet port is configured to direct at least a portion of the flow entering the at least one inlet port at the at least one dispensing port within the enclosure in response to a pressure differential. In one embodiment, the inhaler cartridge is formed from a high density polyethylene plastic. The cartridge has a container which has an internal surface defining an internal volume and comprising a bottom and side walls contiguous with one another, and having one or more openings. The can have a cup-like structure and has one opening with a rim and it is formed by a cartridge top and a container bottom which are configurable to define one or more inlet ports and one or more dispensing ports. The cartridge top and container bottom are configurable to a containment position, and a dispensing or dosing position.

In embodiments described herein, a dry powder inhaler and cartridge form an inhalation system which can be structurally configured to effectuate a tunable or modular airflow resistance, as the system can be effectuated by varying the cross-sectional area at any section of its airflow conduits. In one embodiment, the dry powder inhaler system can have an airflow resistance value of from about 0.065 to about 0.200 ($\sqrt{kPa}$)/liter per minute. In other embodiments, a check valve may be employed to prevent air flow through the inhaler until a desired pressure drop, such as 4 kPa has been achieved, at which point the desired resistance reaches a value within the range given herewith.

Figure 31:
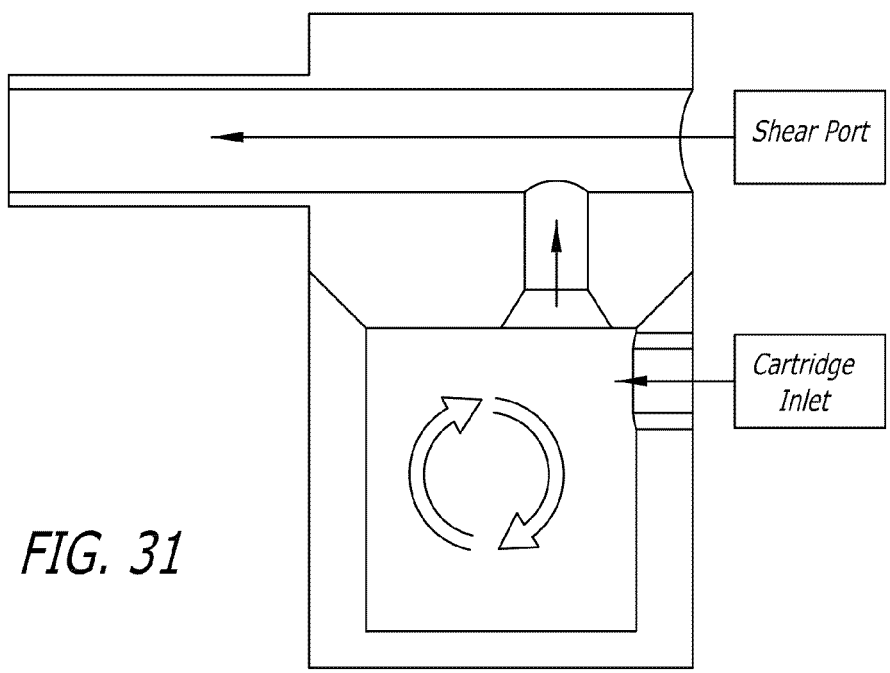
FIG. 31 is a schematic representation of the movement of flow within the powder containment area of a dry powder inhaler as indicated by the arrows.
Figure 32:
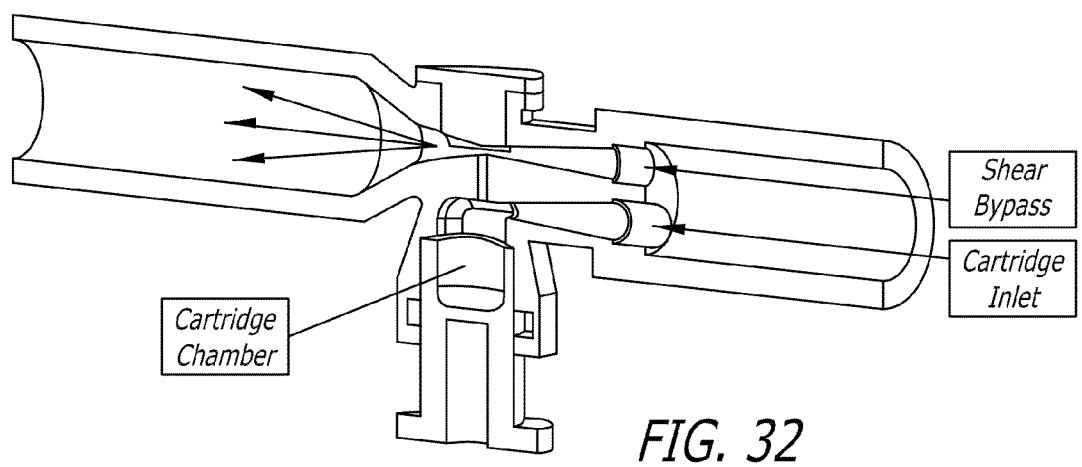
FIG. 32 is a schematic representation of an embodiment of a dry powder inhaler showing the flow pathways and direction of flow through the inhaler as indicated by the arrows.
Figure 33:
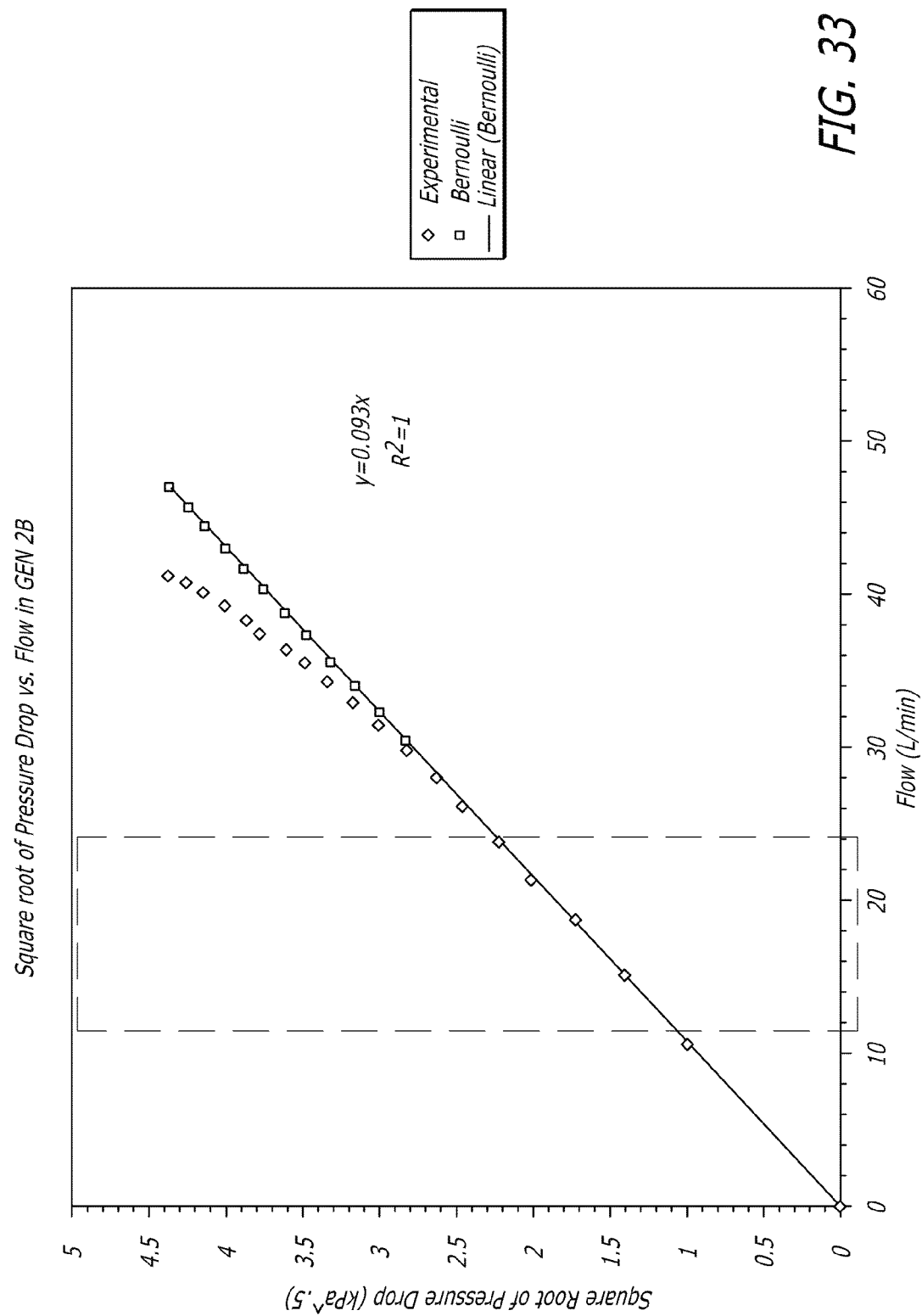
FIG. 33 illustrates a graph of measurements of flow and pressure relationship based on the Bernoulli principle for an exemplary embodiment of the resistance to flow of an inhaler.

In the embodiments disclosed herein, the dry powder inhaler system is configured to have a predetermined flow balance distribution in use, having a first flow pathway through the cartridge and second flow pathway through, for example, the mouthpiece air conduit. FIG. 31 and FIG. 32 depict a schematic representation of air conduits established by the cartridge and inhaler structural configurations which direct the balance of flow distribution. FIG. 31 depicts the general direction of flow within a cartridge in the dispensing or dosing position of a dry powder inhaler as shown by the arrows. FIG. 32 illustrates the movement of flow of an embodiment of a dry powder inhaler showing the flow pathways of the inhaler in the dosing position as indicated by the arrows.

The balance of mass flow within an inhaler is approximately 20% to 70% of the volume going through the cartridge flow pathway, and about 30% to 90% through the beginning portion of the mouthpiece conduit. In this embodiment, the airflow distribution through the cartridge mixes the medicament in a tumbling manner to fluidize or aerosolize the dry powder medicament in the cartridge container. Airflow fluidizing the powder within the container then lifts the powder and gradually lets the powder particles exit the cartridge container through the dispensing ports, then shear from the airflow entering the mouthpiece conduit converges with the airflow containing medicament emanating from the cartridge container. Predetermined or metered exiting airflow from the cartridge converge with bypass airflow entering the air conduit of the mouthpiece to further dilute and deagglomerate the powder medicament prior to exiting the mouthpiece outlet port and entering the patient.

In yet another embodiment, an inhalation system for delivering a dry powder formulation to a patient is provided, comprising an inhaler comprising a container mounting area configured to receive a container, and a mouthpiece having at least two inlet apertures and at least one exit aperture; wherein one inlet aperture of the at least two inlet apertures is in fluid communication with the container area, and one of the at least two inlet apertures is in fluid communication with the at least one exit aperture via a flow path configured to bypass the container area to deliver the dry powder formulation to the patient; wherein the flow conduit configured to bypass the container area delivers 30% to 90% of the total flow going through the inhaler during an inhalation.

In another embodiment, an inhalation system for delivering a dry powder formulation to a patient is also provided, comprising a dry powder inhaler comprising a container region and a container; the dry powder inhaler and container combined are configured to have rigid flow conduits in a dosing configuration and a plurality of structural regions that provide a mechanism for powder deagglomeration of the inhalation system in use; wherein at least one of the plurality of mechanisms for deagglomeration is an agglomerate size exclusion aperture in the container region having a smallest dimension between 0.25 mm and 3 mm. The term "rigid flow conduits" denotes air conduits of the inhalation system that do not change in geometry after repeated use, i.e., the conduits remain the same or constant and are not variable from use to use, as opposed to systems which operate with puncturing mechanisms for use with capsules and blisters which may exhibit variability in conduit configuration from capsule to capsule or blister to blister.

In an alternate embodiment, an inhalation system for delivering a dry powder formulation to a patient is provided, comprising a dry powder inhaler comprising a mouthpiece and a container; the dry powder inhaler and container combined are configured to have rigid flow conduits in a dosing configuration and a plurality of structural regions that provide a mechanism for powder deagglomeration of the inhalation system in use; wherein at least one of the plurality of mechanisms for deagglomeration is an air conduit configured in the mouthpiece which directs flow at an exit aperture in fluid communication with the container. In particular embodiments, the inhalation system includes a container further comprising a mechanisms for cohesive powder deagglomeration which comprises a cup-like structure configured to guide a flow entering the container to rotate, re-circulating in the internal volume of the cup-like structure and lifting up a powder medicament so as to entrain the powder agglomerates in the flow until the powder mass is small enough prior to exiting the container. In this embodiment, the cup-like structure has one or more radii configured to prevent flow stagnation.

In embodiments describe herein, the cartridge is structurally configured having the inlet opening in close proximity to the dispensing ports in a horizontal and vertical axis. For example, the proximity of the inlet to the dispensing ports can be immediately next to the air inlet to about within one cartridge width, although this relationship can vary depending on the flow rate, the physical and chemical properties of the powder. Because of this proximity, flow from the inlet crosses the opening to the dispensing ports within the cartridge creating a flow configuration that inhibits fluidized powder or powder entrained within the airflow, from exiting the cartridge. In this manner, during an inhalation maneuver, flow entering the cartridge container can effectuate tumbling of the dry powder formulation in the cartridge container, and fluidized powder approaching the exit or dispensing ports of a cartridge can be impeded by flow entering the inlet port of the cartridge, thereby, flow within the cartridge can be restricted from exiting the cartridge container. Due to differences in inertia, density, velocity, charge interaction, position of the flow, only certain particles can navigate the path needed to exit the dispensing ports. Particles that do not pass through the exit port must continue to tumble until they possess the proper mass, charge, velocity or position. This mechanism, in effect, can meter the amount of medicament leaving the cartridge and can contribute to deagglomeration of powder. To further help meter the exiting fluidized powder, the size and number of dispensing ports can be varied. In one embodiment, two dispensing ports are used, configured to be circular in shape, each 0.10 cm in diameter and positioned near the inlet aperture about middle center line of the container to about 0.2 cm from the centerline towards the air inlet port. Other embodiments can, for example, have dispensing ports of various shapes including rectangular wherein the cross-sectional area of the one or more dispensing ports ranges from 0.05 cm$^2$ to about 0.25 cm$^2$. In some embodiments, the sizes ranging of the dispensing ports can be from about 0.05 cm to about 0.25 cm in diameter. Other shapes and cross-sectional areas can be employed as long as they are similar in cross-sectional area to the values given herewith. Alternatively, for more cohesive powders larger cross sectional area of the dispensing port can be provided. In certain embodiments, the cross sectional area of the dispensing port can be increased depending on the size of the agglomerates relative to the minimum opening dimension of the port or ports so that the length relative to the width of the port remains large. In one embodiment, the intake aperture is wider in dimension than the width of the dispensing port or ports. In embodiments wherein the intake aperture is rectangular, the air inlet aperture comprises a width ranging from about 0.2 cm to about the maximal width of the cartridge. In one embodiment the height is about 0.15 cm, and width of about 0.40 cm. In alternate embodiments, the container can have a height of from about 0.05 cm to about 0.40 cm. In particular embodiments, the container can be from about 0.4 cm to about 1.2 cm in width, and from about 0.6 cm to about 1.2 cm in height. In an embodiment, the container comprise one or more dispensing ports having and each of the ports can have a diameter between 0.012 cm to about 0.25 cm.

In particular inhalation systems, a cartridge for a dry powder inhaler, comprising a cartridge top and a container is provided, wherein the cartridge top is configured relatively flat and having one or more openings and one or more flanges having tracks configured to engage the container; the container having an inner surface defining an internal volume and is moveably attached to the tracks on the one or more flanges on the cartridge top and configurable to attain a containment position and a dispensing or dosing position by moving along the tracks of the one or more flanges.

In another embodiment, the inhalation system comprises an enclosure having one or more exit ports configured to exclude a powder mass of a dry powder composition having a smallest dimension greater than 0.5 mm and less than 3 mm. In one embodiment, a cartridge for a dry powder inhaler, comprising an enclosure having two or more rigid parts; the cartridge having one or more inlet ports and one or more dispensing ports, wherein one or more inlet ports have a total cross-sectional area which is larger than the total cross-sectional area of the dispensing ports, including wherein the total cross-sectional area of one or more dispensing ports ranges from 0.05 cm$^2$ to about 0.25 cm$^2$.

In one embodiment, a method for deagglomerating and dispersing a dry powder formulation for inhalation, comprising the steps of: generating an airflow in a dry powder inhaler comprising a mouthpiece and a container having at least one inlet port and at least one dispensing port and containing a dry powder formulation; the container forming an air conduit between the at least one inlet port and the at least one dispensing port and the inlet port directs a portion of the airflow entering the container to the at least one dispensing port; allowing airflow to tumble powder within the container so as to lift and mix the dry powder medicament in the container to form an airflow medicament mixture; and accelerating the airflow exiting the container through the at least one dispensing port. In this embodiment, the powder medicament that passes through the dispensing ports can immediately accelerate due to reduction in cross-sectional area of the exit ports relative to the inlet port. This change in velocity may further deagglomerate the fluidized and aerosolized powder medicament during inhalation. Additionally, because of the inertia of the particles or groups of particles in the fluidized medicament, the velocity of the particles leaving the dispensing ports is not the same. The faster moving air flow in the mouthpiece conduit imparts a drag or shear force on each particle or group of particles of the slower moving fluidized powder leaving the exit or dispensing port or ports, which can further deagglomerate the medicament.

The powder medicament that passes through the dispensing port or ports immediately accelerates due to reduction in cross-sectional area of the exit or dispensing ports relative to the container, which are designed to be narrower in cross-sectional area than the air inlet of the container. This change in velocity may further deagglomerate the fluidized powder medicament. Additionally, because of the inertia of the particles or groups of particles in the fluidized medicament, the velocity of the particles leaving the dispensing ports and the velocity of the flow passing the dispensing ports is not the same.

In embodiments described herein, powder exiting the dispensing ports can further accelerate, for example, by an imparted change in direction and/or velocity of the fluidized medicament. Directional change of fluidized powder leaving the dispensing port and entering the mouthpiece conduit can occur at an angle of approximately 0° to about 180°, for example approximately 90°, to the axis of the dispensing port. Change in flow velocity and direction may further deagglomerate the fluidized powder through the air conduits. The change in direction can be accomplished through geometric configuration changes of the air flow conduit and/or by impeding the air flow exiting the dispensing ports with a secondary air flow entering the mouthpiece inlet. The fluidized powder in the mouthpiece conduit expands and decelerates as it enters the oral placement portion of the mouthpiece prior to exiting due to a cross-sectional area increase in the conduit. Gas trapped within agglomerates also expands and may help to break apart the individual particles. This is a further deagglomeration mechanism of the embodiments described herein. Airflow containing medicament can enter the patient's oral cavity and be delivered effectively, for example, into the pulmonary circulation.

Each of the deagglomeration mechanisms described herein and part of the inhalation system represent a multi-stage approach which maximizes powder deagglomeration. Maximal deagglomeration and delivery of powder can be obtained by optimizing the effect of each individual mechanism, including, one or more acceleration/deceleration conduits, drag, or expansion of gas trapped within the agglomerates, interactions of powder properties with those of the inhaler components material properties, which are integral characteristics of the present inhaler system. In the embodiments described herein, the inhalers are provided with relatively rigid air conduits or plumbing system to maximize deagglomeration of powder medicament so that there is consistency of the powder medicament discharge from the inhaler during repeated use. Since the present inhalers are provided with conduits which are rigid or remain the same and cannot be altered, variations in the air conduit architecture resulting from puncturing films or peeling films associated with prior art inhalers using blister packs are avoided.

In one embodiment, there is provided a method of deagglomerating a powder formulation in a dry powder inhalation system, comprising: providing the dry powder formulation in a container having an internal volume to a dry powder inhaler; allowing a flow to enter the container which is configured to direct a flow to lift, entrain and circulate the dry powder formulation until the powder formulation comprises powder masses sufficiently small to pass through one or more dispensing apertures into a mouthpiece. In this embodiment, the method can further comprise the step of accelerating the powder masses entrained in the flow leaving the one or more dispensing apertures and entering the mouthpiece.

In embodiments disclosed herein, a dry powder medicament is dispensed with consistency from the inhaler in less than about 2 seconds. The present inhaler system has a high resistance value of approximately 0.065 to about 0.20 (√kPa)/ liter per minute. Therefore, in the inhalation system comprising a cartridge, peak inhalation pressure drops of between 2 and 20 kPa produce resultant peak flow rates of about through the system of between 7 and 70 L/min. In some embodiments, the pressure differential for the inhaler and cartridge system can be below 2 kPa. These flow rates result in greater than 75% of the cartridge contents dispensed in fill masses between 1 and 30 mg of powder or greater amounts. In some embodiments, these performance characteristics are achieved by end users within a single inhalation maneuver to produce cartridge dispense percentage of greater than 90%. In other embodiments, these performance characteristics are achieved by end users within a single inhalation maneuver to produce cartridge dispense percentage of about 100%. In certain embodiments, the inhaler and cartridge system are configured to provide a single dose by discharging powder from the inhaler as a continuous flow of powder delivered to a patient. In some embodiments, it may be possible to configure the inhalation system to deliver powder in use as one or more pulses of powder discharge depending on the particle sizes. In one embodiment, an inhalation system for delivering a dry powder formulation to a patient's lungs is provided, comprising a dry powder inhaler configured to have flow conduits with a total resistance to flow in a dosing configuration ranging in value from about 0.065 to about 0.200 (√kPa)/liter per minute. In this and other embodiments, the total resistance to flow of the inhalation system is relatively constant across a pressure differential range of between 0.5 kPa and 7 kPa.

The structural configuration of the inhalation system allows the deagglomeration mechanism to produce respirable fractions greater than 50% and particles of less than 5.8 µm. The inhalers can discharge greater than 85% of a powder medicament contained within a container during an inhalation maneuver. Generally, the inhalers herein depicted in FIG. 151 can discharge greater that 90% of the cartridge or container contents in less than 3 seconds at pressure differentials between 2 and 5 kPa with fill masses ranging up to 30 mg.

In another embodiment, the present systems have a lower limit of performance. This performance limit is assigned based on inhatation of a dry powder as described herein where a median particular particle size distribution is attained. A graph of PIP versus AUC can be formed where a triangular area exists where PIP values are physically impossible to attain for a device given the AUC values. However, an acceptable area can be formed based on a horizontal and vertical lines representing passing criteria. The inhalation systems described herein have a lower limit for acceptable performance of a PIP of about 2 kPa and an AUC of at least about 1.0, 1.1 or 1.2 kPa*sec.

In other embodiments, a lower limit and an upper limit for AUC exist. For example, AUC can range from about 1.0 to about 15 kPa*sec, from about 1.0 to about 10 kPa*sec, form about 1.1 to about 15 kPa*sec, from about 1.2 to about 10 kPa*sec, from about 1.2 to about 15 kPa*sec, or from about 1.2 to about 10 kPa*sec.

In another embodiment, adequately de-agglomerated doses of a dry powder medicament using a high resistance dry powder inhaler are accomplished by providing a high resistance dry powder inhaler containing a dose of the dry powder medicament; inhaling from the inhaler with sufficient force to reach a peak inspiratory pressure of at least 2 kPa within 2 seconds; and generating an area under the curve in the first second ($AUC_{0-1sec}$) of a inspiratory pressure-time curve of at least about 1.0, 1.1, or 1.2 kPa*second; wherein VMGD (×50) of the emitted powder is less than about 5 um. In some embodiments a patient exerts a peak inspiratory pressure in two (2) seconds (PIP2 seconds) of greater than or equal to 2 kPa and less than or equal to 15 or 20 kPa. In another embodiment, the dry powder medicament includes microparticles with a median particle size VMGD (×50) of the emitted powder particles is not greater than 1.33 times the median particle size when the inhaler is used optimally. In this and other embodiments, optimal inhaler use by a patient is when a patient exerts a peak inspiratory pressure in two (2) seconds (PIP2 seconds) of about 6 kPa. Optimal use can also be recognized by achieving a flow rate of approximately 28.3 L per minute. Similarly optimal usage can be that reflecting standard test conditions for aerodynamic particle size testing as specified, for example, in USP <601>.

The high resistance dry powder inhaler, in some embodiments, comprises a dose of a dry powder medicament is inhaled by the patient with sufficient force (or effort) to reach a peak inspiratory pressure of at least 2 kPa within 2 seconds; and generating an area under the curve in the first second ($AUC_{0-1sec}$) of a inspiratory pressure versus time curve of at least about 1.0, 1.1 or 1.2 kPa*sec; wherein greater than 75% of the dry powder dose is discharged or emitted from the inhaler as powder particles. In some embodiments the VMGD of the emitted particles is less than about 5 microns.

Adequately de-agglomerated doses of a dry powder medication using a high resistance dry powder inhaler can be achieved by providing a high resistance dry powder inhaler containing a dose of a dry powder medicament; inhaling from the inhaler with sufficient force to reach a peak inspiratory pressure of at least 2 kPa within 2 seconds; and generating an area under the curve in the first second ($AUC_{0-1sec}$) of a inspiratory pressure-time curve of at least about 1.0, 1.1, or 1.2 kPa*second; where n VMGD (×50) of the emitted powder is less than about 5 um. In another embodiment, the dry powder medicament includes microparticles with a median particle size VMGD (×50) of the emitted powder particles is not greater than 1.33 times the median particle size when the inhaler is used optimally.

While the present inhalers are primarily described as breath-powered, in some embodiments, the inhaler can be provided with a source for generating the pressure differential required to deagglomerate and deliver a dry powder formulation. For example, an inhaler can be adapted to a gas powered source, such as compressed gas stored energy source, such as from a nitrogen can, which can be provided at the air inlet ports. A spacer can be provided to capture the plume so that the patient can inhale at a comfortable pace.

In embodiments described herewith, the inhaler can be provided as a reusable inhaler or as a single use inhaler. In alternate embodiments, a similar principle of deagglomeration can be adapted to multidose inhalers, wherein the inhaler can comprise a plurality of, for example, cartridge like structures in a single tray and a single dose can be dialed as needed. In variations of this embodiment, the multidose inhaler can be configured to provide enough doses, for example, for a day, a week or a month's supply of a medication. In the multidose embodiments described herein, end-user convenience is optimized. For example, in prandial regimens, breakfast, lunch and dinner dosing is achieved with a system configured to provide dosing for a course of 7 days in a single device. Additional end-user convenience is provided by a system configured with an indicator mechanism that indicates the day and dosing, for example, day 3 (D3), lunchtime (L).

In one embodiment, the dry powder medicament may comprise, for example, a diketopiperazine and a pharmaceutically active ingredient. In this embodiment, the pharmaceutically active ingredient or active agent can be any type depending on the disease or condition to be treated. In another embodiment, the diketopiperazine can include, for example, symmetrical molecules and asymmetrical diketopiperazines having utility to form particles, microparticles and the like, which can be used as carrier systems for the delivery of active agents to a target site in the body. The term 'active agent' is referred to herein as the therapeutic agent, or molecule such as protein or peptide or biological molecule, to be encapsulated, associated, joined, complexed or entrapped within or adsorbed onto the diketopiperazine formulation. Any form of an active agent can be combined with a diketopiperazine. The drug delivery system can be used to deliver biologically active agents having therapeutic, prophylactic or diagnostic activities.

One class of drug delivery agents that has been used to produce microparticles that overcome problems in the pharmaceutical arts such as drug instability and/or poor absorption, are the 2,5-diketopiperazines. 2,5-diketopiperazines are represented by the compound of the general Formula 1 as shown below wherein the ring atoms $E_1$ and $E_2$ at positions 1 and 4 are either O or N to create the substitution analogs diketomorpholine and diketodioxane, respectively, and at least one of the side-chains $R_1$ and $R_2$ located at positions 3 and 6 respectively contains a carboxylic acid (carboxylate) group. Compounds according to Formula 1 include, without limitation, diketopiperazines, diketomorpholines and diketodioxanes and their substitution analogs.

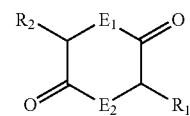

Formula 1

As used herein, "a diketopiperazine" or "a DKP" includes diketopiperazines and pharmaceutically acceptable salts, derivatives, analogs and modifications thereof falling within the scope of the general Formula 1.

These 2,5 diketopiperazines have been shown to be useful in drug delivery, particularly those bearing acidic $R^1$ and $R^2$ groups (see for example U.S. Pat. No. 5,352,461 entitled "Self Assembling Diketopiperazine Drug Delivery System;" U.S. Pat. No. 5,503,852 entitled "Method For Making Self-Assembling Diketopiperazine Drug Delivery System;" U.S. Pat. No. 6,071,497 entitled "Microparticles For Lung Delivery Comprising Diketopiperazine;" and U.S. Pat. No. 6,331,318 entitled "Carbon-Substituted Diketopiperazine Delivery System," each of which is incorporated herein by reference in its entirety for all that it teaches regarding diketopiperazines and diketopiperazine-mediated drug delivery). Diketopiperazines can be formed into drug adsorbing microparticles. This combination of a drug and a diketopiperazine can impart improved drug stability and/or absorption characteristics. These microparticles can be administered by various routes of administration. As dry powders these microparticles can be delivered by inhalation to specific areas of the respiratory system, including the lung.

The fumaryl diketopiperazine (3,6-bis(N-fumaryl-4-aminobutyl)-2,5-diketopiperazine; FDKP) is one preferred diketopiperazine for pulmonary applications:

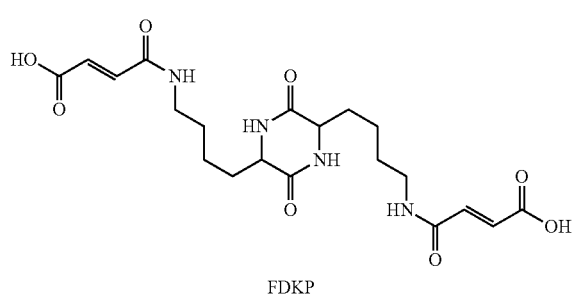 [SMILES: O=C(O)/C=C/C(=O)NCCCCC1NC(=O)C(CCCCNC(=O)/C=C/C(=O)O)NC1=O ; "FDKP"]

FDKP

FDKP provides a beneficial microparticle matrix because it has low solubility in acid but is readily soluble at neutral or basic pH. These properties allow FDKP to crystallize under acidic conditions and the crystals self-assemble to form particles. The particles dissolve readily under physiological conditions where the pH is neutral. In one embodiment, the microparticles disclosed herein are FDKP microparticles loaded with an active agent such as insulin.

FDKP is a chiral molecule having trans and cis isomers with respect to the arrangement of the substituents on the substituted carbons on the diketopiperazine ring. As described in US Patent Application Publication No. 2010/0317574, entitled "Diketopiperazine microparticles with defined isomer contents," more robust aerodynamic performance and consistency of particle morphology can be obtained by confining the isomer content to about 45-65% trans. Isomer ratio can be controlled in the synthesis and recrystallization of the molecule. Exposure to base promotes ring epimerization leading to racemization, for example during the removal of protecting groups from the terminal carboxylate groups. However increasing methanol content of the solvent in this step leads to increased trans isomer content. The trans isomer is less soluble than the cis isomers and control of temperature and solvent composition during recrystallization can be used to promote or reduce enrichment for the trans isomer in this step.

Microparticles having a diameter of between about 0.5 and about 10 microns can reach the lungs, successfully passing most of the natural barriers. A diameter of less than about 10 microns is required to navigate the turn of the throat and a diameter of about 0.5 microns or greater is required to avoid being exhaled. Diketopiperazine microparticles with a specific surface area (SSA) of between about 35 and about 67 $m^2/g$ exhibit characteristics beneficial to delivery of drugs to the lungs such as improved aerodynamic performance and improved drug adsorption.

As described in PCT Publication No. WO2010144789, entitled "Diketopiperazine microparticles with defined specific surface areas," the size distribution and shape of FDKP crystals are affected by the balance between the nucleation of new crystals and the growth of existing crystals. Both phenomena depend strongly on concentrations and supersaturation in solution. The characteristic size of the FDKP crystal is an indication of the relative rates of nucleation and growth. When nucleation dominates, many crystals are formed but they are relatively small because they all compete for the FDKP in solution. When growth dominates, there are fewer competing crystals and the characteristic size of the crystals is larger.

Crystallization depends strongly on supersaturation which, in turn, depends strongly on the concentration of the components in the feed streams. Higher supersaturation is associated with the formation of many small crystals; lower supersaturation produces fewer, larger crystals. In terms of supersaturation: 1) increasing the FDKP concentration raises the supersaturation; 2) increasing the concentration of ammonia shifts the system to higher pH, raises the equilibrium solubility and decreases the supersaturation; and 3) increasing the acetic acid concentration increases the supersaturation by shifting the endpoint to lower pH where the equilibrium solubility is lower. Decreasing the concentrations of these components induces the opposite effects.

Temperature affects FDKP microparticle formation through its effect on FDKP solubility and the kinetics of FDKP crystal nucleation and growth. At low temperatures, small crystals are formed with high specific surface area. Suspensions of these particles exhibit high viscosity indicating strong inter-particle attractions. A temperature range of about 12° C. to about 26° C. produced particles with acceptable (or better) aerodynamic performance with various inhaler systems including inhaler systems disclosed herein.

These present devices and systems are useful in the pulmonary delivery for powders with a wide range of characteristics. Embodiments of the invention include systems comprising an inhaler, an integral or installable unit dose cartridge, and powder of defined characteristic(s) providing an improved or optimal range of performance. For example, the devices constitute an efficient deagglomeration engine and thus can effectively deliver cohesive powders. This is distinct from the course pursued by many others who have sought to develop dry powder inhalation systems based on free flowing or flow optimized particles (see for example U.S. Pat. Nos. 5,997,848 and 7,399,528, US Patent Application No. 2006/0260777; and Ferrari et al. AAPS *Pharm Sci Tech* 2004; 5 (4) Article 60). Thus, embodiments include systems plus a cohesive powder.

Cohesiveness of a powder can be assessed according to its flowability or correlated with assessments of shape and irregularity such as rugosity. As discussed in the US Pharmacopeia USP 29, 2006 section 1174 four techniques commonly used in the pharmaceutical arts to assess powder flowability: angle of repose; compressibility (Carr's) index and Hausner ratio; flow through an orifice; and shear cell methods. For the latter two no general scales have been developed due to diversity of methodology. Flow through an orifice can be used to measure flow rate or alternatively to determine a critical diameter that allows flow. Pertinent variables are the shape and diameter of the orifice, the diameter and height of the powder bed, and the material the apparatus is made of. Shear cell devices include cylindrical, annular, and planar varieties and offer great degree of experimental control. For either of these two methods description of the equipment and methodology are crucial, but despite the lack of general scales they are successfully used to provide qualitative and relative characterizations of powder flowability.

Angle of repose is determined as the angle assumed by a cone-like pile of the material relative to a horizontal base upon which it has been poured. Hausner ratio is the unsettled volume divided by the tapped volume (that is the volume after tapping produces no further change in volume), or alternatively the tapped density divided by the bulk density. The compressibility index (CI) can be calculated from the Hausner ratio (HR) as $$CI=100\times(1-(1/HR)).$$

Despite some variation in experimental methods generally accepted scales of flow properties have been published for angle of repose, compressibility index and Hausner ratio (Carr, R L, *Chem. Eng.* 1965, 72:163-168).

| Flow Character | Angle of Repose | Hausner Ratio | Compressibility Index (%) |
|---|---|---|---|
| Excellent | 25-30° | 1.00-1.11 | ≤10 |
| Good | 31-35° | 1.12-1.18 | 11-15 |
| Fair | 36-40° | 1.19-1.25 | 16-20 |
| Passable | 41-45° | 1.26-1.34 | 21-25 |
| Poor | 46-55° | 1.35-1.45 | 26-31 |
| Very Poor | 56-65° | 1.46-1.59 | 32-27 |
| Very, Very Poor | ≥66° | ≥1.60 | ≥38 |

The Conveyor Equipment Manufacturers Association (CEMA) code provides a somewhat different characterization of angle of repose.

| Angle of repose | Flowability |
| --- | --- |
| ≤19° | Very free flowing |
| 20-29° | Free flowing |
| 30-39° | Average |
| ≥40° | Sluggish |

Powders with a flow character according to the table above that is excellent or good can be characterized in terms of cohesiveness as non- or minimally cohesive, and the powders with less flowability as cohesive and further dividing them between moderately cohesive (corresponding to fair or passable flow character) and highly cohesive (corresponding to any degree of poor flow character). In assessing angle of repose by the CEMA scale powders with an angle of repose ≥30° can be considered cohesive and those ≥40° highly cohesive. Powders in each of these ranges, or combinations thereof, constitute aspects of distinct embodiments of the invention.

Cohesiveness can also be correlated with rugosity, a measure of the irregularity of the particle surface. The rugosity is the ratio of the actual specific surface area of the particle to that for an equivalent sphere:

$$\text{Rugosity} = \frac{(SSA)_{particle}}{(SSA)_{sphere}}$$

Methods for direct measurement of rugosity, such as air permeametry, are also known in the art. Rugosity of 2 or greater has been associated with increased cohesiveness. It should be kept in mind that particle size also affects flowability so that larger particles (for example on the order of 100 microns) can have reasonable flowability despite somewhat elevated rugosity. However for particles useful for delivery into the deep lung, such as those with primary particle diameters of 1-3 microns, even modestly elevated rugosity or 2-6 may be cohesive. Highly cohesive powders can have rugosities ≥10 (see Example A below).

Many of the examples below involve the use of dry powders comprising FDKP. The component microparticles are self-assembled aggregates of crystalline plates. Powders comprised of particles with plate-like surfaces are known to have generally poor flowability, that is, they are cohesive. Indeed smooth spherical particles generally have the best flowability, with flowability generally decreasing as the particles become oblong, have sharp edges, become substantially two dimensional and irregularly shaped, have irregular interlocking shapes, or are fibrous. While not wanting to be bound, it is the Applicants' present understanding that the crystalline plates of the FDKP microparticles can interleave and interlock contributing to the cohesiveness (the inverse of flowability) of bulk powders comprising them and additionally making the powder more difficult to deagglomerate than less cohesive powders. Moreover factors affecting the structure of the particles can have effects on aerodynamic performance. It has been observed that as specific surface area of the particles increases past a threshold value their aerodynamic performance, measured as respirable fraction, tends to decrease. Additionally FDKP has two chiral carbon atoms in the piperazine ring, so that the N-fumaryl-4-aminobutyl arms can be in cis or trans configurations with respect to the plane of the ring. It has been observed that as the trans-cis ratio of the FDKP used in making the microparticles departs from an optimal range including the racemic mixture respirable fraction is decreased and at greater departures from the preferred range the morphology of the particles in SEM becomes visibly different. Thus embodiments of the invention include systems of the device plus diketopiperazine powders with specific surface areas within preferred ranges, and the device plus FDKP powders with trans-cis isomer ratios within preferred ranges.

FDKP microparticles either unmodified or containing a drug, for example insulin, constitute highly cohesive powders. FDKP microparticles have been measured to have a Hausner ratio of 1.8, a compressibility index of 47%, and an angle of repose of 40°. Insulin loaded FDKP microparticles (TECHNOSPHERE® Insulin; TI; MannKind Corporation, Valencia, Calif.) have been measured to have a Hausner ratio of 1.57, a compressibility index of 36%, and an angle of repose of 50°±3°. Additionally in critical orifice testing it was estimated that to establish flow under gravity an orifice diameter on the order of 2 to 3 feet (60-90 cm) would be needed (assumes a bed height of 2.5 feet; increased pressure increased the size of the diameter needed). Under similar conditions a free flowing powder would require an orifice diameter on the order of only 1-2 cm (Taylor, M. K. et al. *AAPS Pharm Sci Tech* 1, art. 18).

Accordingly, in one embodiment, the present inhalation system comprises a dry powder inhaler and a container for deagglomerating cohesive powder is provided, comprising a cohesive dry powder having a Carr's index ranging from 16 to 50. In one embodiment, the dry powder formulation comprises a diketopiperazine, including, FDKP and a peptide or protein including an endocrine hormone such as insulin, GLP-1, parathyroid hormone, oxyntomodulin, and others as mentioned elsewhere in this disclosure.

Microparticles having a diameter of between about 0.5 and about 10 microns can reach the lungs, successfully passing most of the natural barriers. A diameter of less than about 10 microns is required to navigate the turn of the throat and a diameter of about 0.5 microns or greater is required to avoid being exhaled. Embodiments disclosed herein show that microparticles with a SSA of between about 35 and about 67 $m^2/g$ exhibit characteristics beneficial to delivery of drugs to the lungs such as improved aerodynamic performance and improved drug adsorption.

Disclosed herein are also FDKP microparticles having a specific trans isomer ratio of about 45 to about 65%. In this embodiment, the microparticles provide improved flyability.

In one embodiment, there is also provided a system for the delivery of an inhalable dry powder comprising: a) a cohesive powder comprising a medicament, and b) an inhaler comprising an enclosure defining an internal volume for containing a powder, the enclosure comprising a gas inlet and a gas outlet wherein the inlet and the outlet are positioned so that gas flowing into the internal volume through the inlet is directed at the gas flowing toward the outlet. In an embodiment, the system is useful for deagglomerating a cohesive powder having a Carr's index of from 18 to 50. The system can also be useful for delivering a powder when the cohesive powder has an angle of repose from 30° to 55°. The cohesive powder can be characterized by a critical orifice dimension of ≤3.2 feet for funnel flow or ≤2.4 feet for mass flow, a rugosity >2. Exemplary cohesive powder particles include particles comprising of FDKP crystals wherein the ratio of FDKP isomers in the range of 50% to 65% trans:cis.

In another embodiment, the inhalation system can comprise an inhaler comprising a mouthpiece and upon applying a pressure drop of ≥2 kPa across the inhaler to generate a plume of particles which is emitted from the mouthpiece wherein 50% of the emitted particles have a VMGD of ≤10 micron, wherein 50% of the emitted particles have a VMGD of ≤8 microns, or wherein 50% of the emitted particles have a VMGD of ≤4 microns.

In yet another embodiment, a system for the delivery of an inhalable dry powder comprising: a) a dry powder comprising particles composed of FDKP crystals wherein the ratio of FDKP isomers in the range of 50% to 65% trans:cis, and a medicament; and b) an inhaler comprising a powder containing enclosure, the chamber comprising a gas inlet and a gas outlet; and a housing in which to mount the chamber and defining two flow pathways, a first flow pathway allowing gas to enter the gas inlet of the chamber, a second flow pathway allowing gas to bypass the chamber gas inlet; wherein flow bypassing the enclosure gas inlet is directed to impinge upon the flow exiting the enclosure substantially perpendicular to the gas outlet flow direction.

In certain embodiments, a system for the delivery of an inhalable dry powder is provided, comprising: a) a dry powder comprising particles composed of FDKP crystals wherein the microparticles have a SSA of between about 35 and about 67 $m^2/g$ which exhibit characteristics beneficial to delivery of drugs to the lungs such as improved aerodynamic performance and improved drug adsorption per milligram, and a medicament; and b) an inhaler comprising a powder containing enclosure, wherein the enclosure comprises a gas inlet and a gas outlet; and a housing in which to mount the chamber and defining two flow pathways, a first flow pathway allowing gas to enter the gas inlet of the chamber, a second flow pathway allowing gas to bypass the chamber gas inlet; wherein flow bypassing the chamber gas inlet is directed to impinge upon the flow exiting the enclosure substantially perpendicular to the gas outlet flow direction.

A system for the delivery of an inhalable dry powder is also provided, comprising: a) a dry powder comprising a medicament, and b) an inhaler comprising a powder containing cartridge, the cartridge comprising a gas inlet and a gas outlet, and a housing in which to mount the cartridge and defining two flow pathways, a first flow pathway allowing gas to enter the gas inlet of the cartridge, a second flow pathway allowing gas to bypass the enclosure gas inlet, and a mouthpiece and upon applying a pressure drop of ≥2 kPa across the inhaler plume of particles is emitted from the mouthpiece wherein 50% of the emitted particles have a VMGD of ≤10 microns, wherein flow bypassing the cartridge gas inlet is directed to impinge upon the flow exiting the enclosure substantially perpendicular to the gas outlet flow direction.

Active agents for use in the compositions and methods described herein can include any pharmaceutical agent. These can include, for example, synthetic organic compounds, including, vasodialators, vasoconstrictor molecules, neurotransmitter analogs, neurotransmitter antagonists, steroids, anti-nociceptive agents, peptides and polypeptides, polysaccharides and other sugars, lipids, inorganic compound, and nucleic acid molecules, having therapeutic, prophylactic, or diagnostic activities. Peptides, proteins, and polypeptides are all chains of amino acids linked by peptide bonds.

Examples of active agents that can be delivered to a target or site in the body using the diketopiperazine formulations, include hormones, anticoagulants, immunomodulating agents, vaccines, cytotoxic agents, antibiotics, vasoactive agents, neuroactive agents, anaesthetics or sedatives, steroid molecules such as glucocorticoids including fluticasone, budesonide, mometasone, ciclesonide, flunisolide, betamethasone, and triamcinolone, decongestants, antivirals, antisense, antigens, and antibodies. More particularly, these compounds include insulin, heparin (including low molecular weight heparin), calcitonin, felbamate, sumatriptan, parathyroid hormone and active fragments thereof, growth hormone, erythropoietin, AZT, DDI, granulocyte macrophage colony stimulating factor (GM-CSF), lamotrigine, chorionic gonadotropin releasing factor, luteinizing releasing hormone, beta-galactosidase, exendin, vasoactive intestinal peptide, argatroban, small molecules, including anticancer and inhibitors or analogs of cell receptors such as neurorecptors, including, anti-nociceptive agents; triptans including, Sumatriptan succinate, Almotriptan malate, Rizatriptan benzoate, Zolmitriptan, Eletriptan hydrobromide, Naratriptan hydrochloride, $\mu_2$-agonists such as salbutamol fenoterol formoterol terbutaline pirbuterol, bitolterol, indacaterol, and the like, and vaccines. Antibodies and fragments thereof can include, in a non-limiting manner, anti-SSX-$2_{41-49}$ (synovial sarcoma, X breakpoint 2), anti-NY-ESO-1 (esophageal tumor associated antigen), anti-PRAME (preferentially expressed antigen of melanoma), anti-PSMA (prostate-specific membrane antigen), anti-Melan-A (melanoma tumor associated antigen) and anti-tyrosinase (melanoma tumor associated antigen).

In certain embodiments, a dry powder formulation for delivering a pharmaceutical formulation to the pulmonary circulation comprises an active ingredient or agent, including, a peptide, a protein, a hormone, analogs thereof or combinations thereof, wherein the active ingredient is insulin, calcitonin, growth hormone, erythropoietin, granulocyte macrophage colony stimulating factor (GM-CSF), chorionic gonadotropin releasing factor, luteinizing releasing hormone, follicle stimulating hormone (FSH), vasoactive intestinal peptide, parathyroid hormone (including black bear PTH), parathyroid hormone related protein, glucagon-like peptide-1 (GLP-1), exendin, oxyntomodulin, peptide YY, interleukin 2-inducible tyrosine kinase, Bruton's tyrosine kinase (BTK), inositol-requiring kinase 1 (IRE1), or analogs, active fragments, PC-DAC-modified derivatives, or O-glycosylated forms thereof. In particular embodiments, the pharmaceutical composition or dry powder formulation comprises fumaryl diketopiperazine and the active ingredient is one or more selected from insulin, parathyroid hormone 1-34, GLP-1, oxyntomodulin, peptide YY, heparin and analogs thereof; small molecules, including neurotransmitters, derivatives and/or analogs or inhibitors/antagonists, anti-nociceptive agents such as pain modulators, headache medications, antimigraine drugs, including vasoactive agents such as triptans, and vaccine and adjuvants thereof; immunosuppressant molecules and anticancer drugs.

In one embodiment, a method of self-administering a dry powder formulation to one's lung with a dry powder inhalation system is also provided, comprising: obtaining a dry powder inhaler in a closed position and having a mouthpiece; obtaining a cartridge comprising a pre-metered dose of a dry powder formulation in a containment configuration; opening the dry powder inhaler to install the cartridge; closing the inhaler to effectuate movement of the cartridge to a dose position; placing the mouthpiece in one's mouth, and inhaling once deeply to deliver the dry powder formulation.

In one embodiment, a method of delivering an active ingredient comprising: a) providing dry powder inhaler containing a cartridge with a dry powder formulation comprising a diketopiperazine and the active agent; and b) delivering the active ingredient or agent to an individual in need of treatment. The dry powder inhaler system can deliver a dry powder formulation such as insulin FDKP having a respirable fraction greater than 50% and particles sizes less than 5.8 μm.

In still yet a further embodiment, a method of treating obesity, hyperglycemia, insulin resistance, and/or diabetes is disclosed. The method comprises the administration of an inhalable dry powder composition or formulation comprising a diketopiperazine having the formula 2,5-diketo-3,6-di(4-X-aminobutyl)piperazine, wherein X is selected from the group consisting of succinyl, glutaryl, maleyl, and fumaryl. In this embodiment, the dry powder composition can comprise a diketopiperazine salt. In still yet another embodiment of the present invention, there is provided a dry powder composition or formulation, wherein the diketopiperazine is 2,5-diketo-3,6-di-(4-fumaryl-aminobutyl)piperazine, with or without a pharmaceutically acceptable carrier, or excipient.

In one embodiment, the inhalation system for delivering a dry powder formulation to a patient's lungs comprises a dry powder inhaler configured to have flow conduits with a total resistance to flow in a dosing configuration ranging in value from 0.065 to about 0.200 (√kPa)/liter per minute.

In one embodiment, a dry powder inhalation kit is provided comprising a dry powder inhaler as described above, and one or more medicament cartridge comprising a dry powder formulation for treating a disorder or disease such as respiratory tract disease, diabetes and obesity. In this embodiment, the kit can comprise materials with instructions for use.

The improved cartridge emptying and deagglomeration capabilities of the inhalation systems described herein contribute to increased bioavailability of dry powder formulation. In particular embodiments, the dry powders are diketopiperazine containing powders. By bioavailability we refer to the exposure to either the active ingredient (e.g. insulin) or the diketopiperazine (in those embodiments related to diketopiperazine powders) resultant from delivery into a subject's systemic circulation, as commonly assessed by the AUC of a concentration versus time plot. By normalizing such measurements to dosage a characteristic of the system can be revealed. The dosage used in normalizing exposure can be based on filled or emitted dose and can be expressed in unit mass of powder. Alternatively exposure can be normalized to a cartridge of a particular fill mass. Either way exposure can be further adjusted to take into account the specific diketopiperazine or active ingredient content of a particular formulation, that is, the exposure can be normalized to the amount of active agent or the amount of diketopiperazine in the filled or emitted dose. Variables related to the subject, for example fluid volume, can affect the observed exposure so in various embodiments bioavailability of the system will be expressed as a range or limit.

In one embodiment, the powder formulation can comprise microparticles of FDKP and insulin as the active agent for the treatment of diabetes, wherein the insulin content of the formulation can be 3 U/mg, 4 U/mg, 6 U/mg of powder or greater. The amount of insulin or dose to be administered can vary depending on the patient's need. For example, in one embodiment, a single dose for a single inhalation can contain up to about 60 U of insulin for the treatment of hyperglycemia in diabetes.

The pharmacokinetic profile of insulin is an important factor in determining its physiologic effect. With similar insulin exposures an insulin administration of a formulation which provides a pharmacokinetic profile characterized by a rapidly attained peak is more effective at suppressing prandial glucose excursions and hepatic glucose release than is an insulin administration resulting in a slower rise to $C_{max}$ and characterized by an extended plateau. Thus, the inhalation systems disclosed herein also result in the more efficient delivery of insulin so that similar $C_{max}$ levels can be attained with smaller doses of insulin as compared to prior art systems. Stated otherwise these inhalations systems attain a higher dose normalized $C_{max}$.

Example 1

Measuring the Resistance and Flow Distribution of a Dry Powder Inhaler—Cartridge System Several dry powder inhaler designs were tested to measure their resistance to flow—an important characteristic determined in part by the geometries or configurations of the inhaler pathways. Inhalers exhibiting high resistance require a greater pressure drop to yield the same flow rate as lower resistance inhalers. Briefly, to measure the resistance of each inhaler and cartridge system, various flow rates are applied to the inhaler and the resulting pressures across the inhaler are measured. These measurements can be achieved by utilizing a vacuum pump attached to the mouthpiece of the inhaler, to supply the pressure drop, and a flow controller and pressure meter to change the flow and record the resulting pressure. According to the Bernoulli principle, when the square root of the pressure drop is plotted versus the flow rate, the resistance of the inhaler is the slope of the linear portion of the curve. In these experiments, the resistance of the inhalation system, comprising a dry powder inhaler and cartridge as described herein, were measured in the dosing configuration using a resistance measuring device. The dosing configuration forms an air pathway through the inhaler air conduits and through the cartridge in the inhaler.

Since different inhaler designs exhibit different resistance values due to slight variations in geometries of their air pathways, multiple experiments were conducted to determine the ideal interval for pressure settings to use with a particular design. Based on the Bernoulli principle of linearity between square root of pressure and flow rate, the intervals for assessing linearity were predetermined for the three inhalers used after multiple tests so that the appropriate settings could be used with other batches of the same inhaler design. An exemplary graph for an inhaler can be seen in FIG. 33 for an inhalation system depicted in FIG. 7. The graph depicted in FIG. 33 indicates that the resistance of the inhalation system as depicted in FIG. 7 can be measured with good correlation to the Bernoulli principle at flow rates ranging from about 10 to 25 L/min. The graph also shows that the resistance of the exemplary inhalation system was determined to be 0.093 √kPa/LPM. FIG. 33 illustrates that flow and pressure are related. Therefore, as the slope of the line in square root of pressure versus flow graph decreases, i.e., inhalation systems exhibiting lower resistance, the change in flow for a given change in pressure is greater. Accordingly, higher resistance inhalation systems would exhibit less variability in flow rates for given changes in pressure provided by the patient with a breath powered system.

The data in Tables 1 show the results of a set of experiments using the inhalation system described in FIG. 10 (DPI 1), and FIG. 7 (DPI 2). For the dry powder inhaler 1 (DPI 1), the cartridge illustrated in design 150, FIGS. 17-21, was used, and the cartridge illustrated in design 170, FIG. 22-30 was used with DPI 2. Accordingly, DPI 1 used Cartridge 1 and DPI 2 used Cartridge 2.

TABLE 1

| Device Tested | Total Device Resistance | Cartridge Resistance | % of Total Flow Through Cartridge |
|---|---|---|---|
| MEDTONE ® | 0.1099 | 0.368 | 15.28 |
| DPI 1 | 0.0874 | 0.296 | 29.50 |
| DPI 2 | 0.0894 | 0.234 | 35.56 |

Table 1 illustrates the resistance of the inhalation system tested herewith is 0.0874 and 0.0894 √kPa/LPM, respectively for DPI 1 and DPI 2. The data show that the resistance of the inhalation system to flow is in part determined by the geometry or configuration of the air conduits within the cartridge.

Example 2

Measurement of Particle Size Distribution Using an Inhaler System with an Insulin Formulation Measurements of the particle size distribution with a laser diffraction apparatus (Helos Laser Diffraction system, Sympatec Inc.) with an adaptor (MannKind Corp., U.S. patent application Ser. No. 12/727,179, which disclosure is incorporated herein by reference for its teaching of the relevant subject matter) were made of a formulation of various amounts in milligram (mg) of an insulin and fumaryl diketopiperazine particles provided in a cartridge-inhaler system as described herewith (inhaler of FIGS. 1-9 with cartridge 170 shown in FIGS. 22-30). The device is attached at one end to tubing, which is adapted to a flow meter (TSI, Inc. Model 4043) and a valve to regulate pressure or flow from a compressed air source. Once the laser system is activated and the laser beam is ready to measure a plume, a pneumatic valve is actuated to allow the powder to be discharged from the inhaler. The laser system measures the plume exiting the inhaler device automatically based on predetermined measurement conditions. The laser diffraction system is operated by software integrated with the apparatus and controlled by computer program. Measurements were made of samples containing different amounts of powder and different powder lots. The measurement conditions are as follows:

Laser measurement start trigger conditions: when ≥0.6% laser intensity is detected on a particular detector channel;

Laser measurement end trigger conditions: when ≤0.4% laser intensity is detected on a particular detector channel;

Distance between vacuum source and inhaler chamber is approximately 9.525 cm.

Multiple tests were carried out using different amounts of powders or fill mass in the cartridges. Cartridges were only used once. Cartridge weights were determined before and after powder discharge from the inhaler to determine discharged powder weights. Measurements in the apparatus were determined at various pressure drops and repeated multiple times as indicated in Table 2 below. Once the powder plume is measured, the data is analyzed and graphed. Table 2 depicts data obtained from the experiments, wherein CE denotes cartridge emptying (powder discharged) and Q3 (50%) is the geometric diameter of the 50th percentile of the cumulative powder particle size distribution of the sample, and q3(5.8 μm) denotes the percentage of the particle size distribution smaller than 5.8 μm geometric diameter.

TABLE 2

| Test No. | Pressure Drop (kPa) | Discharge Time (s) | Fill Mass (mg) | Sample Size | % CE | Q3 (50%) | q3 (5.8 μm) |
|---|---|---|---|---|---|---|---|
| 1 | 4 | 3 | 6.7 | 30 | 98.0 | 4.020 | 63.8 |
| 2 | 4 | 3 | 6.7 | 20 | 97.0 | 3.700 | 67.4 |
| 3 | 4 | 3 | 6.7 | 20 | 98.4 | 3.935 | 64.6 |
| 4 | 4 | 3 | 3.5 | 20 | 97.8 | 4.400 | 61.0 |
| 5 | 2 | 4 | 6.7 | 7 | 92.9 | 4.364 | 61.0 |
| 6 | 2 | 4 | 6.7 | 7 | 95.1 | 4.680 | 57.9 |
| 7 | 4 | 4 | 6.7 | 7 | 97.0 | 3.973 | 64.4 |
| 8 | 4 | 4 | 6.7 | 7 | 95.5 | 4.250 | 61.7 |
| 9 | 6 | 4 | 6.7 | 7 | 97.3 | 3.830 | 65.3 |
| 10 | 6 | 4 | 6.7 | 7 | 97.8 | 4.156 | 62.2 |

The data in Table 2 showed that 92.9% to 98.4% of the total powder fill mass was emitted from the inhalation system. Additionally, the data indicate that regardless of the fill mass, 50% of the particles emitted from the inhalation system had a geometric diameter of less than 4.7 μm as measured at the various times and pressure drops tested. Moreover, between 60% and 70% of the particles emitted had a geometric diameter of less than 5.8 μm.

Figure 34:
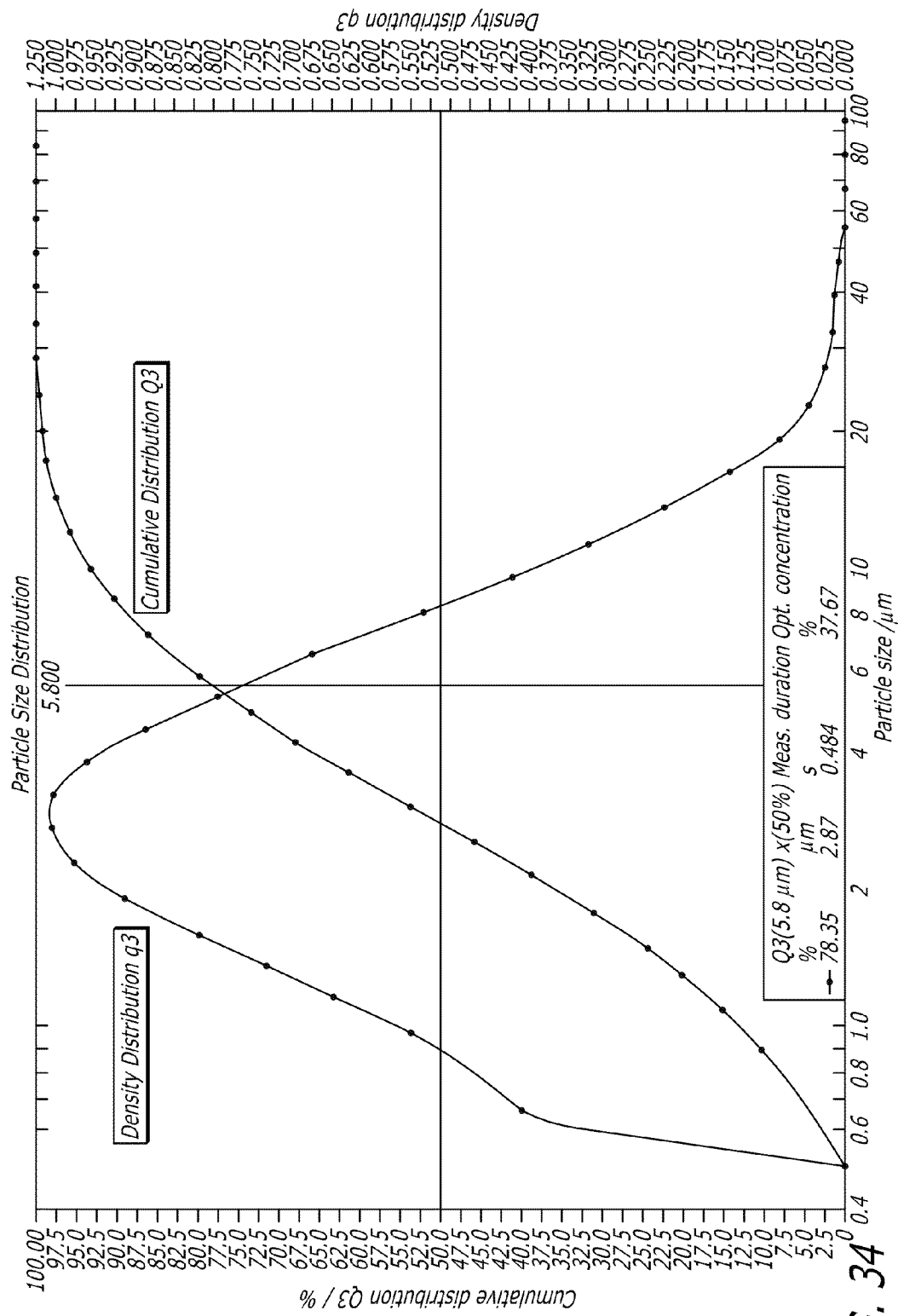
FIG. 34 depicts the particle size distribution obtained with a laser diffraction apparatus using an inhaler and cartridge containing a dry powder formulation for inhalation comprising insulin and fumaryl diketopiperizine particles.

FIG. 34 depicts data obtained from another experiment in which 10 mg of powder fill mass was used. The graph shows the particle size distribution of the sample containing particles of a formulation comprising insulin and fumaryl diketopiperazine resulted in 78.35% of the measured particles had a particle size of ≤5.8 μm. The laser detected 37.67% optical concentration during the measurement duration of 0.484 seconds at the above measurement conditions. The data show that the inhalation system effectively deagglomerates the insulin-FDKP formulation to small sizes over a relevant and lower range of user inhalation capacities, i.e., pressure drops. These small geometric sizes for this cohesive (Carr's index=36%) formulation are believed to be respirable.

Example 3

Measurement of Powder Discharge from a Cartridge as a Measure of Inhalation System Performance The experiments were conducted using the inhalation system described herewith using multiple inhaler prototypes depicted in FIGS. 1-9 with cartridge 170 prototypes as shown in FIGS. 22-30. Multiple cartridges were used with each inhaler. Each cartridge was weighed in an electronic balance prior to fill. The cartridges were filled with a predetermined mass of powder, again weighed and each filled cartridge was placed in an inhaler and tested for efficiency of emptying a powder formulation, i.e., TECHNOSPHERE® Insulin (insulin-FDKP; typically 3 U to 4 U insulin/mg powder, approximately 10-15% insulin w/w) powder batches. Multiple pressure drops were used to characterize the consistency of performance. Table 3 depicts results of this testing using 35 cartridge discharge measurements per inhaler. In the data in Table 3, all tests were carried out using the same batch of a clinical grade insulin-FDKP powder. The results show that relevant user pressure drops, ranging from 2 through 5 kPa demonstrated a highly efficient emptying of the powder from the cartridge.

TABLE 3

| Test No. | Pressure Drop (kPa) | Discharge Time (s) | Fill Mass (mg) | Sample Size | Mean % CE | % CE SD |
|---|---|---|---|---|---|---|
| 1 | 5.00 | 3.00 | 3.08 | 35 | 99.42 | 0.75 |
| 2 | 5.00 | 3.00 | 3.00 | 35 | 98.11 | 1.11 |
| 3 | 5.00 | 3.00 | 6.49 | 35 | 99.49 | 0.81 |
| 4 | 5.00 | 3.00 | 6.55 | 35 | 99.05 | 0.55 |
| 5 | 5.00 | 2.00 | 6.57 | 35 | 98.69 | 0.94 |

TABLE 3-continued

| Test No. | Pressure Drop (kPa) | Discharge Time (s) | Fill Mass (mg) | Sample Size | Mean % CE | % CE SD |
|---|---|---|---|---|---|---|
| 6 | 5.00 | 2.00 | 6.57 | 35 | 99.33 | 1.03 |
| 7 | 4.00 | 3.00 | 6.47 | 35 | 98.15 | 1.15 |
| 8 | 4.00 | 3.00 | 6.50 | 35 | 99.37 | 0.46 |
| 9 | 4.00 | 3.00 | 3.28 | 35 | 98.63 | 0.93 |
| 10 | 4.00 | 3.00 | 3.18 | 35 | 98.63 | 1.48 |
| 11 | 4.00 | 2.00 | 6.61 | 35 | 92.30 | 3.75 |
| 12 | 4.00 | 2.00 | 6.58 | 35 | 98.42 | 1.71 |
| 13 | 3.00 | 3.00 | 6.55 | 35 | 92.91 | 5.04 |
| 14 | 3.00 | 3.00 | 6.56 | 35 | 98.88 | 0.63 |
| 15 | 3.00 | 2.00 | 6.56 | 35 | 96.47 | 3.19 |
| 16 | 3.00 | 2.00 | 6.59 | 35 | 99.49 | 0.54 |
| 17 | 3.00 | 1.00 | 6.93 | 35 | 98.06 | 2.37 |
| 18 | 3.00 | 1.00 | 6.95 | 35 | 98.74 | 0.67 |
| 19 | 3.00 | 1.00 | 3.12 | 35 | 97.00 | 1.06 |
| 20 | 3.00 | 1.00 | 3.15 | 35 | 96.98 | 0.99 |
| 21 | 2.00 | 1.00 | 6.53 | 35 | 97.24 | 1.65 |
| 22 | 2.00 | 1.00 | 6.49 | 35 | 98.48 | 2.27 |

Example 4

Measurement of Predictive Deposition by Andersen Cascade Impaction

The experiments were conducted using an Andersen Cascade Impactor to collect stage plate powder deposits during a simulated dose delivery using flow rates of 28.3 LPM. This flow rate resulted in a pressure drop across the inhalation system (DPI plus cartridge) of approximately 6 kPa. Depositions on the plate stages were analyzed gravimetrically using filters and electronic balances. Fill weights of a cohesive powder in 10 mg, 6.6 mg and 3.1 mg fill mass were evaluated for inhalation system performance. Each impaction test was conducted with five cartridges. The cumulative powder mass collected on stages 2-F was measured in accordance with aerodynamic particle sizes less than 5.8 μm. The ratio of the collected powder mass to the cartridge fill content was determined and is provided as percent respirable fraction (RF) over the fill weight. The data is presented in Table 4.

The data show that a respirable fraction ranging from 50% to 70% was achieved with multiple powder batches. This range represents a normalized performance characteristic of the inhalation system.

The inhaler system performance measurements were repeated 35 times with a different cartridge. Fill mass (mg) and discharge time (seconds) were measured for each inhaler cartridge system used. Additionally, the percent of respirable fraction, i.e., particles suitable for pulmonary delivery, in the powder was also measured. The results are presented in Table 4 below. In the table, the % RF/fill equals the percent of particles having a size (≤5.8 μm) that would travel to the lungs in the powder; CE indicates cartridge emptying or powder delivered; RF indicates respirable fraction. In Table 4, Test Nos. 1-10 were conducted using a second batch of a clinical grade of the insulin-FDKP powder, but the test powder for 11-17 used the same powder as the tests conducted and presented in Table 3.

TABLE 4

| No. | Pressure Drop (kPa) | Discharge Time (s) | Fill Mass (mg) | Sample Size | Mean % CE | % RF/ Fill | % RF/ Delivered |
|---|---|---|---|---|---|---|---|
| 1 | 6.4 | 8 | 9.7 | 5 | 98.9 | 56.6 | 58.3 |
| 2 | 6.4 | 8 | 9.9 | 5 | 88.8 | 53.7 | 60.4 |
| 3 | 6.4 | 8 | 8.2 | 5 | 97.5 | 54.9 | 56.9 |
| 4 | 6.4 | 8 | 6.7 | 5 | 98.4 | 56.8 | 58.1 |
| 5 | 6.4 | 8 | 10.0 | 5 | 89.2 | 60.4 | 67.8 |
| 6 | 6.4 | 8 | 9.6 | 5 | 99.3 | 53.5 | 53.9 |
| 7 | 6.4 | 8 | 9.6 | 5 | 98.2 | 57.3 | 58.4 |
| 8 | 6.4 | 8 | 9.6 | 5 | 99.0 | 56.9 | 57.5 |
| 9 | 6.4 | 8 | 9.6 | 5 | 95.4 | 59.3 | 62.1 |
| 10 | 6.4 | 8 | 6.6 | 5 | 99.4 | 61.7 | 62.1 |
| 11 | 6.4 | 8 | 6.6 | 5 | 99.6 | 59.0 | 59.2 |
| 12 | 6.4 | 8 | 6.6 | 5 | 96.5 | 62.6 | 64.8 |
| 13 | 6.4 | 8 | 6.6 | 5 | 98.7 | 59.8 | 60.6 |
| 14 | 6.4 | 8 | 3.1 | 5 | 99.5 | 66.3 | 66.6 |
| 15 | 6.4 | 8 | 3.1 | 5 | 99.7 | 70.7 | 70.9 |
| 16 | 6.4 | 8 | 3.1 | 5 | 97.6 | 65.9 | 67.5 |
| 17 | 6.4 | 8 | 3.1 | 5 | 98.2 | 71.6 | 73.0 |

The data above show that the present inhalation system comprising a dry powder inhaler and a cartridge containing a cohesive powder, i.e., TECHNOSPHERE® Insulin (FDKP particles comprising insulin) can discharge effectively almost all of the powder content, since greater than 85% and in most cases greater than 95% of the total powder content of a cartridge at variable fill masses and pressure drops were obtained with consistency and significant degree of emptying. The Andersen cascade impaction measurements indicated that greater than 50% of the particles are in the respirable range wherein the particles are less than 5.8 μm and ranging from 53.5% to 73% of the total emitted powder.

Example 5

Rugosity of TECHNOSPHERE® Insulin (TI)

The rugosity is the ratio of the actual specific surface area of the particle to that for an equivalent sphere. The specific surface area of a sphere is:

$$SSA_{sphere} = \frac{\pi d_{eff}^2}{\rho \frac{\pi}{6} d_{eff}^3} = \frac{6}{\rho d_{eff}}$$

where $d_{eff}$=1.2 μm is the surface-weighted diameter of TI particles from Sympatec/RODOS laser diffraction measurements.

An average sphere with the same density as the TI particle matrix (1.4 g/cm$^3$) would therefore have an SSA of $$SSA_{sphere} = \frac{6}{\rho d_{eff}} = \frac{6}{\left(1.4\frac{g}{cm^3}\right)(1.2\times 10^{-6}\ m)}\left(\frac{m^3}{10^6\ cm^3}\right) = 3.6\ m^2/g$$

Thus for TI particles with specific surface area (SSA) of approximately 40 m$^2$/g $$\text{Rugosity} = \frac{(SSA)_{TI}}{(SSA)_{sphere}} = \frac{40\ m^2/g}{3.6\ m^2/g} \approx 11.$$

For similarly sized particles with specific surface area of 50 or 60 m²/g the rugosity would be roughly 14 and 16 respectively.

Example 6

Geometric Particle Size Analysis of Emitted Formulations by Volumetric Median Geometric Diameter (VMGD) Characterization Laser diffraction of dry powder formulations emitted from dry powder inhalers is a common methodology employed to characterize the level of de-agglomeration subjected to a powder. The methodology indicates a measure of geometric size rather than aerodynamic size as occurring in industry standard impaction methodologies. Typically, the geometric size of the emitted powder includes a volumetric distribution characterized by the median particle size, VMGD. Importantly, geometric sizes of the emitted particles are discerned with heightened resolution as compared to the aerodynamic sizes provided by impaction methods. Smaller sizes are preferred and result in greater likelihood of individual particles being delivered to the pulmonary tract. Thus, differences in inhaler de-agglomeration and ultimate performance can be easier to resolve with diffraction. In these experiments, an inhaler as specified in Example 3 and a predicate inhaler are tested with laser diffraction at pressures analogous to actual patient inspiratory capacities to determine the effectiveness of the inhalation system to de-agglomerate powder formulations. Specifically, the formulations included cohesive diketopiperazine powders with an active insulin loaded ingredient and without. These powder formulations possessed characteristic surface areas, isomer ratios, and Carr's indices. Reported in Table 5 are a VMGD and an efficiency of the container emptying during the testing. FDKP powders have an approximate Carr's index of 50 and TI powder has an approximate Carr's index of 40.

TABLE 5

| Inhaler system | powder | % trans | SSA | pressure drop (kPa) | sample size | % CE | VMGD (micron) |
|---|---|---|---|---|---|---|---|
| DPI 2 | FDKP | 56 | 55 | 4 | 15 | 92.5 | 6.800 |
| MEDTONE ® | FDKP | 56 | 55 | 4 | 30 | 89.5 | 21.200 |
| DPI 2 | FDKP + active | 56 | 45 | 4 | 30 | 98.0 | 4.020 |
| DPI 2 | FDKP + active | 56 | 45 | 4 | 20 | 97.0 | 3.700 |
| DPI 2 | FDKP + active | 56 | 45 | 4 | 20 | 98.4 | 3.935 |
| DPI 2 | FDKP + active | 56 | 45 | 4 | 20 | 97.8 | 4.400 |
| MEDTONE ® | FDKP + active | 56 | 45 | 4 | 10 | 86.1 | 9.280 |
| MEDTONE ® | FDKP + active | 56 | 45 | 4 | 10 | 92.3 | 10.676 |
| DPI 2 | FDKP + active | 56 | 45 | 2 | 7 | 92.9 | 4.364 |
| DPI 2 | FDKP + active | 56 | 45 | 2 | 7 | 95.1 | 4.680 |
| DPI 2 | FDKP + active | 56 | 45 | 4 | 7 | 97.0 | 3.973 |
| DPI 2 | FDKP + active | 56 | 45 | 4 | 7 | 95.5 | 4.250 |
| DPI 2 | FDKP + active | 56 | 56 | 4 | 10 | 99.6 | 6.254 |
| DPI 2 | FDKP + active | 56 | 14 | 4 | 10 | 85.5 | 4.037 |
| MEDTONE ® | FDKP + active | 56 | 56 | 4 | 20 | 89.7 | 12.045 |
| MEDTONE ® | FDKP + active | 56 | 14 | 4 | 20 | 37.9 | 10.776 |
| DPI 2 | FDKP + active | 54 | 50 | 4 | 10 | 97.1 | 4.417 |
| DPI 2 | FDKP + active | 54 | 44 | 4 | 10 | 96.0 | 4.189 |
| DPI 2 | FDKP + active | 56 | 35 | 4 | 10 | 92.0 | 3.235 |
| DPI 2 | FDKP + active | 50 | 34 | 4 | 10 | 93.2 | 5.611 |
| DPI 2 | FDKP + active | 66 | 33 | 4 | 10 | 79.0 | 4.678 |
| DPI 2 | FDKP + active | 45 | 42 | 4 | 10 | 93.2 | 5.610 |
| DPI 2 | FDKP + active | 56 | 9 | 4 | 10 | 78.9 | 5.860 |

These data in Table 5 show an improvement in powder de-agglomeration over a predicate inhaler system as compared to the inhaler system described herein. Diketopiperazine formulations with surface areas ranging from 14-56 m²/g demonstrated emptying efficiencies in excess of 85% and VMGD less than 7 microns. Similarly, formulations possessing an isomer ratio ranging from 45-66% trans demonstrated improved performance over the predicate device. Lastly, performance of the inhaler system with formulations characterized with Carr's indices of 40-50 were shown to be improved over the predicate device as well. In all cases, the reported VMGD values were below 7 microns.

Example 7

In Vitro Performance Improvement Realized in a Next Generation Dry Powder Delivery System TECHNOSPHERE® formulations have been successfully delivered to patients with MEDTONE® delivery system (MTDS, MannKind Corporation, Valencia, Calif.). This system includes dry powder formulations, pre-metered into single-use cartridges and inserted into a high resistance, breath-powered, re-usable MEDTONE® inhaler. An improved delivery system (DPI 2 as described in Example 1) has been developed as an alternative to MTDS. In vitro powder performance for these systems was compared for various parameter of inhaler performance. For DPI 2 a single discharge per cartridge was used as compared to two discharges per cartridge in the MEDTONE® system.

Particle sizing by laser diffraction and quantification of emitted mass as described above were used in these experiments. A laser diffraction instrument (Sympatec HELOS) was adapted with a novel pressurized inhaler chamber to facilitate analysis of powder plumes. MTDS cartridges were discharged twice per determination versus once with DPI 2. The inhalation systems were used with peak pressures of 4 kPa to assess powder-emptying percentage and volumetric median geometric diameter (VMGD) with TECHNOSPHERE® (FDKP inhalation powder) and TECHNOSPHERE® Insulin (FDKP-insulin inhalation powder) formulations.

Figure 35:
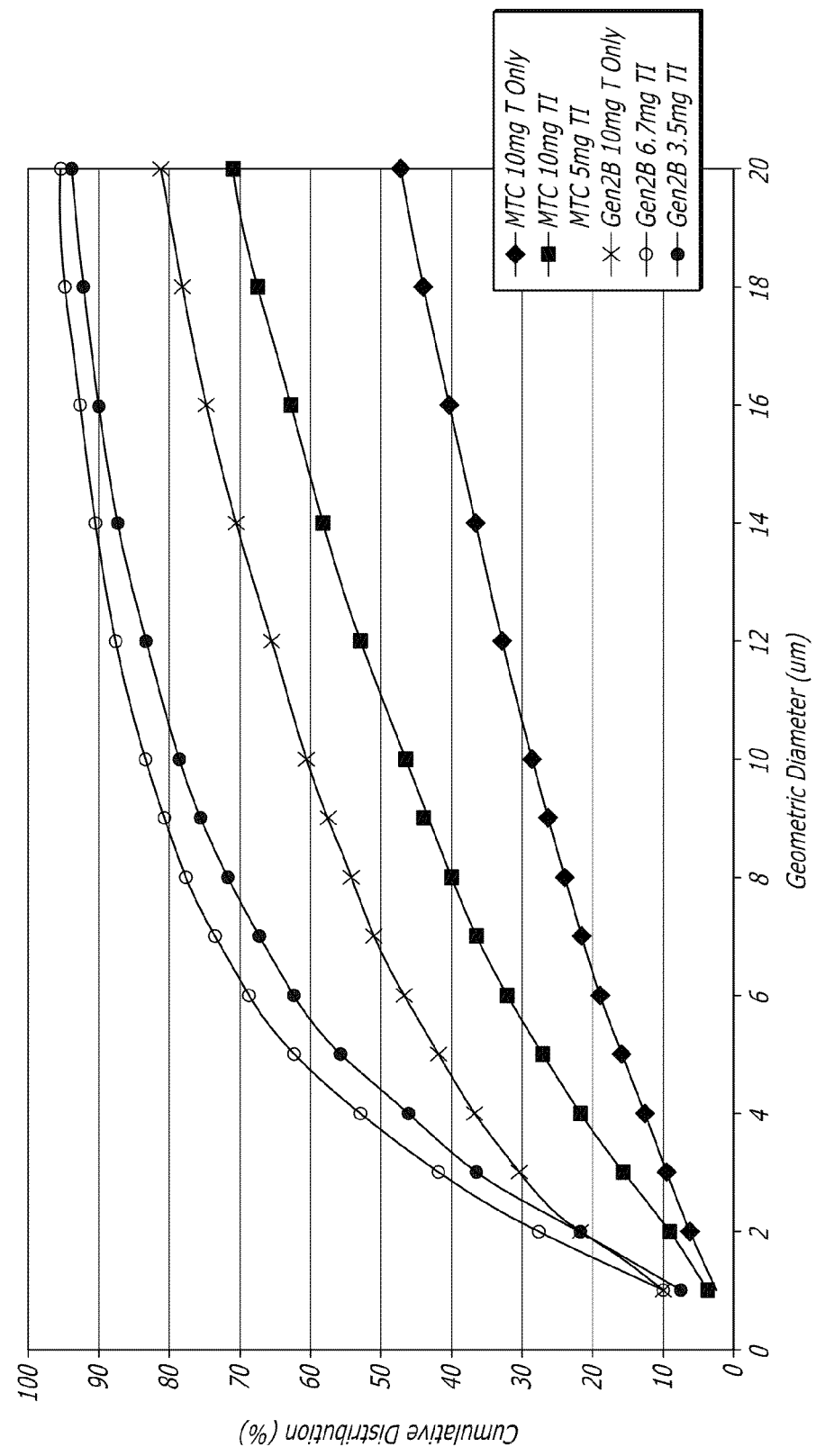
FIG. 35 depicts graphic representations of data obtained from the average of all tests performed for an example inhalation system (DPI 2) and MEDTONE® (MTC), showing the cumulative geometric particle size distribution of particles emitted from the inhalation systems from different cartridge powder contents.

The results of the experiments are shown in Table 6 and FIG. 35. In summary, for DPI 2, powder-emptying percentages were 97.8% (FDKP-insulin, fill weight 3.5 mg; n=20), 96.8% (FDKP-insulin, fill weight 6.7 mg; n=20), and 92.6% (FDKP inhalation powder, fill weight 10.0 mg; n=15); VMGDs (microns) were 4.37, 3.69, and 6.84, respectively. For MTDS, powder-emptying percentages were 89.9% (FDKP-insulin, fill weight 5.0 mg; n=30), 91.7% (FDKP-insulin, fill weight 10.0 mg; n=30), and 89.4% (FDKP inhalation powder, fill weight 10.0 mg; n=30); VMGDs (microns) were 10.56, 11.23, and 21.21, respectively.

FIG. 35 depicts graphic representations of data obtained from the average of all tests performed for each inhalation system. As seen in FIG. 35, the cumulative distribution of particle sizes is smaller for DPI 2 than with MEDTONE®. When compared to MEDTONE®, the DPI 2 inhalation system produces a larger percentage of smaller particles. This is evidence of an improved deagglomeration mechanism provided in the DPI 2 system. These data support clinical use of DPI 2 as a viable and improved alternative for delivering FDKP inhalation powder formulations. Percent emptying was improved with DPI 2, offering users the significant advantage of a single discharge per cartridge compared with two discharges with MTDS. Reductions in median geometric particle size suggest increased powder de-agglomeration within DPI 2. The clinical impact of this improved de-agglomeration must now be assessed.

TABLE 6

| Inhaler System | Number of Cartridges | Ave. VMGD (μm) | Ave. Geometric SD (μm) | Ave. % Cartridge Emptying |
|---|---|---|---|---|
| DPI 2 (3.5 mg FDKP-insulin) | 20 | 4.37 | 2.74 | 97.8 |
| DPI 2 (6.7 mg FDKP-insulin) | 20 | 3.69 | 2.73 | 96.8 |
| DPI 2 (10 mg FDKP) | 15 | 6.84 | 3.79 | 92.6 |
| MEDTONE ® (5 mg FDKP-insulin) | 30 | 10.56 | 2.92 | 89.9 |
| MEDTONE ® (10 mg FDKP-insulin) | 30 | 11.23 | 2.93 | 91.7 |
| MEDTONE ® (10 mg FDKP) | 30 | 21.21 | 2.94 | 89.4 |

Example 8

Improvement in Bioavailability of FDKP with an Exemplary Embodiment of the Inhalation System To assess the safety and tolerability of various fill weights of TECHNOSPHERE® Inhalation Powder (FDKP-inhalation powder) delivered by DPI 1, described in Example 1 above, measurements were made using the inhalation system, i.e., inhaler and cartridge containing various fill weights of a dry inhalation powder, a modified CQLQ, VAS, and peak flows of the inhalation system. The MEDTONE® inhaler system was used for comparison. Experiments were also conducted to collect data from the systems in used in order to assess the effect of altering inhalation efforts and inhalation times on the pharmacokinetics (PK) of FDKP inhaled as FDKP-Inhalation Powder through the DPI 1 inhaler.

At the onset of the study, subjects were monitored and instructed to practice taking "short" and "long" inhalations with the inhalation system adapted with a pressure sensing device as disclosed in U.S. patent application Ser. No. 12/488,469, which can detect the presence of a dose emitted from the device in use. During an inhalation maneuver, the patient was instructed to maintain a nominal pressure differential of 4-6 kPa combined with a short inhalation of 3-4 seconds or a long inhalation of 6-7 seconds. To generate a "hard" inhalation, the subject provided a nominal inhalation time of about 6.5 seconds and a peak pressure of 7 kPa. Conversely, to generate an "easy" inhalation, the subject provided a nominal inhalation time of about 6.5 seconds and a peak pressure of 5 kPa. Coupled with the inhalation monitoring apparatus, gravimetric assessment of the powder mass discharged from the cartridge was performed. This enabled a linkage between inhalation maneuver during dosing, cartridge discharge mass and pharmacokinetic profile determinations for each subject.

The study was an open-label, crossover, 2-part study in healthy volunteers. In Part 1, a three-way, 3-period crossover study of 10 and 15 mg of FDKP inhalation powder was inhaled through the DPI 1 Inhaler and 10 mg through the MEDTONE® inhaler. Ten subjects were administered a dose of FDKP-inhalation powder and safety and tolerability measurements (CQLQ, VAS, and peak flows) were taken. Blood samples from the subjects were taken prior to dosing and at 5, 10, 15, 25, 30, 60, 120, 240 and 360 minutes after dosing to assess the pharmacokinetics of FDPK with each treatment.

In Part 2, after determining the tolerability of FDKP-inhalation powder in Part 1, mg were then used in Part 2. Part 2 was carried out as a 2-part, 2-way crossover study for evaluating the effect of flow rate (15 versus 30 LPM) and inhalation time (3 versus 6 seconds). For each parameter tested (i.e., flow rate, and inhalation time), ten subjects were crossed over for each parameter with 20 subjects total for all of the parameters. Pharmacokinetics of FDPK was assessed with each treatment from blood samples taken from the subjects. Measurements of pulmonary parameters (FEV1) were performed before and after inhalation of FDKP-inhalation powder. The results from these experiments are shown in the Table 7 and FIGS. 36 and 37.

Representative data of the results of the experiments are shown in Table 7 below which illustrates the mean $AUC_{0-6\ hr}$ for FDKP measured for the subjects tested as well as the mean $C_{max}$.

TABLE 7

| Treatment | Mean AUC (ng * min/mL) | SD AUC (ng * min/mL) | Mean Cmax (ng/mL) | SD Cmax (ng/mL) |
|---|---|---|---|---|
| DPI 1 10 mg (n = 10) | 28523 | 7375 | 189 | 96 |
| DPI 1 15 mg (n = 10) | 32031 | 17368 | 242 | 178 |
| MEDTONE ® 10 mg (n = 10) | 15143 | 3720 | 95 | 30 |

Figure 36:
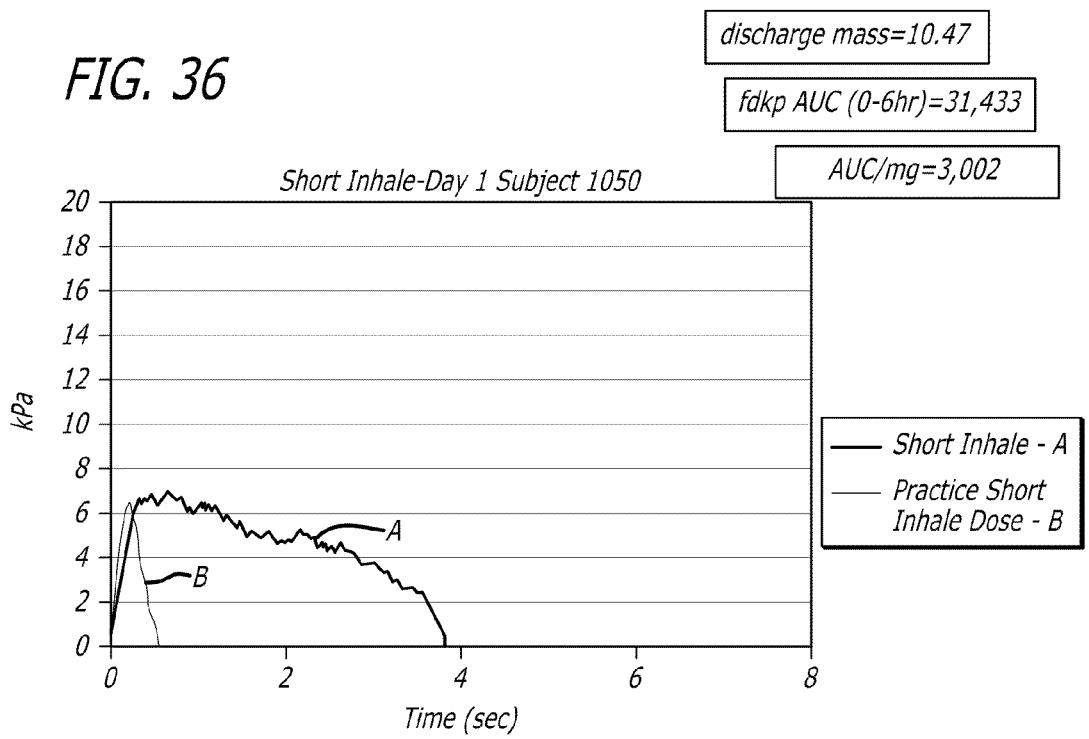
FIG. 36 depict graphs of inhalation recordings with an inhalation monitoring system and performed by a subject with an exemplary inhalation system without (curve A) and with (curve B) a powder formulation.
Figure 37:
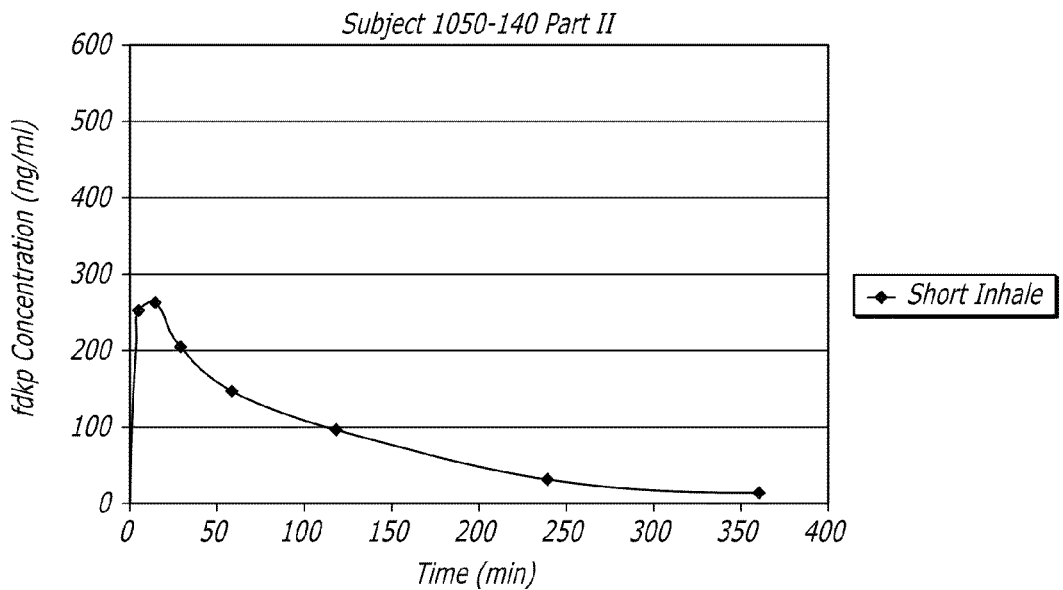
FIG. 37 is a graph of the concentration of FDKP in plasma from samples taken from the same subject as in FIG. 36 for 6 hours after inhalation of a dry powder formulation containing FDKP microparticles.

FIG. 36 depicts an example of a subject's profile using DPI 1 with a 10 mg dose of FDKP as monitored by the sensing device showing a practice inhalation without powder of about 4 seconds and a dosing inhalation of about 1 second with a powder dose of FDKP. FIG. 36 also shows that the discharge mass from the cartridge was gravimetrically measured as 10.47 mg, which resulted in the subject having a FDKP systemic exposure characterized by an $AUC_{0-6\ hrs}$ equaling 31,433 ng*min/mL. The normalized AUC/mg of delivered FDKP powder was 3,003 ng*min/mL per mg. FIG. 37 shows the FDKP concentration in blood plasma monitored for 6 hrs, which shows a $C_{max}$ of about 270 ng/mL in about 10 min.

The DPI 1 inhalation system containing 10 mg of FDKP powder delivered almost twice FDKP into the blood as the MEDTONE® inhaler containing 10 mg. The DPI 1 inhalation system containing 15 mg of FDKP-inhalation powder on average did not deliver a dose proportional in exposure as compared to DPI 1 system containing 10 mg of powder, due to several individuals not having good exposure to the powder, as seen in the significantly higher standard deviation. Variations of the data in Part 1 of the experiments may be due to some subjects not using the inhalers in the proper position during dosing.

The DPI 1 10 mg dose results for longer, shorter, harder or easier inhalation data compared to the MEDTONE® inhaler system are listed in Table 8. The study was conducted in three parts as indicated in Table 8. Table 8 illustrates delivery of the FDKP into the pulmonary circulation measured as the mean $AUC_{0-\infty}$ of FDKP values obtained in the experiments. The data is exemplary of the effectiveness and performance of the DPI 1 inhalation system compared to the MEDTONE® inhaler system and shows that DPI 1 was more effective at delivering the FDKP into the systemic circulation, at about 30% better than the MEDTONE® inhaler, wherein the values for DPI 1 ranged from $AUC_{0-\infty}$ 2375 to 5277 ng*min/mL per mg of FDKP emitted in the formulation. $AUC_{0-\infty}$ for MEDTONE® ranged from 1465 to 2403 ng*min/mL per mg of FDKP emitted in the formulation after two inhalations.

Example 9

Improvement in Bioavailability of FDKP and Insulin with an Exemplary Inhalation System This study was designed to assess the relative bioavailability of various fill weights of TECHNOSPHERE® insulin inhalation powder (FDKP-insulin) delivered by a pulmonary inhalation delivery system (DPI 2) compared with MEDTONE® inhaler, as determined by the pharmacokinetics (PK) of insulin and FDKP.

This was an open-label, crossover, PK (insulin and FDKP) study in healthy volunteers. C-peptide corrections were used to determine the relative amounts of insulin delivered by inhalation versus insulin of endogenous origin. Twenty four subjects (12 per arm) were administered a dose of 6.7 mg and 7.3 mg of FDKP-insulin inhalation powder (20 U and 22 U insulin, respectively and about 10% insulin w/w) using a DPI 2, and 10 mg FDKP-insulin inhalation powder (30 U insulin) using MEDTONE®. Subsequently, 12 subjects were given 20 U using DPI 2, or 30 U via MEDTONE® in a 3-way crossover arm of the study. Blood samples from the subjects were taken prior to dosing and at 7, 15, 30, 60, 120, 240 and 360 minutes after dosing to assess the pharmacokinetics of FDPK with each treatment.

TABLE 8

FDKP delivered via DPI 1 and MT in 3 part study

| | Part 1 | | Part 2 | | Part 3 | |
|---|---|---|---|---|---|---|
| | | | Inhaler System | | | |
| | DPI 1 | MT | DPI 1 | DPI 1 | DPI 1 | DPI 1 |
| cartridge fdkp content (mg) | 10 | 10 | 10 | 10 | 10 | 10 |
| inhalation technique | nominal time and inhalation effort | nominal time and inhalation effort | long inhalation time | short inhalation time | hard inhalation effort | easy inhalation effort |
| number of plasma analyses | 10 | 10 | 10 | 10 | 10 | 10 |
| AUC (0-inf) fdkp | | | | | | |
| mean (ng * min/mL) | 32575 | 17657 | 30488 | 31879 | 39324 | 38465 |
| SD | 7331 | 4281 | 8469 | 4713 | 11928 | 13248 |
| plus 1 SD | 39906 | 21938 | 38957 | 36592 | 51252 | 51713 |
| minus 1 SD | 25244 | 13376 | 22019 | 27166 | 27396 | 25217 |
| AVG emitted mass powder (mg) | 9.32 | 9.13 | 9.27 | 9.63 | 10.17 | 9.8 |
| AUC fdkp per emitted fdkp mass minus 1 SD | 2709 | 1465 | 2375 | 2821 | 2694 | 2573 |
| AVG mean AUC fdkp per emitted fdkp mass (ng * min/mL * mg fdkp) | 3495 | 1934 | 3289 | 3310 | 3867 | 3925 |
| AUC fdkp per emitted fdkp mass plus 1 SD | 4282 | 2403 | 4202 | 3800 | 5040 | 5277 |
| Cmax fdkp | | | | | | |
| mean (ng/mL) | 189 | 96 | 206 | 196 | 256 | 230 |
| SD | 96 | 30 | 88 | 86 | 95 | 99 |

FDKP 10 mg as delivered by the DPI 1 device is more efficient at delivering FDKP as measured by FDKP plasma AUC by an almost 2-fold increase over MEDTONE®. The delivery of FDKP is independent of inhalation time and inhalation effort. The data show that DPI 1 has an improved bioavailability and efficiency over MEDTONE® as assessed by FDKP AUC and the effect of altering inhalation parameters on FDKP AUC. The Cmax for FDKP in this study was greater than about 100 ng/mL with DPI 1 (one inhalation) and a lesser value using MEDTONE® (two inhalations), i.e., 96±30 ng/mL.

The data show that 20 U or 22 U insulin using DPI 2 delivered similar exposures of insulin and FDKP compared with 30 U of insulin administered with MEDTONE®. For insulin, results of plasma exposures ($AUC_{0-2hr}$) were 3407±1460 uU×min/mL vs. 4,154±1,682 uU*min/mL for DPI 2 20 U and MEDTONE® 30 U, respectively, and 4,661±2,218 uU*min/mL vs. 3,957±1,519 uU*min/mL for DPI 2 containing 22 U and MEDTONE® 30 U, respectively. In the 3-way crossover arm, plasma insulin exposures were 4,091±1,189 uU*min/mL and 3,763±1,652 uU*min/mL for DPI 2 and MEDTONE®, respectively.

The results from the 3-way study also showed a reduction in $T_{max}$ for insulin from 20.8±18.7 minutes in MEDTONE® to 14.8±8.94 minutes in DPI 2 (20 U) and to 13.6±4.3 minutes using the DPI 2 (22 U) system. In the 3-way cross-over study, wherein 6.7 mg FDKP-insulin was delivered in DPI 2 vs. 10.0 mg of FDKP-insulin powder delivered in MEDTONE®, FDKP plasma exposures ($AUC_{0-2hr}$) normalized for delivered mass were 2,059 ng*min/mL/mg (average of 16 subjects doses) for DPI 2 compared to 1,324 ng*min/mL/mg for MEDTONE® (average of 17 subjects doses). In this exemplary embodiment, the bioavailability studies were conducted with approximately 10% insulin content in the powder formulation. Accordingly, higher bioavailabilies (not normalized for powder content) can be obtained by providing a higher concentration of the insulin, and similar results can be accomplished with other active ingredients. Similarly, formulations containing higher contents of an active ingredient would yield lower bioavailabilies of FDKP (not normalized for powder content).

In summary, DPI 2 was more efficient at delivering insulin as measured by insulin plasma exposures than MEDTONE®. DPI 2 system delivered similar insulin exposures with 20 U of insulin as that of MEDTONE® with 30 U of insulin.

Further results from the experiments above are presented in the tables below. The study described in the immediately above example was continued in two additional parts. In the second part of this study subjects were given a dose of 10 U of insulin in an FDKP dry powder formulation using DPI 2, or 15 U of insulin in FDKP using the MEDTONE® inhalation system. In the 3$^{rd}$ part of this study, subjects were given 20 U of insulin in FDKP formulation using DPI 2 or 30 U using MEDTONE® in a 3-way crossover. Insulin concentration in blood was measured and the results were analyzed and evaluated.

Figure 38:
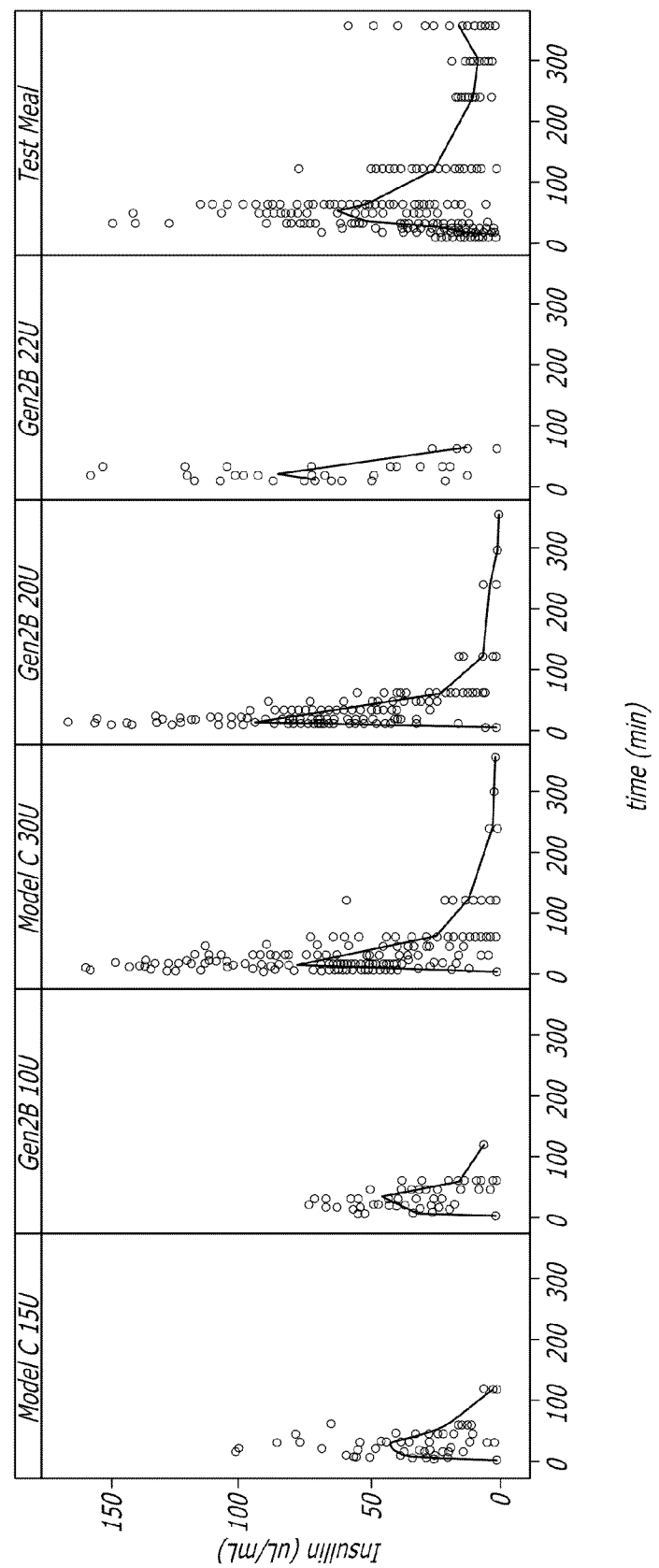
FIG. 38 is a graph of insulin concentrations over time by dose group.
Figure 39:
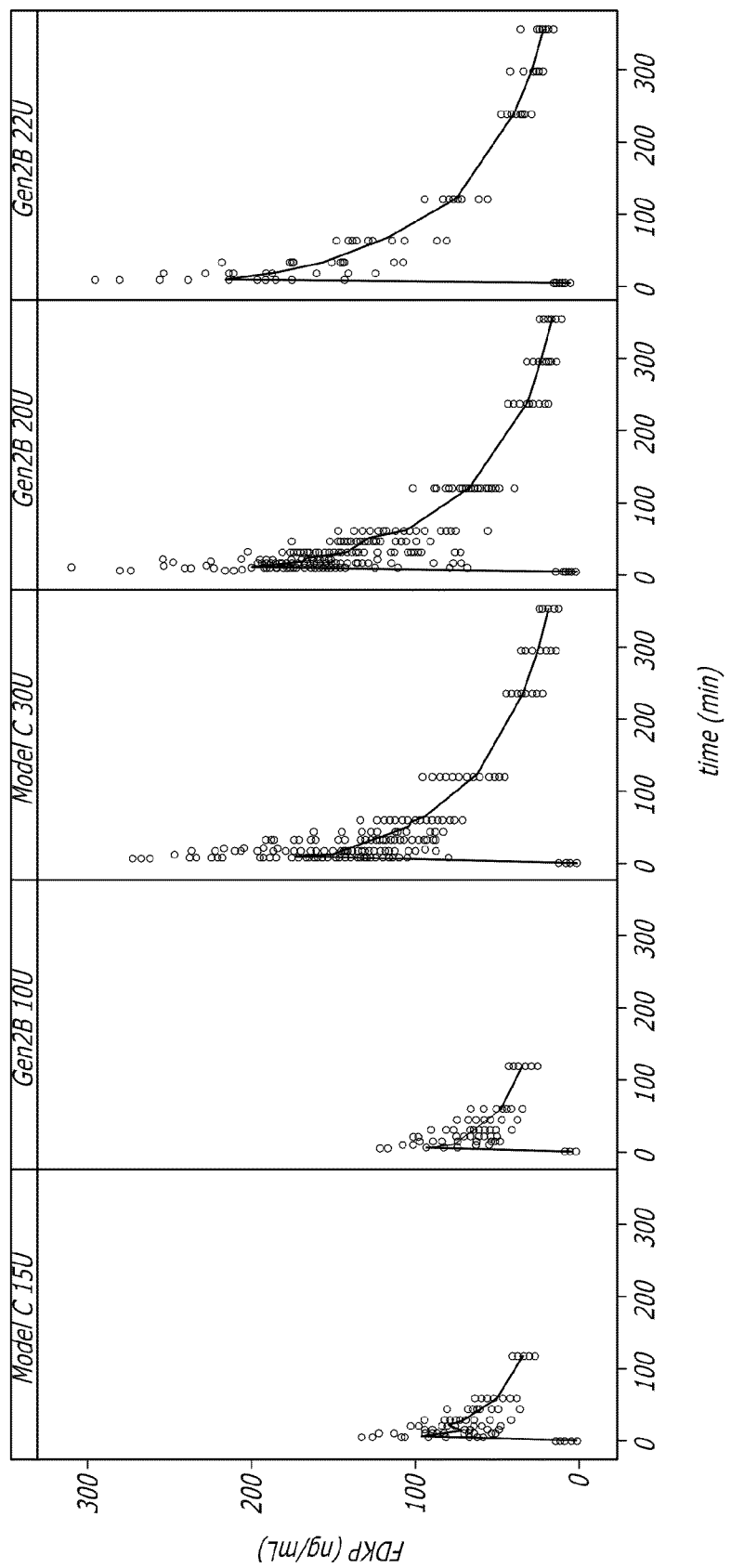
FIG. 39 is a graph of FDKP concentrations over time by dose group.

The plasma insulin and FDKP exposures ($AUC_{0-2\ hr}$) attained from subjects treated using DPI 2 20 U is similar to that obtained from subjects using the MEDTONE® Inhaler. The data are presented in Tables 9. The values presented were obtained from all of the dosing groups that used DPI 2 with 20 U of insulin, part I and III, while the values for the MEDTONE® Inhaler 30 U of insulin were obtained from parts I, Ia and III. Lower than expected AUC plasma exposure of insulin for DPI 2 22 U is most likely secondary to insufficient time points during the terminal elimination phase of insulin. It was recognized that some of the later time points were not contributing to the calculation of AUC and with an amendment were moved up in the timing sequence which gave improved results for $AUC_{last}$. This change in the insulin pharmacokinetic time points after the DPI 2 22 U insulin cohort was completed improved the subsequent concentration time profiles. The lower doses of DPI 2 10 U and MEDTONE® Inhaler 15 U were also similar. Insulin concentrations from all individuals are plotted in FIG. 38. The FDKP exposure from DPI 2 20 U and MEDTONE® Inhaler 30 U as well as the FDKP exposure for DPI 2 10 U and MEDTONE® Inhaler 15 U both fell within bioequivalent criteria. There is a good correlation with FDKP exposure and insulin exposure. FDKP concentrations from all individuals are plotted by dose group in FIG. 39.

The data in Table 9 is representative of the inhaler system performance disclosed herein and shows that the average plasma mean $AUC_{0-inf}$ measured for subjects in the experiment ranged from 1,879 to 3,383 ng*min/mL per mg of FDKP emitted with MEDTONE® with two inhalations and for DPI 2 from 2,773 to 5124 ng*min/mL per mg of FDKP emitted in the formulation after a single inhalation. The data also show that the average mean $AUC_{0-inf}$ for FDKP per mg of emitted FDKP mass in the formulation for all subjects was greater 3,500 or 3,568 ng*min/mL.

Plasma insulin average mean $AUC_{0-2hr}$ in this study for DPI 2 ranged from about 96 to 315 µU*min/mL per unit of insulin in the powder formulation administered in a single inhalation, wherein the average mean of insulin ranged from 168 to 216 µU*min/mL per unit of insulin in the powder formulation administered in a single inhalation. The $AUC_{0-inf}$ ($AUC_{0-\infty}$) values for MEDTONE ranged from about 76 to about 239 µU*min/mL per unit of insulin in the powder formulation administered in two inhalations. It has been previously noted that the first inhalation with the MEDTONE® inhaler system provides less than half the total insulin emitted with two inhalations per cartridge typically used (data not shown), and the same characteristic is similarly exhibited for FDKP when used as a delivery agent in the formulation.

Figure 40:
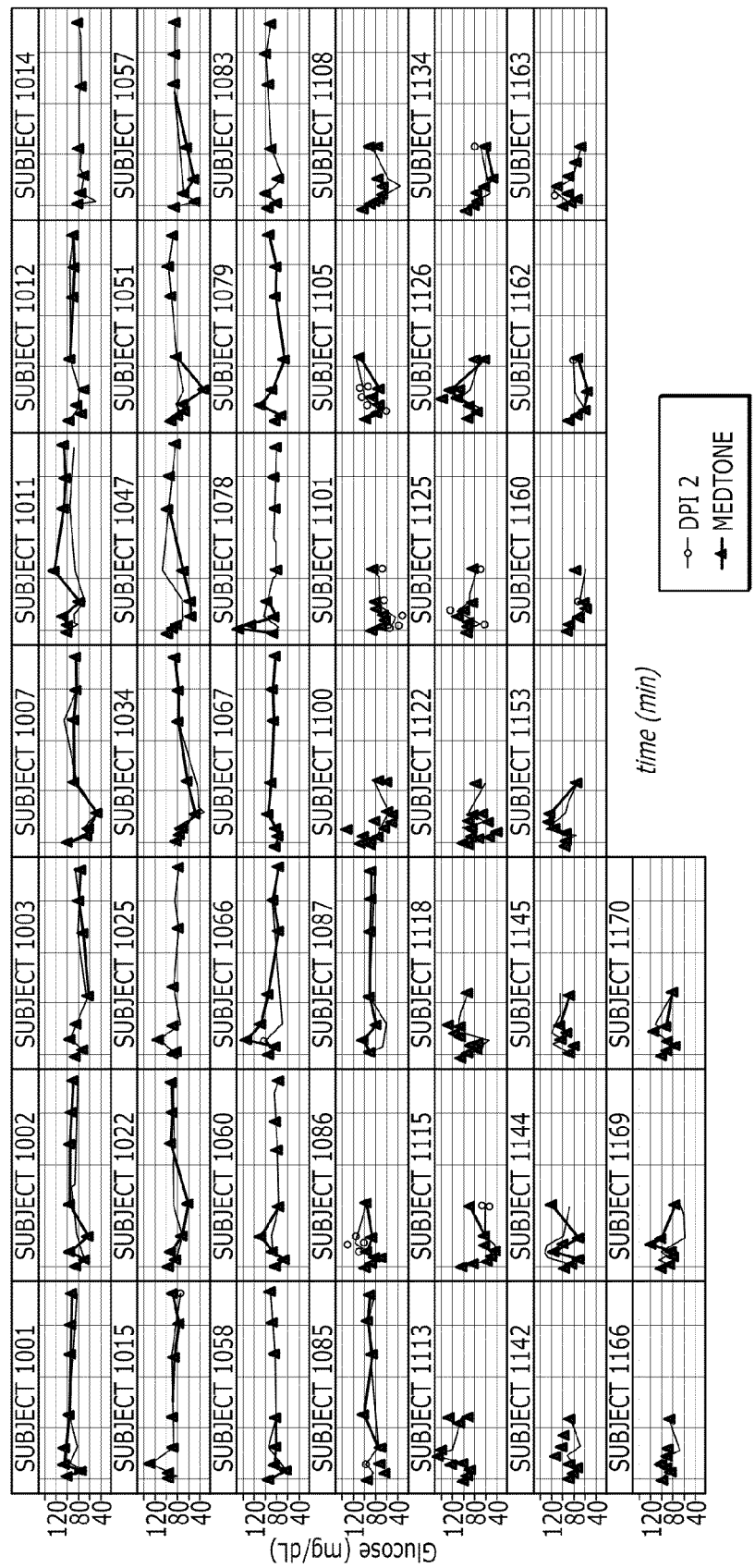
FIG. 40 is a graph of glucose excursions for each individual in the Study.

Post prandial glucose excursions were evaluated in each subject during the test meal used to establish the insulin C-Peptide relationship, as well as during meal challenges after the administration of insulin with DPI 2 or MEDTONE®. Glucose excursions in each individual comparing between DPI 2 or MEDTONE® are displayed in FIG. 40. The doses used in the study were not titrated to the individual, so the magnitude of the response varies from individual, but generally comparable glucose excursions were seen in each individual between the treatments with the two inhalers.

TABLE 9

FDKP and insulin Pharmacokinetic Parameters using FDKP-insulin dry powder formulation.

| | Part 1 | | Part 2 | | Part 3 | | Part 4 | |
| --- | --- | --- | --- | --- | --- | --- | --- | --- |
| | Inhaler System | | | | | | | |
| | DPI 2 | MT | DPI 2 | MT | DPI 2 | MT | DPI 2 | MT |
| cartridge content (units of insulin) | 20 | 30 | 22 | 30 | 10 | 15 | 20 | 30 |
| number of plasma analyses | 11 | 11 | 10 | 12 | 10 | 10 | 17 | 18 |
| AUC (0-2 hr) insulin | | | | | | | | |
| Mean (uU * min/mL) | 3407 | 4154 | 4661 | 3957 | 2268 | 2175 | 4091 | 3763 |
| SD | 1460 | 1682 | 2218 | 1519 | 958 | 1123 | 1189 | 1652 |
| Mean minus 1 SD | 1947 | 2472 | 2443 | 2438 | 1310 | 1052 | 2902 | 2111 |
| Mean plus 1 SD | 4867 | 5836 | 6879 | 5476 | 3226 | 3298 | 5280 | 5415 |
| AVG emitted powder mass (mg) | 6.78 | 9.13 | 7.27 | 9.24 | 3.49 | 4.59 | 6.81 | 9.14 |
| AVG emitted insulin content (U) | 20.34 | 27.39 | 21.81 | 27.72 | 10.47 | 13.77 | 20.43 | 27.42 |
| Mean AUC per emitted insulin content minus 1 SD | 95.72 | 90.25 | 112.01 | 87.95 | 125.12 | 76.40 | 142.05 | 76.99 |

TABLE 9-continued

FDKP and insulin Pharmacokinetic Parameters using FDKP-insulin dry powder formulation.

| | Part 1 | | Part 2 | | Part 3 | | Part 4 | |
| --- | --- | --- | --- | --- | --- | --- | --- | --- |
| | \multicolumn{8}{c}{Inhaler System} | | | | | | | |
| | DPI 2 | MT | DPI 2 | MT | DPI 2 | MT | DPI 2 | MT |
| AVG mean insulin AUC per emitted insulin content (uU * min/mL * U) | 167.50 | 151.66 | 213.71 | 142.75 | 216.62 | 157.95 | 200.24 | 137.24 |
| Mean AUC per emitted insulin content plus 1 SD | 239.28 | 213.07 | 315.41 | 197.55 | 308.12 | 239.51 | 258.44 | 197.48 |
| Cmax insulin | | | | | | | | |
| mean uU/mL | 76 | 86 | 127 | 103 | 53 | 49 | 103 | 89 |
| SD | 29 | 22 | 38 | 36 | 17 | 26 | 32 | 35 |
| AUC (0-inf) fdkp | | | | | | | | |
| mean (ng * min/mL) | 23826 | 23472 | 29107 | 26732 | 11084 | 11308 | 22462 | 19806 |
| SD | 6055 | 4019 | 4050 | 3932 | 2108 | 1332 | 4362 | 4524 |
| AVG emitted mass powder (mg) | 6.78 | 9.13 | 7.27 | 9.24 | 3.49 | 4.59 | 6.81 | 9.14 |
| AVG fdkp emitted content (mg) | 6.03 | 8.13 | 6.47 | 8.22 | 3.11 | 4.09 | 6.06 | 8.13 |
| Mean minus 1 SD | 17771 | 19453 | 25057 | 22800 | 8976 | 9976 | 18100 | 15282 |
| Mean plus 1 SD | 29881 | 27491 | 33157 | 30664 | 13192 | 12640 | 26824 | 24330 |
| mean AUC fdkp per emitted fdkp mass minus 1 SD | 2945 | 2394 | 3873 | 2773 | 2890 | 2442 | 2986 | 1879 |
| AVG mean AUG fdkp per emitted fdkp mass (ng * min/mL * mg fdkp) | 3948 | 2889 | 4499 | 3251 | 3568 | 2768 | 3706 | 2435 |
| mean AUC fdkp per emitted fdkp mass plus 1 SD | 4952 | 3383 | 5124 | 3729 | 4247 | 3094 | 4426 | 2991 |
| Cmax fdkp | | | | | | | | |
| mean (ng/mL) | 175 | 161 | 219 | 194 | 93 | 96 | 204 | 179 |
| SD | 69 | 29 | 49 | 49 | 23 | 25 | 46 | 57 |

The bioavailability of the inhalers was also assessed as compared to the bioavailability of fumaryl diketopiperazine or FDKP administered by intravenous bolus using radiolabeled FDKP and measured as AUC $AUC_{0-\infty}$. The results of this study showed that for the MEDTONE® system bioavailability was calculated to be about 26% and 32% for 10 mg and 20 mg, respectively of FDKP powder delivered. The bioavailable obtained measured using DPI 1 in a model analysis to deliver 10 mg of FDK was 57% when compared to a 10 mg of FDKP administered by an IV bolus injection. A model analysis of the data obtained using FDKP-insulin formulation was used to assess inhaler system performance or efficiency of powder delivered as measured by $AUC_{0-\infty}$ for FDKP using DPI 2 and a single inhalation of the powder. DPI 2 delivered 64% of the FDKP from a 6.7 mg of total fill into the systemic circulation as compared to 46% for MEDTONE® with two inhalations. For this FDKP-insulin formulation, the FDKP content was about 6 mg.

Example 10

Pharmacokinetic Parameters Based on C-Peptide Corrected Insulin Concentration Values and Geometric Means In an arm of the study conducted as described in Example 9, 46 healthy normal volunteers were studied using a Phase 1, open-label, randomized, crossover study protocol. The studies were conducted to evaluate the bioequivalence of FDKP-insulin formulation administered using DPI 2 inhalers which require a single inhalation to deliver a dose contained in a cartridge, when compared to MEDTONE®, which requires two inhalations per cartridge to deliver a dose. Additionally, the experiments were conducted to evaluate whether a dose of FDKP-insulin inhalation powder of two cartridges containing 10 U doses delivered an insulin concentration to a subject would be bioequivalent to one cartridge containing 20 U dose of insulin using DPI 2 inhalers and FDKP-insulin formulation administered by oral inhalation. Subjects were administered FDKP-insulin by oral inhalation using DPI 2 or MEDTONE®. Subjects received a single dose of 20 U insulin, two 10 U doses of insulin using DPI 2 inhalers or 30 U of insulin using a MEDTONE® inhaler. Blood samples were collected from each individual treated at various times for a period of 2 hours. The samples were analyzed to measure the insulin concentration. Pharmacokinetic parameters for the study were based on C-peptide corrected insulin concentration values. The results obtained from the study are shown in Table 10 below.

TABLE 10

| | 20 U DPI 2 vs. 30 U MEDTONE® | | |
| --- | --- | --- | --- |
| PK Parameter Statistics | 30 U MEDTONE® | 20 U DPI 2 | 20 U DPI 2 vs. 30 U MEDTONE® |
| $AUC_{0-120\,min}$ (min × µU/ml) 90% CI | 4060.3 | 4294.5 | Ratio 1.060 0.981-1.145 |
| Cmax (µU/ml) 90% CI | 97.4 | 105.2 | Ratio 1.082 0.992-1.180 |

TABLE 10-continued

| | 2 × 10 U DPI 2 vs. 20 U DPI 2 | | |
|---|---|---|---|
| PK Parameter Statistics | 2 × 10 U DPI 2 | 20 U DPI 2 | 2 × 10 U DPI 2 vs. 20U DPI 2 |
| $AUC_{0\text{-}120\,min}$ (min × μU/ml) 90% CI | 4136.5 | 4294.5 | Ratio 0.957 0.886-1.035 |
| Cmax (μU/ml) 90% CI | 98.3 | 105.2 | Ratio 0.930 0.852-1.014 |

The data indicate that using 20 U of insulin administered by oral inhalation to individuals using an FDKP-insulin formulation with a DPI 2 delivery system is bioequivalent statistically to administering 30 U of the same formulation using a MEDTONE® inhaler. The data also indicate that administering two 10 U doses of an FDKP-insulin formulation by oral inhalation with DPI 2 inhaler yields similar systemic exposure of insulin when compared to a single 20 U dose of insulin of an FDKP-insulin formulation using the same inhaler type or DPI 2. Therefore, two 10 U of insulin doses of FDKP-insulin formulation yields bioequivalent insulin concentration in the systemic circulation as a single 20 U dose of FDKP-insulin using the DPI 2 inhaler system and administered by pulmonary inhalation. The bioavailability data also indicate that using DPI 2 to dose patients, at least as exemplified with an insulin/FDKP formulation, that dosing with this inhalation system the dosing appears to be linear and proportional for at least the insulin rages tested, or from a 10 U to 30 U range.

The results also indicate that the DPI 2 delivery system is about 33% more efficient in delivering the same dose of the formulation. Therefore, DPI 2 provides similar exposures of an insulin dose with a dose reduction of 33% when compared to MEDTONE® inhaler.

Example 11

Figure 41:
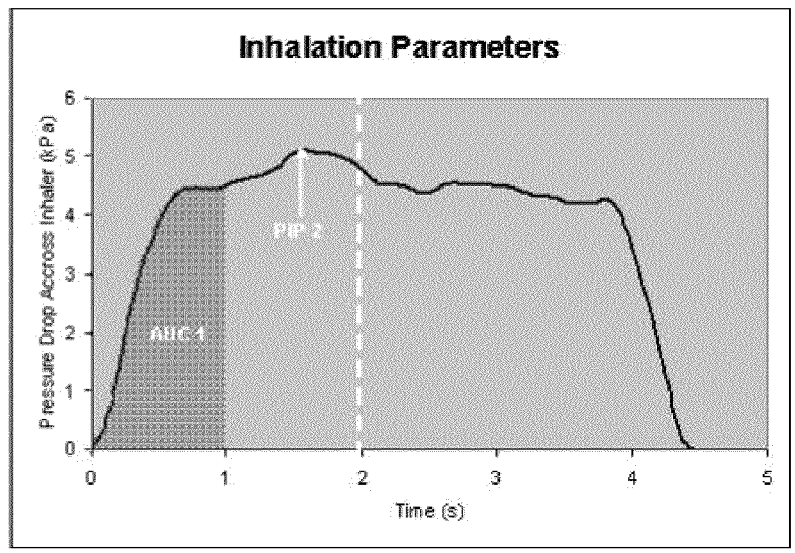
FIG. 41 is a graph of an exemplary inhalation profile of a present device in use showing peak inspiratory pressure within two seconds.

Characterization of Inhalation Profiles Using In Vitro Inhaler Performance Based Metrics An inhalation system described herewith consisting of a dry powder inhaler (DPI 2) with a cartridge. The DPI 2 was adapted with a BLUHALE™ apparatus as disclosed in U.S. patent application Ser. No. 12/488,469 (US 2009/0314292, which disclosure is incorporated herein by reference for all it teaches regarding inhalation maneuver and efforts and measurements thereof), which measures the pressure differential generated in an inhaler for a period of time during and after an inhalation maneuver. FIG. 41 is an exemplary graphic profile of a DPI 2 wherein the pressure drop across the inhaler was measured for a period of 5 seconds during and after a single inhalation. Peak inspiratory pressure in 2 sec, or PIP (2), denotes the highest point on the curve or highest pressure attained during the first two seconds after initiation of an inhalation. FIG. 41 shows that PIP (2) for the DPI 2 was about 5 kPa and the area under the curve within 1 second, or AUC (1) was 3.7 kPa*sec.

Example 12

Inhaler Performance Threshold Testing Based on Particle Size Diameter Tests

Figure 42:
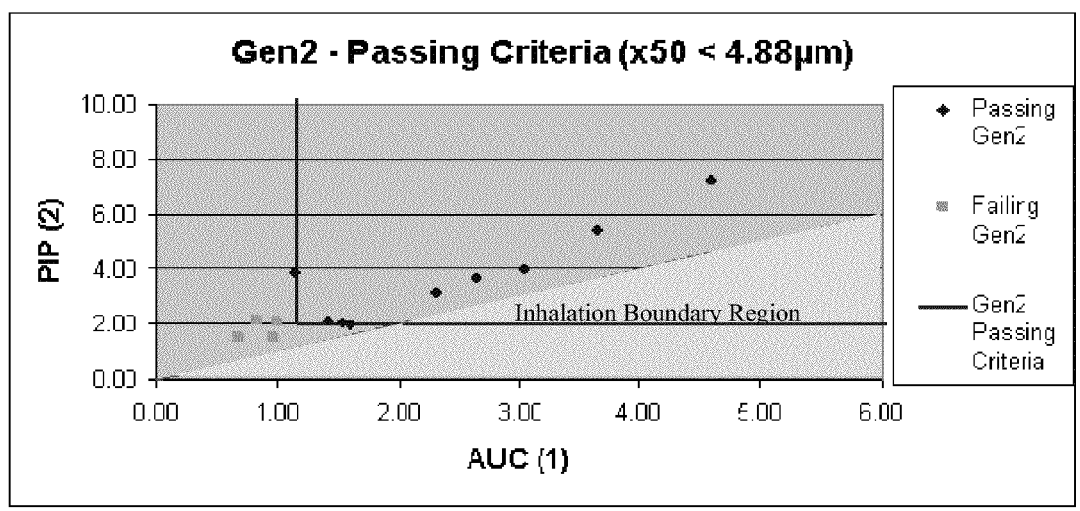
FIG. 42 is a graph of exemplary inhalers showing performance criteria for the present inhalers.

DPI 2 type inhalers were used in these experiments. Individual inhalers were loaded with a cartridge containing a dry powder formulation comprising microparticles comprising insulin and FDKP to test performance of the devices. The inhalers had been previously used to collect profiles as exemplified in Example 11 above. After collecting the inhalation profiles with BLUHALE™, the inhalers were adapted to an inhalation simulator as described in Patent Application No. PCT/US2010/055323, which disclosure is incorporated herein by reference for all it teaches regarding inhalation maneuver and efforts and measurements thereof, to reproduce exemplary inhalation by a user. The inhalation profiles using the simulator were then applied to discharge powder from two inhalers into a laser diffraction apparatus as described in Example 2 above to measure the particle size distribution. The laser diffraction apparatus measures the volumetric median geometric diameter (VMGD). Values were considered acceptable if 50% of the particles emitted were less than 4.88 μm in diameter, which was selected based on 33% increase in the average of particle size for a DPI 2 used optimally. Two inhalers with powder doses were loaded into the laser diffraction apparatus and powder discharges or emissions were obtained with the various inhalations profiles, i.e., various PIP (2) and AUC (1) values. The test was repeated 5 times for each inhaler for a total of ten measurements and the data was analyzed and plotted FIG. 42 shows the results of the experiments as a graph of PIP (2) versus AUC (1) for the two inhalers, in which each point on the graph represents the average of 10 discharges. The cartridge emptying (or dry powder emitted) was greater than 87% during all discharges. The triangular inhalation boundary region of the graph represents the area on the graph where PIP (2) values are physically impossible to attain for a device given the AUC (1) values. Inhalation maneuvers that were deemed to have passing criteria based on the above specifications and were above and to the right of the Gen 2 passing criteria lines in FIG. 42 had acceptable performance. The data in FIG. 42 show that the lower limit for acceptable performance of the present devices is at PIP (2) of about 2 kPa and AUC (1) at least about 1.2 kPa*sec. However in other experiments, acceptable performance has also been demonstrated at an AUC (1) of at least about 1.0 or at least about 1.1 kPa*sec.

The preceding disclosures are illustrative embodiments. It should be appreciated by those of skill in the art that the devices, techniques and methods disclosed herein elucidate representative embodiments that function well in the practice of the present disclosure. However, those of skill in the art should, in light of the present disclosure, appreciate that many changes can be made in the specific embodiments that are disclosed and still obtain a like or similar result without departing from the spirit and scope of the invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects those of ordinary skill in the art to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above cited references and printed publications are herein individually incorporated by reference in their entirety.

Further, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A dry powder inhaler comprising:
a) a mouthpiece;

b) a housing comprising a cartridge-mounting area and a cartridge, the cartridge comprising a movable container having a dry powder, the container configured to move with respect to the cartridge and the cartridge configured to form a flow path between one or more inlet ports and one or more dispensing ports within the housing; and c) at least one rigid air conduit;

wherein the rigid air conduit is configured so that the dry powder inhaler emits greater than about 75% of the dry powder from the container oriented in the container housing as powder particles in a single inhalation, and the powder particles emitted have a volumetric median geometric diameter of less than about 5 microns when the single inhalation through the mouthpiece generates a peak inspiratory pressure of about 2 kPa within two seconds.

2. The dry powder inhaler of claim 1 having a resistance value to airflow ranging from about 0.065 (√kPa)/liter per minute to about 0.200 (√kPa)/liter per minute.

3. The dry powder inhaler of claim 1, wherein the dry powder is a formulation for pulmonary delivery and comprises an amount from about 1 mg to about 30 mg of the dry powder.

4. The dry powder inhaler of claim 1, wherein the dry powder comprises a diketopiperazine or a pharmaceutically acceptable salt thereof.

5. The dry powder inhaler of claim 4, wherein the diketopiperazine is of the formula 2,5-diketo-3,6-bis(N—X-4-aminobutyl)piperazine, wherein X is selected from the group consisting of fumaryl, succinyl, maleyl, and glutaryl.

6. The dry powder inhaler of claim 5, wherein the diketopiperazine is

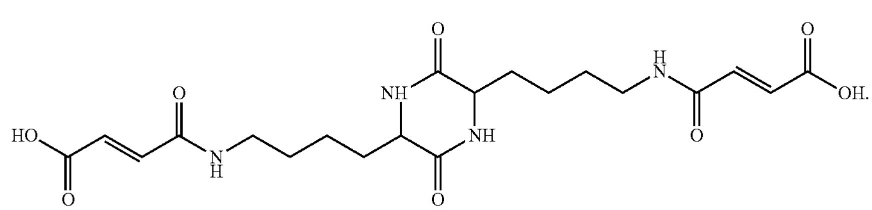 [SMILES: O=C(O)/C=C/C(=O)NCCCCC1NC(=O)C(CCCCNC(=O)/C=C/C(=O)O)NC1=O]

.

7. The dry powder inhaler of claim 1, wherein the dry powder comprises a drug or an active agent.

8. The dry powder inhaler of claim 7, wherein the active agent is an endocrine hormone.

9. The dry powder inhaler of claim 1, wherein the dry powder comprises a peptide, a polypeptide, or fragments thereof, a small organic molecule or a nucleic acid molecule.

10. The dry powder inhaler of claim 9, wherein said peptide is insulin, glucagon, glucagon-like peptide-1, parathyroid hormone, oxytocin, oxyntomodulin, peptide YY, an exendin, analogs thereof or fragments thereof.

11. The dry powder inhaler of claim 9, wherein the small organic molecule is a vasodialator, a vasoconstrictor, a neurotransmitter agonist or a neurotransmitter antagonist.

12. The dry powder inhaler of claim 1, wherein the single inhalation generates an area under the curve (AUC) from a pressure versus time curve within one second of at least about 1.0, 1.1 or 1.2 kPa*sec.

13. The dry powder inhaler of claim 1, wherein the container is integrated into the container housing and filled with a dry powder.

14. A method of delivering of a dry powder using a high resistance dry powder inhaler comprising:
providing a dry powder inhaler with an airflow resistance value ranging from about 0.065 ($\sqrt{kPa}$)/liter per minute to about 0.200 ($\sqrt{kPa}$)/liter per minute, and containing the dose of the dry powder within cartridge comprising a container configured to move with respect to the cartridge to form a flow path for the delivery of the dry powder;
applying sufficient force to reach a peak inspiratory pressure of at least 2 kPa within 2 seconds; and
generating an area under the curve in the first second (AUC0-1 sec) of a inspiratory pressure versus time curve of at least about 1.0, 1.1 or 1.2 kPa*sec;
wherein greater than 75% of the dose of the dry powder is discharged or emitted from the inhaler as powder particles.

15. The method of claim 14, wherein the dry powder is a formulation for pulmonary delivery and comprises an amount from about 1 mg to about 30 mg of the dry powder.

16. The method of claim 15, wherein the dry powder comprises a diketopiperazine or a pharmaceutically acceptable salt thereof.

17. The method of claim 16, wherein the diketopiperazine is of the formula 3,6-bis(N—X-4-aminobutyl)-2,5-diketopiperazine, wherein X is selected from the group consisting of fumaryl, succinyl, maleyl, and glutaryl.

18. The method of claim 17, wherein the diketopiperazine is

19. The method of claim 18, wherein the dry powder formulation comprises fumaryl diketopiperazine microparticles which upon discharge from the dry powder inhaler are measured to have a volumetric median geometric diameter (VMGD) ranging from about 2 μm to 8 μm and a geometric standard deviation of less than 4 μm.

20. The method of claim 14, wherein the dry powder formulation comprises a drug or an active agent selected from the group consisting of a small organic molecule, peptide, polypeptide, a protein, or a nucleic acid molecule.

21. The method of claim 20, wherein the small organic molecule is a vasoactive agent, a neurotransmitter agonist, a neurotransmitter antagonist, or a steroid molecule.

* * * * *